US010829538B2

(12) United States Patent
Czerniecki et al.

(10) Patent No.: US 10,829,538 B2
(45) Date of Patent: Nov. 10, 2020

(54) IDENTIFICATION OF IMMUNOGENIC MHC CLASS II PEPTIDES FOR IMMUNE-BASED THERAPY

(71) Applicant: THE TRUSTEES OF THE UNIVERSITY OF PENNSYLVANIA, Philadelphia, PA (US)

(72) Inventors: Brian J. Czerniecki, Tampa, FL (US); Gary K. Koski, Akron, OH (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/327,006

(22) PCT Filed: Apr. 7, 2016

(86) PCT No.: PCT/US2016/026542
§ 371 (c)(1),
(2) Date: Jan. 17, 2017

(87) PCT Pub. No.: WO2017/014816
PCT Pub. Date: Jan. 26, 2017

(65) Prior Publication Data
US 2018/0111976 A1 Apr. 26, 2018

Related U.S. Application Data

(63) Continuation-in-part of application No. PCT/US2016/021042, filed on Mar. 4, 2016, which is a continuation-in-part of application No. PCT/US2015/041034, filed on Jul. 17, 2015.

(51) Int. Cl.
| | |
|---|---|
| *A61K 38/00* | (2006.01) |
| *A61K 39/00* | (2006.01) |
| *C07K 14/71* | (2006.01) |
| *G01N 33/574* | (2006.01) |
| *C07K 16/32* | (2006.01) |
| *A61P 35/00* | (2006.01) |
| *G01N 33/569* | (2006.01) |

(52) U.S. Cl.
CPC .............. *C07K 14/71* (2013.01); *A61K 38/00* (2013.01); *A61K 39/0011* (2013.01); *A61K 39/001106* (2018.08); *A61P 35/00* (2018.01); *C07K 16/32* (2013.01); *G01N 33/56972* (2013.01); *G01N 33/57407* (2013.01); *G01N 33/57415* (2013.01); *G01N 33/57492* (2013.01); *A61K 2039/5154* (2013.01); *A61K 2039/5158* (2013.01); *A61K 2039/54* (2013.01); *A61K 2039/55* (2013.01); *A61K 2039/812* (2018.08); *A61K 2039/828* (2018.08); *G01N 2333/70514* (2013.01); *G01N 2333/71* (2013.01)

(58) Field of Classification Search
CPC ............ A61K 38/00; A61K 2039/5154; A61K 2039/5158; A61K 2039/812; C07K 14/71
See application file for complete search history.

(56) References Cited

U.S. PATENT DOCUMENTS

| | | | |
|---|---|---|---|
| 7,919,098 B2 * | 4/2011 | Zhou .................. | A61K 39/0011 424/185.1 |
| 2008/0057064 A1 | 3/2008 | Zhou | |
| 2008/0175855 A1 | 7/2008 | Hardy et al. | |
| 2010/0112603 A1 | 5/2010 | Moecks et al. | |
| 2010/0291573 A1 | 11/2010 | Cowens et al. | |
| 2011/0229478 A1 | 9/2011 | Zhou | |
| 2011/0229524 A1 | 9/2011 | Fritsche et al. | |
| 2011/0269158 A1 | 11/2011 | Zitzler et al. | |
| 2013/0183343 A1 | 7/2013 | Czerniecki et al. | |
| 2013/0330324 A1 | 12/2013 | Elis et al. | |
| 2014/0112931 A1 | 4/2014 | Chardes et al. | |
| 2014/0370053 A1 | 12/2014 | Del et al. | |

FOREIGN PATENT DOCUMENTS

| | | |
|---|---|---|
| WO | 1991008214 A1 | 6/1991 |
| WO | 2006043271 A1 | 4/2006 |
| WO | 2007115571 A2 | 10/2007 |
| WO | 2007146959 A2 | 7/2008 |
| WO | 2009157919 A1 | 12/2009 |
| WO | 2012156532 A1 | 11/2012 |
| WO | 2015048793 A2 | 4/2015 |
| WO | 2016011343 A1 | 1/2016 |

OTHER PUBLICATIONS

Cancer information from National Institute of Cancer, Apr. 29, 2010, pp. 1-2.*
Datta et al., Journal for ImmunoTherapy of Cancer, Nov. 6, 2014, vol. 2, Supp. Suppl. 3. Abstract No. P47.*
Sharma et al., Cancer, 2012, 118: 4354-62.*
Datta, Jashodeep et al., Association of Depressed Anti-HER2 T-Helper Type 1 Response With Recurrence in Patients With Completely Treated HER2-Positive Breast Cancer : Role for Immune Monitoring, JAMA Oncology, vol. 2, No. 2, Feb. 1, 2016, pp. 242-246, XP055556159, ISSN: 2374-2437, doi:10.1001/jamaoncol.2015.5482.
Masuelli, Laura et al., Gene-specific inhibition of breast carcinoma in BALB-neuT mice by active immunization with rat Neu or human ErbB receptors, International Journal of Oncology, Feb. 1, 2007, vol. 30, Issue 2, pp. 381-392.
Miller, Megan Jo et al., HER-3 peptide vaccines/mimics: Combined therapy with IGF-1R, HER-2, and HER-1 peptides induces synergistic anti-tumor effects against breast and pancreatic cancer cells, OncoImmunology, Nov. 1, 2014, vol. 3, Issue 10, pp. 1-17, Taylor & Francis Group, LLC.

(Continued)

*Primary Examiner* — Hong Sang
(74) *Attorney, Agent, or Firm* — Riverside Law LLP

(57) ABSTRACT

The invention provides compositions, methods, and vaccines that may stimulate the immune system and that may be used for treating malignancies associated with overexpression of the HER3 protein. Such compositions include epitopes of the HER3 protein.

3 Claims, 36 Drawing Sheets
Specification includes a Sequence Listing.

(56) References Cited

OTHER PUBLICATIONS

Park, Y.H. et al., Role of HER3 expression and PTEN loss in patients with HER2-overexpressing metastatic breast cancer (MBC) who received taxane plus trastuzumab treatment, British Journal of Cancer, Dec. 17, 2013, vol. 110, pp. 384-391.
Peng, Dunfa et al., Alterations in Barrett's-related adenocarcinomas: A proteomic approach, International Journal of Cancer, vol. 122, No. 6, Mar. 15, 2008, pp. 1303-1310, DOI:10.1002/ijc.23258.
Schaefer, Gabriele et al., A Two-in-One Antibody against HER3 and EGFR Has Superior Inhibitory Activity Compared with Monospecific Antibodies, Cancer Cell, Oct. 18, 2011, vol. 20, pp. 472-486, Elsevier Inc.

\* cited by examiner

IDENTIFICATION OF IMMUNOGENIC MHC CLASS II PEPTIDES FOR IMMUNE-BASED THERAPY

CROSS-REFERENCE TO RELATED APPLICATIONS

This is a national phase filing under 35 U.S.C. § 371 of the Patent Cooperation Treaty of International Patent Application No. PCT/US16/26542, filed Apr. 7, 2016, which is a continuation-in-part of International Patent Application Serial No. PCT/US16/21042, filed Mar. 4, 2016, which, in turn, is a continuation-in-part of International Patent Application Serial No. PCT/US15/41034, filed Jul. 17, 2015, which, in turn, claims priority and benefit from U.S. Provisional Patent Application Ser. No. 62/076,789 filed Nov. 7, 2014, and U.S. Provisional Patent Application Ser. No. 62/025,681 filed Jul. 17, 2014, the entire contents of each of which are incorporated herein by reference.

BACKGROUND

In 25-30% of breast cancers, amplification and overexpression of the growth factor receptor gene HER2 (human epidermal growth factor receptor-2, also known as neu/erbB2) is associated with enhanced tumor aggressiveness and a high risk of relapse and death (Slamon. D., et al., 1987, Science 235:177: Yarden, Y., 2001, Oncology 1:1). This oncogene encodes a 185 kilodalton (kDa) transmembrane receptor tyrosine kinase ("RTK"). As one of the four members of the human epidermal growth factor receptor ("EGFR") family, HER2 distinguishes itself in several ways. First, HER2 is an orphan receptor. No high-affinity ligand has been identified. Second, HER2 is a preferred partner for other EGFR family members (HER1/EGFR, HER3, and HER4) for the formation of heterodimers, which show high ligand affinity and superior signaling activity. Third, full-length HER2 undergoes proteolytic cleavage, releasing a soluble extracellular domain ("ECD"). Shedding of the ECD has been shown to represent an alternative activation mechanism of full-length HER2 both in vitro and in vivo, as it leaves a membrane-anchored fragment with kinase activity. The central role of HER2 in EGFR family signaling correlates with its involvement in the oncogenesis of several types of cancers, such as breast, ovarian, colon, and gastric cancers, regardless of its expression level (Slamon, D., et al., 1989, Science 244:707; Hynes, N., et al., 1994, Biochem. Biophys. Acta. 1198:165). HER2 may also render tumor cells resistant to certain chemotherapeutics (Pegram, M., et al., 1997, Oncogene 15:537). Given its vital role in tumorigenesis, HER2 is an important target for cancer therapeutics.

The human EGF receptor ("HER") family of RTKs regulates a large variety of biological processes including cell proliferation, -migration, -invasion and -survival. The family consists of four members: EGFR (HER1), HER2 (neu or ErbB2), HER3 (ErbB3) and HER4 (ErbB4). To date, eleven ligands have been reported including epidermal growth factor ("EGF"), heparin-binding EGF-like growth factor ("HB-EGF"), transforming growth factor .alpha. (TGFα), amphiregulin (AR), epiregulin, betacellulin and the heregulins. These ligands bind directly to their cognate receptors, which leads to the formation of receptor homo- or heterodimers that trigger the activation of multiple signaling pathways. Dysregulation of members of the HER-family either by activating mutations, receptor over expression or aberrant ligand release leads to the development of a variety of human tumors. HER3 is over expressed in breast-, ovarian- and lung cancer and this genetic feature has been correlated with poor prognosis. Upon activation by heregulins, HER3 dimerizes with HER2 and EGFR to form potent oncogenic receptor heterodimers. Within this complex, HER3 preferentially recruits PI3 kinase to its cytoplasmic docking sites thereby regulating cell proliferation and -survival. So far it was assumed that HER3 is kinase-inactive due to apparently aberrant sequence characteristics in its kinase domain and that it requires heterodimerization with a kinase-intact member of the HER-family in order to initiate signaling events. Consistent with this, it was shown that HER2 requires HER3 to drive breast tumor cell proliferation. However, recent findings of showed that HER3 is able to phosphorylate Pyk2 which results in the activation of the MAPK pathway in human glioma cells. Furthermore, monoclonal antibodies specific for HER3 can inhibit the proliferation and migration of cancer cell lines. Interestingly, it was shown recently that cancer cells escape HER-family inhibitor therapy by up-regulation of HER3 signaling and that HER3 inhibition abrogates HER2-driven tamoxifen resistance in breast cancer cells. Moreover, resistance to Gefitinib (Iressa) therapy, an EGFR small molecule inhibitor, was shown to be connected to HER3 signal activation.

HER3 is a receptor protein that plays an important role in regulating normal cell growth. HER3 lacks an intrinsic kinase activity and relies on the presence of HER2 to transduce signals across the cell membrane. As initially transcribed, the pre-mRNA for HER3 contains 28 exons and 27 introns. The fully spliced HER3 mRNA from which the introns have been spliced out is composed of 28 exons.

Targeted therapy has emerged as the cornerstone of cancer therapeutics in the last decade. Members of the EGF receptor family—namely EGFR (or HER1) and ErbB2 (or HER2/neu)—have evolved as particularly attractive targets, since these RTKs are deregulated in a multitude of cancers. The oncogenic functions of another member of the EGF receptor family—ErbB3 or HER3—have only been recently scrutinized due its major role in mediating resistance to HER2 and PI3K pathway-directed therapies. Activating mutations in and/or overexpression of HER3 has been identified in a number of different tumor types, including breast, gastric, colon, bladder cancer, and melanoma, and portend a worse overall prognosis in these tumors.

Despite advances in the field, it is still uncertain whether effective immune responses can be generated in humans using cell- or protein-based vaccine strategies targeting HER3. Accordingly, there is a need in the art to have additional immunotherapeutic approaches for treating or preventing breast cancer and other malignancies with which overexpression of the HER3 protein is associated. The present embodiments fulfill this need.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2 also shows HER3 screen with single peptides (SEQ ID NOS 4-7, respectively, in order of appearance).

FIG. 3 also shows HER3 screen with single peptides (SEQ ID NOS 4 and 7, respectively, in order of appearance).

FIG. 4 also shows HER3 screen with single peptides (SEQ ID NOS 1-3, respectively, in order of appearance).

FIG. 24A shows cumulative anti-HER3 CD4 Tcell response as measured by IFN-γ spots per million cells via ELISpot assay declined significantly going from HDs to BDs to DCIS to HER2$^{pos}$ IBC to ER$^{pos}$ IBC and finally to TN IBC (90 versus 80 versus 66 versus 79 versus 48 versus 40, p=0.01, respectively). FIG. 24B shows repertoire, or the number of HER3 peptides with a positive CD4 Th1 response, declined significantly going from HDs to BDs to DCIS to HER2$^{pos}$ IBC to ER$^{pos}$ IBC and finally to TN IBC (1.0 versus 0.6 versus 0.8 versus 0.8 versus 0.5 versus 0.3, p=0.003, respectively). FIG. 24C shows responsivity, the percent of subjects responding to at least 1 peptide, declined significantly going from HDs to BDs to DCIS to HER2$^{pos}$ IBC to ER$^{pos}$ IBC and finally to TN IBC (76.7% versus 63.6% versus 53.8% versus 66.7% versus 45.0% versus 33.3%, p=0.02, respectively).

FIG. 25A shows there were no statistically significant differences in tetanus response as measured by IFN-γ spots per 200,000 cells via ELISpot assay between HDs, BDs, DCIS. HER2 IBC/HER2$^{pos}$ IBC. ER IBC/ER$^{pos}$ IBC or TN IBC (37 versus 30 versus 19 versus 34 versus 24 versus 29, p=0.65, respectively). FIG. 25B shows there were no statistically significant differences in anti-CD3/anti-CD28 polyclonal stimulation as measured by IFN-γ spots per 200,000 cells via ELISpot assay between HDs, BDs, DCIS, HER2 IBC/HER2$^{pos}$ IBC, ER IBC/ER$^{pos}$ IBC or TN IBC (688 versus 549 versus 804 versus 699 versus 629 versus 675, p=0.68, respectively).

FIG. 26A has four histograms comparing IBC patients' immune responses by lymph node status at initial surgery (lymph node positive ("LN+" or "LN$^{pos}$") versus lymph node negative ("LN-" or "LN$^{neg}$")) showing there were no statistically significant differences in cumulative response (top panel) (40 versus 56, p=0.12, respectively), repertoire (second panel) (0.4 versus 0.6, p=0.08, respectively), responsivity (third panel) (35.7% versus 54.8%, p=0.19, respectively) or tetanus response (bottom panel) (22 versus 29, p=0.35, respectively) between $LN^{pos}$ and $LN^{neg}$ IBC patients. FIG. 26B has four histograms comparing IBC patients' immune responses by recurrence versus non-recurrence (disease-free) in patients who were at least 1 year our from diagnosis had significantly lower cumulative response (top panel) (17 versus 66, p=0.04, respectively), repertoire (second panel) (0.0 versus 0.6, p<0.05, respectively) and responsivity (third panel) (0% versus 55.6%, p=0.01, respectively). There was no difference in tetanus response between recurrent and non-recurrent IBC patients (bottom panel) (27 versus 35, p=0.65, respectively). FIG. 26C has four histograms comparing IBC patients' immune responses by response to neo-adjuvant chemotherapy (pathologic complete response ("pCR") versus residual disease ("<pCR")). Of patients receiving neo-adjuvant chemotherapy, those with a pCR, compared to those with <pCR, displayed significantly higher cumulative response (top panel) (144 versus 32, p=0.004, respectively) and repertoire (second panel) (0.8 versus 0.4, p=0.05, respectively). There was no difference in responsivity (third panel) (80.0% versus 27.3%, p=0.10, respectively) or tetanus response (bottom panel) (17 versus 59, p=0.15, respectively) between pCR and <pCR patient immune responses.

FIG. 27A has four histograms comparing HD patients' immune responses by age (<50 years old ("yo") versus >50 years old). There were no statistically significant differences by age in cumulative response (top panel) (77 versus 103, p=0.25, respectively), repertoire (second panel) (0.8 versus 1.1, p=0.38, respectively), responsivity (third panel) (72.0% versus 75.0%, p=1.0, respectively) or tetanus response (bottom panel) (39 versus 30, p=0.40, respectively). FIG. 27B has four histograms comparing HD patients' immune responses by race (Caucasian versus African American versus Other). There were no statistically significant differences by race in cumulative response (top panel) (87 versus 83 versus 95, p)=0.96, respectively), repertoire (second panel) (0.9 versus 0.7 versus 1.4, p=0.31, respectively), responsivity (third panel) (69.0% versus 71.4% versus 100%, p=0.35, respectively) or tetanus response (bottom panel) (33 versus 51 versus 26, p=0.30, respectively). FIG. 27C has four histograms comparing HD patients' immune responses by pregnancy history/parity (0 pregnancies versus 1 or more pregnancies) There were no statistically significant differences by pregnancy history in cumulative response (top panel) (82 versus 91, p=0.71, respectively), repertoire (second panel) (1.0 versus 0.9, p=0.62, respectively) or responsivity (third panel) (76.5% versus 70.8%6, p=0.74, respectively). Of interest, tetanus response (bottom panel) was significantly higher in nulliparous females compared to those with at least one pregnancy (47 versus 27, p=0.04, respectively). FIG. 27D has four histograms comparing HD patients' immune responses by menopausal status (pre-menopausal versus post-menopausal). Post-menopausal HDs/BDs, compared to pre-menopausal HDs/BDs, displayed significantly higher cumulative response (top panel) (136 versus 70 spots per million cells, p=0.005, respectively) and repertoire (second panel) (1.4 versus 0.8 peptides, p=0.03, respectively). There was no difference between post- and pre-menopausal HD/sBDs by responsivity (third panel) (90.9% versus 66.7%, p=0.23, respectively) or tetanus response (bottom panel) (38 versus 28, p=0.37, respectively).

DETAILED DESCRIPTION

Figure 1:
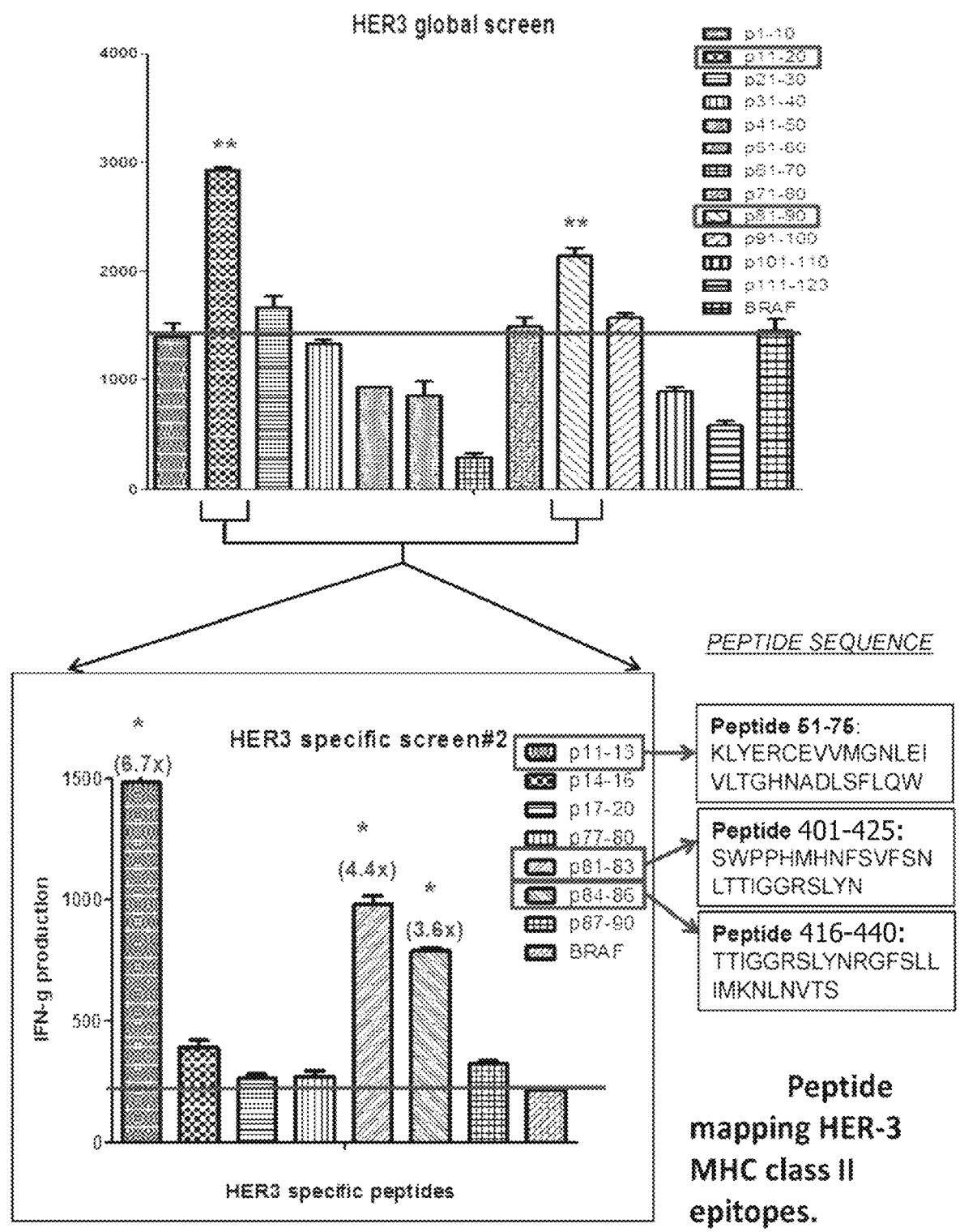
FIG. 1 shows immunogenic peptides from HER3 that exhibit the ability to activate CD4 T cells across many patients (SEQ ID NOS 1-3, respectively, in order of appearance).

The present embodiments provide isolated peptides of the HER family of proteins as well as other RTKs. In one embodiment, there are isolated peptides of one or more of HER 1, HER3, and c-MET protein. In one embodiment, a peptide represents an epitope of HER1. In one embodiment, the peptide represents an epitope of HER3. In one embodiment, the peptide represents an epitope of c-MET.

In some embodiments, the epitope of the corresponding HER family of proteins as well as other RTKs is immunogenic. The present embodiments additionally provide compositions that include one or more peptides of the embodiments. In one embodiment, there is provided a chimeric peptide, wherein the chimeric peptide comprises one or more peptides of the embodiments.

One embodiment includes a composition comprising a multivalent peptide. The multivalent peptide includes two or more of the peptides of the invention.

Methods of stimulating an immune response and methods of treating cancer in a subject are additionally provided. Vaccines are also provided for therapeutic and prophylactic use. The peptides of the embodiments, either alone or in the context of chimeric peptides, as described herein, are capable of invoking an immune response. In one embodiment, the immune response is a humoral response. In another embodiment, the immune response is a cell-mediated response. According to some embodiments, the peptides of the invention confer a protective effect.

In another embodiment HER3 expression can be used as a marker of tumor progression in premalignant lesions of the gastroesophageal junction.

In another embodiment anti-HER3CD4 Th1 loss is determined comprising use of HER3 MHC Class II immunogenic peptides.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example. "an element" means one element or more than one element.

"About" as used herein when referring to a measurable value such as an amount, a temporal duration, and the like, is meant to encompass variations of ±20%, or ±10%, or ±5%, or 11%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Adjuvant therapy" for breast cancer as used herein refers to any treatment given after primary therapy (i.e., surgery) to increase the chance of long-term survival. "Neoadjuvant or neo-adjuvant therapy" or is treatment given before primary therapy.

The term "antigen" or "ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" ("APC") is a cell that are capable of activating T cells, and includes, but is not limited to, monocytes/macrophages. B cells and dendritic cells (DCs).

"Antigen-loaded APC" or an "antigen-pulsed APC" includes an APC, which has been exposed to an antigen and activated by the antigen. For example, an APC may become Ag-loaded in vitro, e.g., during culture in the presence of an antigen. The APC may also be loaded in vivo by exposure to an antigen. An "antigen-loaded APC" is traditionally prepared in one of two ways: (1) small peptide fragments, known as antigenic peptides, are "pulsed" directly onto the outside of the APCs; or (2) the APC is incubated with whole proteins or protein particles which are then ingested by the APC. These proteins are digested into small peptide fragments by the APC and are eventually transported to and presented on the APC surface. In addition, the antigen-loaded APC can also be generated by introducing a polynucleotide encoding an antigen into the cell.

"Anti-HER3 response," "anti-HER3 CD4 Th1 response" "anti-HER3 CD4 T cell response" and the like refer to the immune response specifically against HER3 protein.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome. Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, mvxedema, pernicious anemia, ulcerative colitis, among others.

As used herein, the term "autologous" is meant to refer to any material derived from the same individual to which it is later to be re-introduced into the individual.

The term "B cell" as used herein is defined as a cell derived from the bone marrow and/or spleen. B cells can develop into plasma cells which produce antibodies.

The term "cancer" as used herein is defined as a hyper-proliferation of cells whose unique trait—loss of normal control—results in unregulated growth, lack of differentiation, local tissue invasion, and/or metastasis. Examples include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, germ-cell tumors, and the like.

"CD4+ Th1 cells," "Th1 cells," "CD4+T-helper type 1 cells," "CD4+ T cells," and the like are defined as a subtype of T-helper cells that express the surface protein CD4 and produce high levels of the cytokine IFN-γ. See also, "T-helper cells."

"Cumulative response" means the combined immune response of a patient group expressed as the total sum of reactive spots (spot-forming cells "SFC" per $10^6$ cells from IFN-γ ELISpot analysis) from all MHC class II binding peptides from a given patient group.

"DC vaccination," "DC immunization," "DC1 immunization," and the like refer to a strategy using autologous dendritic cells to harness the immune system to recognize specific molecules and mount specific responses against them.

The term "dendritic cell" or "DC" is an antigen presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. DCs have a characteristic morphology with thin sheets (lamellipodia) extending in multiple directions away from the dendritic cell body. Typically, dendritic cells express high levels of MHC and costimulatory (e.g., B7-1 and B7-2) molecules. Dendritic cells can induce antigen specific differentiation of T cells in vitro, and are able to initiate primary T cell responses in vitro and in vivo. In the context of vaccine production, an "activated DC" is a DC that has been exposed to a Toll-like receptor agonist such as lipopolysaccharide "LPS." An activated DC may or may not be loaded with an antigen.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

A "HER receptor" is a receptor protein tyrosine kinase which belongs to the HER receptor family and includes EGFR (ErbB1, HER1), HER2 (ErbB2), HER3 (ErbB3) and HER4 (ErbB4) receptors. The HER receptor will generally comprise an extracellular domain, which may bind an HER ligand and/or dimerize with another HER receptor molecule: a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is a native sequence human HER receptor.

The "HER pathway" refers to the signaling network mediated by the HER receptor family.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"HER2" is a member of the human epidermal growth factor receptor ("EGFR") family. HER2 is overexpressed in approximately 20-25% of human breast cancer and is expressed in many other cancers.

"HER2$^{pos}$" is the classification or molecular subtype of a type of breast cancer as well as numerous other types of cancer. HER2 positivity is currently defined by gene amplification by FISH (fluorescent in situ hybridization) assay and 2+ or 3+ on intensity of pathological staining.

"HER2$^{neg}$" is defined by lack of gene amplification by FISH, and can encompass a range of pathologic staining form 0 to 2+ in most cases.

"HER3" and "ErbB3" refer to the receptor polypeptide as disclosed, for example, in U.S. Pat. Nos. 5,183,884 and 5,480,968 as well as Kraus et al. PNAS (USA) 86:9193-9197 (1989).

"HER3 extracellular domain" or "HER3ECD" refers to a domain of HER3 that is outside of a cell, either anchored to a cell membrane, or in circulation, including fragments thereof. In one embodiment, the extracellular domain of HER3 may comprise four domains: Domain I, Domain 11, Domain 111, and Domain IV. In one embodiment, the HER3ECD comprises amino acids 1-636 (numbering including signal peptide). In one embodiment, HER3 domain III comprises amino acids 328-532 (numbering including signal peptide).

"HER3 immunogenic peptides," HER3 binding peptides," "HER3 epitopes" and the like as used herein refer to MHC Class II peptides derived from or based on the sequence of the HER3 protein, specifically HER3ECD, and their equivalents. HER3 peptides can activate CD4 T cells across many patients. The peptides can be used to pulse dendritic cells and educate T cells to recognize HER3. HER3 is expressed in triple negative breast cancer and can impart resistance to anti-estrogen in ER$^{pos}$ breast cancers. HER3 is also expressed in other cancers, including melanoma, lung, colon, prostate cancer, and metastatic brain tumors. According to a preferred embodiment four HER3 immunogenic peptides (epitopes) or binding peptides have been identified as follows:

```
                                       (SEQ ID NO: 4)
p12 (Peptide 56-70):    CEVVMGNLEIVLTGH;

(SEQ ID NO: 5)
p81 (Peptide 401-415):  SWPPHMHNVSVFSNL;

(SEQ ID NO: 6)
p84 (Peptide 416-430):  TTIGGRSLYNRGFSL;
and (SEQ ID NO: 7)
p91 (Peptide 451-465):  AGRIYISANRQLCYH.
```

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5TATGGC3' share 50% homology.

In addition, when the terms "homology" or "identity" are used herein to refer to the nucleic acids and proteins, it should be construed to be applied to homology or identity at both the nucleic acid and the amino acid sequence levels.

The term "hyperproliferative disease" is defined as a disease that results from a hyperproliferation of cells. Exemplary hyperproliferative diseases include, but are not limited to, cancer or autoimmune diseases. Other hyperproliferative diseases may include vascular occlusion, restenosis, atherosclerosis, or inflammatory bowel disease, for example.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Immune response" as used herein means the activation of a host's immune system, e.g., that of a mammal, in response to the introduction of antigen. The immune response can be in the form of a cellular or humoral response, or both.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Metrics" of CD4+ Th responses or "metrics of immune responses" are defined for each subject group analyzed for anti-HER3 CD4+ Th1 immune response: (a) overall anti-HER3 responsivity (expressed as percent of subjects responding to 1 immunogenic peptide); (b) response repertoire (expressed as mean number of immunogenic peptides (n) recognized by each subject group); and (c) cumulative response (expressed as total sum of reactive spots (spot-forming cells "SFC" per $10^6$ cells from IFN-γ ELISpot analysis) from 4 MHC Class II HER3 immunogenic peptides from each subject group.

A "peptide," "protein," or "polypeptide" as used herein can mean a linked sequence of amino acids and can be natural, synthetic, or a modification or combination of natural and synthetic.

As used herein, a "population" includes reference to an isolated culture comprising a homogenous, a substantially homogenous, or a heterogeneous culture of cells. Generally, a "population" may also be regarded as an "isolated" culture of cells.

Receptor tyrosine kinases ("RTKs") are the high-affinity cell surface receptors for many polypeptide growth factors, cytokines, and hormones. The human EGF receptor ("HER") family of RTKs regulates a large variety of biological processes including cell proliferation, migration, invasion, and survival. The family consists of four members: HER1 (ErbB1), HER2 (neu or ErbB2), HER3 (ErbB3), and HER4 (ErbB4).

As used herein, a "recombinant cell" is a host cell that comprises a recombinant polynucleotide.

"Responsivity" or "anti-HER3 responsivity" are used interchangeably herein to mean the percentage of subjects responding to at least 1 of 4 HER3 immunogenic peptides.

"Response repertoire" is defined as the mean number ("n") of HER3 immunogenic peptides recognized by each subject group.

"Sample" or "biological sample" as used herein means a biological material from a subject, including but is not limited to organ, tissue, exosome, blood, plasma, saliva, urine and other body fluid. A sample can be any source of material obtained from a subject.

"Signal 1" as used herein generally refers to the first biochemical signal passed from an activated DC to a T cell. Signal 1 is provided by an antigen expressed at the surface of the DC and is sensed by the T cell through the T cell receptor.

"Signal 2" as used herein generally refers to the second signal provided by DCs to T cells. Signal 2 is provided by "costimulatory" molecules on the activated DC, usually CD80 and/or CD86 (although there are other co-stimulatory molecules known), and is sensed by the T cell through the surface receptor CD28.

"Signal 3" as used herein generally refers to the signal generated from soluble proteins (usually cytokines) produced by the activated DC. These are sensed through receptors on the T lymphocyte. The $3^{rd}$ signal instructs the T cell as to which phenotypical or functional features they should acquire to best deal with the current threat.

By the term "specifically binds," as used herein, is meant a molecule, such as an antibody, which recognizes and binds to another molecule or feature, but does not substantially recognize or bind other molecules or features in a sample.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The term "targeted therapies" as used herein refers to cancer treatments that use drugs or other substances that interfere with specific target molecules involved in cancer cell growth usually while doing little damage to normal cells to achieve an anti-tumor effect. Traditional cytotoxic chemotherapy drugs, by contrast, act against all actively dividing cells. In breast cancer treatment monoclonal antibodies, specifically trastuzumab/HERCEPTIN® targets the HER2/neu receptor.

The terms "T cell" or T-cell" as used herein is defined as a thymus-derived cell that participates in a variety of cell-mediated immune reactions.

The term "T-helper" as used herein with reference to cells indicates a sub-group of lymphocytes (a type of white blood cell or leukocyte) including different cell types identifiable by a skilled person. In particular, T-helper cell according to the present disclosure include effector Th cells (such as Th1, Th2 and Th17). These Th cells secrete cytokines, proteins or peptides that stimulate or interact with other leukocytes.

The terms "T-helper cells," "helper T cells," "Th cells," and the like are used herein with reference to cells indicates a sub-group of lymphocytes (a type of white blood cell or leukocyte) including different cell types identifiable by a skilled person in the art. In particular, T-helper cells are effector T cells whose primary function is to promote the activation and functions of other B and T lymphocytes and/or macrophages. Helper T cells differentiate into two major subtypes of cells known as "Th1" or "Type 1" and "Th2" or "Type 2" phenotypes. These Th cells secrete cytokines, proteins, or peptides that stimulate or interact with other leukocytes.

"Th1 cell," "CD4+ Th1 cell," "CD4+T-helper type 1 cell," "CD4+ T cell" and the like as used herein refer to a mature T-cell that has expressed the surface glycoprotein CD4. CD4+T-helper cells become activated when they are presented with peptide antigens by MHC class 11 molecules which are expressed on the surface of antigen-presenting peptides ("APCs") such as dendritic cells. Upon activation of a CD4+T helper cell by the MHC-antigen complex, it secretes high levels of cytokines such as interferon-γ ("IFN-γ"). Such cells are thought to be highly effective against certain disease-causing microbes that live inside host cells, and are critical in antitumor response in human cancer against certain disease-causing microbes that live inside host cells, and cancer as well.

"Th17 T cell" as used herein refers to a T cell that produces high levels of the cytokines IL-17 and IL-22 and is thought to be highly effective against disease-causing microbes that live on mucousal surfaces.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

"Triple negative" and "TN" breast cancer refer to any breast cancer cells that test negative for estrogen receptor ("ER"), progesterone receptor ("PR") and HER2.

The term "vaccine" as used herein is defined as a material used to provoke an immune response after administration of the material to an animal, preferably a mammal, and more preferably a human. Upon introduction into a subject, the vaccine is able to provoke an immune response including, but not limited to, the production of antibodies, cytokines and/or other cellular responses.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyle et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The embodiments provide an immunological composition comprising a peptide of a HER family of proteins as well as other RTKs. In one embodiment, there are provided isolated peptides of one or more of HER1, HER3, and c-MET protein. In one embodiment, the peptides are useful in eliciting an immune response. A composition comprising a peptide of the embodiments is useful as a prophylactic therapeutic agent for initial protection as well as useful as a therapeutic agent for treatment of an ongoing condition.

The present invention also provides methods for treating or preventing cancer. Such methods involve the step of administering to a subject in need thereof a peptide or combinations of peptides of the invention. Administration of such peptide(s) results in the induction of anti-tumor immunity. Thus, the present invention provides methods for inducing anti-tumor immunity in a subject, such methods involving the step of administering to the subject the peptide or combination of peptides of the invention, as well as pharmaceutical compositions and cellular compositions derived thereof.

The invention encompasses a method for inducing a T cell response to in a mammal. The method comprises administering an antigen presenting cell (APC) that specifically induces proliferation of a T cell. In one embodiment, method comprises administering a dendritic cell vaccine pulsed with a peptide of the invention to thereby specifically induce proliferation of a T cell against the antigen corresponding to the peptide.

In one embodiment, APCs pulsed with the peptide of the invention can be used to culture expand T cells. Once sufficient numbers of antigen-specific T cells are obtained using the APC to expand the T cell, the antigen-specific T cells so obtained are administered to the mammal, thereby inducing an antigen specific T cell response in the mammal.

The invention includes a preparation of activated DCs. In one embodiment, the DC preparations are greater than 90% pure. In another embodiment, the DC preparations are fully activated. For example, the DCs are activated with a DC activation regimen comprising contacting the DC with a TLR agonist (e.g., LPS). In another embodiment, the DCs are activated with a calcium mobilizing treatment in conjunction with other DC activation regimens (e.g., activating agents) that enhance different $3^{rd}$ signal cytokines.

The present invention includes mature, antigen loaded DCs activated by any DC activation regimen. The DCs of the present invention produce desirable levels of cytokines and chemokines. In one embodiment, the invention provides a method to pulse and activate cells, whereby the cells maintain the active state following cryopreservation. A benefit of the DC preparation of the invention is that the cells are efficiently cryopreserved from a single leukapheresis (patient collection) into an initial vaccine plus multiple "booster" doses (e.g., 10 or more) that can be thawed as needed at remote treatment locations without any specialized cell processing facilities or further required quality control testing.

The present invention also relates to the cryopreservation of these activated DCs in a manner that retains their potency and functionality in presenting antigen as well as their production of various cytokines and chemokines after thawing, such that the cryopreserved and subsequently thawed activated DCs are as clinically effective as freshly harvested and activated DCs.

As contemplated herein, the present invention provides a method for generating and cryopreserving DCs with superior functionality in producing stronger signals to T cells, and thus resulting in a more potent DC-based vaccine. By effectively cryopreserving such cells, samples can be stored and thawed for later use, thereby reducing the need for repeated pheresis and elutriation processes during vaccine production. Being able to freeze DCs and then thaw them out later is an advantage because it means that a single round of vaccine production can be divided into small parts, frozen away, and then administered one at a time to a patient over the course of weeks, months, or years to give "booster" vaccinations that strengthen immunity.

The present embodiments also include use of HER3 expression as a marker of tumor progression in premalignant lesions of the gastroeophageal junction, also known as Barrett's esophagus. The marker has prognostic and therapeutic uses in invasive esophagogastric carcinoma.

Compositions

The present invention provides isolated peptides of the HER family of proteins as well as other RTKs. In one embodiment, the invention provides isolated peptides of one or more of HER1, HER3, and c-MET protein. In one embodiment, the peptides of the invention represent epitopes of the corresponding HER or c-MET protein. In some embodiments, the epitopes of the corresponding HER or c-MET protein are immunogenic.

The present invention provides compositions that include one or more peptides of the invention. The present invention also provides compositions that include one or more chimeric peptides. In one embodiment, the chimeric peptides include one more of the epitopes of the corresponding HER or c-MET protein.

Additionally, compositions having one or more multivalent peptides are provided. These multivalent peptides include two or more of the epitopes of the invention.

Methods of stimulating an immune response and methods of treating cancer in a subject using the compositions of the invention are included in the invention. Vaccines are also provided for therapeutic and prophylactic use. The epitopes of the invention, either alone or in the context of chimeric peptides, as described herein, is capable of invoking an immune response. In one embodiment, the immune response is a humoral response. In another embodiment, the immune response is a cell mediated response. According to some embodiments, the epitopes or peptides of the invention confer a protective effect.

In one embodiment, the HER3 epitopes or otherwise peptides of the invention include:

```
p11-13 (Peptide 51-75):
                                     (SEQ ID NO: 1)
KLYERCEVVMGNLEIVLTGHNADLSFLQW;

p81-83 (Peptide 401-425):
                                     (SEQ ID NO: 2)
SWPPHMHNFSVFSNLTTIGGRSLYN;

p84-86 (Peptide 416-440):
                                     (SEQ ID NO: 3)
TTIGGRSLYNRGFSLLIMKNLNVTS;

p12 (Peptide 56-70):
                                     (SEQ ID NO: 4)
CEVVMGNLEIVLTGH;

p81 (Peptide 401-415):
                                     (SEQ ID NO: 5)
SWPPHMHNFSVFSNL;

p84 (Peptide 416-430):
                                     (SEQ ID NO: 6)
TTIGGRSLYNRGFSL;

p91 (Peptide 451-465):
                                     (SEQ ID NO: 7)
AGRIYISANRQLCYH;
```

The HER3 peptides or any peptide of the invention may be cyclized or linear. When cyclized, the epitopes may be cyclized in any suitable manner. For example, disulfide bonds may be formed between selected cysteine (Cys) pairs in order to provide a desired confirmation. It is believed that the formation of cyclized epitopes may provide conformations that improve the humoral response, thus improving the protective effect.

The HER3 epitope identified by SEQ ID NO: 4 represents positions 56-70 of the HER3 protein. The HER3 epitope identified by SEQ ID NO: 5 represents positions 401-415 of the HER3 protein. The HER3 epitope identified by SEQ ID NO: 6 represents positions 416-430 of the HER3 protein.

The HER3 epitope identified by SEQ ID NO: 7 represents positions 451-465 of the HER3 protein.

As described herein, the HER3 epitopes of the invention also encompass peptides that are functional equivalents of the peptides identified by SEQ ID NOs. Such functional equivalents have an altered sequence in which one or more of the amino acids in the corresponding HER3 epitope sequence is substituted or in which one or more amino acids are deleted from or added to the corresponding reference sequence. For example 1 to 3 amino acids may be added to the amino terminus, carboxy terminus, or both. In some examples, the HER3 epitopes are glycosylated.

In other examples, the HER3 epitopes may be the retro-inverso isomers of the HER3epitopes. The retro-inverso modification comprises the reversal of all amide bonds within the peptide backbone. This reversal may be achieved by reversing the direction of the sequence and inverting the chirality of each amino acid residue by using D-amino acids instead of the L-amino acids. This retro-inverso isomer form may retain planarity and conformation restriction of at least some of the peptide bonds.

Non-conservative amino acid substitutions and/or conservative substitutions may be made. Substitutions are conservative amino acid substitutions when the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid. e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

In some examples, the deletions and additions are located at the amino terminus, the carboxy terminus, or both, of one of the sequences of the peptides of the invention. For example, the HER3 epitope equivalent has an amino acid sequence which is at least 70% identical, at least 80% identical, at least 85% identical, at least 90% identical, at least 91%, at least 92%, at least 93%, at least 94%, at least 95%, at least 96%, at least 97%, at least 98%, or at least 99% identical to the corresponding HER3 epitope sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using known or to be developed programs in the art.

For functional equivalents that are longer than a corresponding HER3 epitope sequence, the functional equivalent may have a sequence which is at least 90% identical to the HER3 epitope sequence and the sequences which flank the HER3 epitope sequences in the wild-type HER3 protein.

Functional equivalents of the HER3 epitopes may be identified by modifying the sequence of the epitope and then assaying the resulting polypeptide for the ability to stimulate an immune response, e.g., production of antibodies. Such antibodies may be found in a variety of body fluids including sera and ascites. Briefly, a body fluid sample is isolated from a warm-blooded animal, such as a human, for whom it is desired to determine whether antibodies specific for HER3 polypeptide are present. The body fluid is incubated with HER3 polypeptide under conditions and for a time sufficient to permit immunocomplexes to form between the polypeptide and antibodies specific for the protein and then assayed, preferably using an ELISA technique.

In accordance with other embodiments of the present invention, chimeric peptides and compositions comprising one or more chimeric peptides are provided. According to various embodiments, the chimeric peptides comprise a HER3 epitope, another epitope, and a linker joining the HER3 epitope to the other epitope. In one embodiment, the other epitope can include but is not limited to another HER3 epitope, a HER1 epitope, a HER2 epitope, and a c-Met epitope. It will be further understood that any suitable linker may be used. For example, depending upon the epitope used, the HER3 epitope may be linked to either the amino or the carboxy terminus of the other epitope. The location and selection of the other epitope depends on the structural characteristics of the HER3 epitope, whether alpha helical or beta-turn or strand.

In one embodiment, the linker may be a peptide of from about 2 to about 15 amino acids, about 2 to about 10 amino acids, or from about 2 to about 6 amino acids in length. The chimeric peptides may be linear or cyclized. Additionally, the HER3 epitopes, the other epitopes, and/or the linker may be in retro-inverso form. Thus the HER3 epitope along could be in retro inverso form. Alternatively, the HER3 epitope and the other epitope could be in retro inverso form. In another example, the HER3 epitope, the other epitope, and the linker could be in retro inverso form.

In another embodiment, the peptides of the invention can be in a mixture together instead of being in a form of a chimeric peptide. In any event, the compositions of the invention comprising the peptides may be useful agents to pulse antigen presenting cells (e.g., dendritic cells) for the generation of cellular vaccines. In another embodiment, the compositions of the invention comprising the peptides may be useful immunogens for inducing production of antibodies. The compositions of the invention may also be used to immunize a subject and retard or prevent tumor development. The compositions of the invention may be used in vaccines to provide a protective effect.

In accordance with additional embodiments of the present invention, compositions comprising a mixture of two or more of the peptides or chimeric peptides of the invention are provided. In some examples, the HER3 epitope of each of the two or more chimeric peptides are different. In other examples, one of the HER3 epitopes is selected from SEQ ID NOs: 1-7.

Peptides, including chimeric peptides, of the present invention can be prepared using well known techniques. For example, the peptides can be prepared synthetically, using either recombinant DNA technology or chemical synthesis. Peptides of the present invention may be synthesized individually or as longer polypeptides composed of two or more peptides. The peptides of the present invention are preferably isolated, i.e., substantially free of other naturally occurring host cell proteins and fragments thereof.

The peptide and chimeric peptides of the invention may be synthesized using commercially available peptide synthesizers. For example, the chemical methods described in Kaumaya et al., "De Novo" Engineering of Peptide Immunogenic and Antigenic Determinants as Potential Vaccines, in Peptides, Design, Synthesis and Biological Activity (1994), pp 133-164, which is specifically incorporated herein by reference, may be used. For example, HER3 epitopes may be synthesized co-linearly with the other epitope to form a chimeric peptide. Peptide synthesis may be performed using Fmoc/t-But chemistry. The peptides and chimeric peptides may be cyclized in any suitable manner. For example, disulfide bonds may be achieved using differentially protected cysteine residues, iodine oxidation, the addition of water to boost removal of Acm group and the concomitant formation of a disulfide bond, and/or the silyl chloride-sulfoxide method.

The peptides and chimeric peptides may also be produced using cell-free translation systems and RNA molecules derived from DNA constructs that encode the epitope or peptide. Alternatively, the epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, microinjection, cationic lipid-mediated transfection, electroporation, transduction, scrape lading, ballistic introduction or infection.

The peptides of the present invention may contain modifications, such as glycosylation, side chain oxidation, or phosphorylation; so long as the modifications do not destroy the biological activity of the peptides. Other modifications include incorporation of D-amino acids or other amino acid mimetics that can be used, for example, to increase the serum half-life of the peptides.

The peptides of the invention can be prepared as a combination, which includes two or more of peptides of the invention, for use as a vaccine for a disease, e.g. cancers. The peptides may be in a cocktail or may be conjugated to each other using standard techniques. For example, the peptides can be expressed as a single polypeptide sequence. The peptides in the combination may be the same or different.

The present invention should also be construed to encompass "mutants," "derivatives," and "variants" of the peptides of the invention (or of the DNA encoding the same) which mutants, derivatives and variants are peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein.

The invention also provides a polynucleotide encoding at least one peptide selected from a peptide having the sequence of any one or more of SEQ ID NOs 1-7. The nucleic acid sequences include both the DNA sequence that is transcribed into RNA and the RNA sequence that is translated into a peptide. According to other embodiments, the polynucleotides of the invention are inferred from the amino acid sequence of the peptides of the invention. As is known in the art several alternative polynucleotides are possible due to redundant codons, while retaining the biological activity of the translated peptides.

Further, the invention encompasses an isolated nucleic acid encoding a peptide having substantial homology to the peptides disclosed herein. Preferably, the nucleotide sequence of an isolated nucleic acid encoding a peptide of the invention is "substantially homologous", that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a peptide of the invention.

It is to be understood explicitly that the scope of the present invention encompasses homologs, analogs, variants, derivatives and salts, including shorter and longer peptides and polynucleotides, as well as peptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the biological activity of the original molecule. Specifically any active fragments of the active peptides as well as extensions, conjugates and mixtures are disclosed according to the principles of the present invention.

The invention should be construed to include any and all isolated nucleic acids which are homologous to the nucleic acids described and referenced herein, provided these homologous DNAs have the biological activity of the peptides disclosed herein.

The skilled artisan would understand that the nucleic acids of the invention encompass an RNA or a DNA sequence encoding a peptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell, supra, and Ausubel et al., supra. Procedures for the introduction of amino acid changes in a peptide or polypeptide by altering the DNA sequence encoding the polypeptide are well known in the art and are also described in these, and other, treatises.

The nucleic acids encoding the peptides of the invention can be incorporated into suitable vectors e.g. retroviral vectors. These vectors are well known in the art. The nucleic acids or the vectors containing them usefully can be transferred into a desired cell, which cell is preferably from a patient. Advantageously, the invention provides an off-the-shelf composition allowing rapid modification of a patient's own cells (or those of another mammal) to rapidly and easily produce modified cells having excellent cancer cell killing properties.

Vectors

In other related aspects, the invention includes an isolated nucleic acid encoding one or more of peptides having a sequence selected from the group consisting of SEQ ID NOs: 1-7.

In one embodiment, the invention includes a nucleic acid sequence encoding one or more peptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al., supra, and Ausubel et al., supra.

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058: and U.S. Pat. No. 6,326,193.

For expression of the desired nucleotide sequences of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue.

In order to assess the expression of the nucleotide sequences encoding the peptides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Vaccine

In one embodiment, the present invention is directed to a vaccine comprising a peptide of the invention. The vaccine of the invention can provide any combination of particular peptides for the particular prevention or treatment of the cancer of a subject that is in need of treatment.

The vaccine of the invention can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α).

In one embodiment, the present invention is directed to an anti-cancer vaccine. The vaccine can comprise one or more cancer antigens. The vaccine can prevent tumor growth. The vaccine can reduce tumor growth. The vaccine can prevent metastasis of tumor cells. Depending upon the cancer antigen, the vaccine can be targeted to treat breast cancer, liver cancer, prostate cancer, melanomas, blood cancers, head and neck cancer, glioblastoma, recurrent respiratory papillomatosis, anal cancer, cervical cancer, brain cancer, and the like.

In a particular embodiment, the vaccine can mediate clearance or prevent growth of tumor cells by inducing (1) humoral immunity via B cell responses to generate desirable antibodies; (2) increase cytotoxic T lymphocyte such as CD8' (CTL) to attack and kill tumor cells; (3) increase T helper cell responses; (4) and increase inflammatory responses via IFN-γ and TFN-α or preferably all of the aforementioned. The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%., 42%, 43%, 44%, 45%, 46%, 47%, 48%, 49%, 50%, 51%, 52%, 53%, 54%, 55%, 56%, 57%, 58%, 59%, and 60% after immunization.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine of the present invention can have features required of effective vaccines such as being safe so that the vaccine itself does not cause illness or death: being protective against illness; inducing neutralizing antibody; inducing protective T cell responses: and providing ease of administration, few side effects, biological stability, and low cost per dose. The vaccine can accomplish some or all of these features by containing the cancer antigen as discussed below.

Generation of a Loaded (Pulsed) Immune Cell

The present invention includes a cell that has been exposed or otherwise "pulsed" with an antigen or otherwise a peptide of the invention. For example, an APC, such as a DC, may become Ag-loaded in vitro, e.g., by culture ex vive in the presence of an antigen, or in vivo by exposure to an antigen.

A person skilled in the art would also readily understand that an APC can be "pulsed" in a manner that exposes the APC to an antigen for a time sufficient to promote presentation of that antigen on the surface of the APC. For example, an APC can be exposed to an antigen in the form of small peptide fragments, known as antigenic peptides, which are "pulsed" directly onto the outside of the APCs (Mehta-Damani et al., 1994); or APCs can be incubated with whole proteins or protein particles which are then ingested by the APCs. These whole proteins are digested into small peptide fragments by the APC and eventually carried to and presented on the APC surface (Cohen et al., 1994). Antigen in peptide form may be exposed to the cell by standard "pulsing" techniques described herein.

Without wishing to be bound by any particular theory, the antigen in the form of a foreign or an autoantigen is processed by the APC of the invention in order to retain the immunogenic form of the antigen. The immunogenic form of the antigen implies processing of the antigen through fragmentation to produce a form of the antigen that can be recognized by and stimulate immune cells, for example T cells. Preferably, such a foreign or an autoantigen is a protein which is processed into a peptide by the APC. The relevant peptide which is produced by the APC may be extracted and purified for use as an immunogenic composition. Peptides processed by the APC may also be used to induce tolerance to the proteins processed by the APC.

The antigen-loaded APC, otherwise known as a "pulsed APC" of the invention, is produced by exposure of the APC to an antigen either in vitro or in vivo. In the case where the APC is pulsed in vitro, the APC can be plated on a culture dish and exposed to an antigen in a sufficient amount and for a sufficient period of time to allow the antigen to bind to the APC. The amount and time necessary to achieve binding of the antigen to the APC may be determined by using methods known in the art or otherwise disclosed herein. Other methods known to those of skill in the art, for example immunoassays or binding assays, may be used to detect the presence of antigen on the APC following exposure to the antigen.

In a further embodiment of the invention, the APC may be transfected with a vector which allows for the expression of a specific protein by the APC. The protein which is expressed by the APC may then be processed and presented on the cell surface. The transfected APC may then be used as an immunogenic composition to produce an immune response to the protein encoded by the vector.

As discussed elsewhere herein, vectors may be prepared to include a specific polynucleotide which encodes and expresses a protein to which an immunogenic response is desired. Preferably, retroviral vectors are used to infect the cells. More preferably, adenoviral vectors are used to infect the cells.

In another embodiment, a vector may be targeted to an APC by modifying the viral vector to encode a protein or portions thereof that is recognized by a receptor on the APC, whereby occupation of the APC receptor by the vector will initiate endocytosis of the vector, allowing for processing and presentation of the antigen encoded by the nucleic acid of the viral vector. The nucleic acid which is delivered by the virus may be native to the virus, which when expressed on the APC encodes viral proteins which are then processed and presented on the MHC receptor of the APC.

As contemplated herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes). These methods are understood in the art and are described in published literature so as to enable one skilled in the art to perform these methods.

In another embodiment, a polynucleotide encoding an antigen can be cloned into an expression vector and the vector can be introduced into an APC to otherwise generate a loaded APC. Various types of vectors and methods of introducing nucleic acids into a cell are discussed in the available published literature. For example, the expression vector can be transferred into a host cell by physical, chemical or biological means. See, for example, Sambrook et al. (2012, Molecular Cloning: A Laboratory Manual, Cold Spring Harbor Laboratory, New York), and in Ausubel et al. (1997. Current Protocols in Molecular Biology, John Wiley & Sons, New York). It is readily understood that the introduction of the expression vector comprising a polynucleotide encoding an antigen yields a pulsed cell.

The present invention includes various methods for pulsing APCs including, but not limited to, loading APCs with whole antigen in the form of a protein, cDNA or mRNA. However, the invention should not be construed to be limited to the specific form of the antigen used for pulsing the APC. Rather, the invention encompasses other methods known in the art for generating an antigen loaded APC. Preferably, the APC is transfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of an APC with an mRNA provides an advantage over other antigen-loading techniques for generating a pulsed APC. For example, the ability to amplify RNA from a microscopic amount of tissue, i.e. tumor tissue, extends the use of the APC for vaccination to a large number of patients.

For an antigenic composition to be useful as a vaccine, the antigenic composition must induce an immune response to the antigen in a cell, tissue or mammal (e.g., a human). As used herein, an "immunological composition" may comprise an antigen (e.g., a peptide or polypeptide), a nucleic acid encoding an antigen (e.g., an antigen expression vector), or a cell expressing or presenting an antigen or cellular component. In particular embodiments the antigenic composition comprises or encodes all or part of any antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

A vaccine, as contemplated herein, may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. In addition, an antigenic composition can comprise a cellular component isolated from a biological sample. The antigenic composition isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with the antibody recognition of the epitopic sequence.

Antigen Presenting Cell Therapy

The invention encompasses a method of producing a population of APCs (e.g., dendritic cells; DCs) that present the peptides of the invention on their surface that may be subsequently used in therapy. Such a method may be carried out ex vivo on a sample of cells that have been obtained from a patient. The APCs produced in this way therefore form a pharmaceutical agent that can be used in the treatment or prevention of cancer. The cells should be accepted by the immune system of the individual because they derive from that individual. Delivery of cells that have been produced in this way to the individual from whom they were originally obtained, thus forms a therapeutic embodiment of the invention.

DCs are derived from pluripotent monocytes that serve as antigen-presenting cells (APCs). DCs are ubiquitous in peripheral tissues, where they are prepared to capture antigens. Upon antigen capture, DCs process the antigen into small peptides and move towards secondary lymphoid organs. It is within the lymphoid organs that DCs present antigen peptides to naive T cells, thereby initiating a cascade of signals that polarizes T cell differentiation. Upon exposure, DCs present antigen molecules bound to either MHC class I or class II binding peptides and activate CD8 or CD4$^+$ T cells, respectively (Steinman, 1991, Annu. Rev. Immunol. 9:271-296; Banchereau et al., 1998, Nature 392,245-252; Steinman, et al., 2007, Nature 449:419-426: Ginhoux et al., 2007, J. Exp. Med. 204:3133-3146; Banerjee et al., 2006, Blood 108:2655-2661: Sallusto et al., 1999, J. Exp. Med. 189:611-614; Reid et al., 2000, Curr. Opin. Immunol. 12:114-121; Bykovskaia et al., 1999, J. Leukoc. Biol. 66:659-666; Clark et al., 2000, Microbes Infect. 2:257-272).

DCs are responsible for the induction, coordination and regulation of the adaptive immune response and also serve to orchestrate communication between effectors of the innate arm and the adaptive arm of the immune system. These features have made DCs strong candidates for immunotherapy. DCs have a unique capacity to sample the environment through macropinocytosis and receptor-mediated endocytosis (Gemer et al., 2008, J. Immunol. 181:155-164; Stoitzner et al., 2008, Cancer Immunol. Immunother 57:1665-1673: Lanzevecchia A., 1996, Curr. Opin. Immunol. 8:348-354; Delamarre et al., 2005, Science, 307(5715): 1630-1634).

DCs also require maturation signals to enhance their antigen-presenting capacity. DCs upregulate the expression of surface molecules, such as CD80 and CD86 (also known as second signal molecules) by providing additional maturation signals, such as TNF-$\alpha$, CD40L or calcium signaling agents (Czemiecki et al., 1997. J. Immunol. 159:3823-3837; Bedrosian et al. 2000, J. Immunother. 23:311-320; Mailliard et al., 2004, Cancer Res. 64,5934-5937; Brossart et al., 1998, Blood 92:4238-4247: Jin et al., 2004, Hum. Immunol. 65:93-103). It has been established that a mixture of cytokines, including TNF-$\alpha$, IL-1$\beta$, IL-6 and prostaglandin E2 (PGE2), have the ability to mature DC (Jonuleit, et al., 2000, Arch. Derm. Res. 292:325-332). DCs can also be matured with calcium ionophore prior to being pulsed with antigen.

In addition to pathogen-recognition receptors, such as PKR and MDA-5 (Kalali et al., 2008, J. Immunol. 181: 2694-2704: Nallagatla et al., 2008, RNA Biol. 5(3): 140-144), DCs also contain a series of receptors, known as Toll-like receptors (TLRs), that are also capable of sensing danger from pathogens. When these TLRs are triggered, a series of activational changes are induced in DCs, which lead to maturation and signaling of T cells (Boullart et al. 2008, Cancer Immunol. Immunother. 57(11): 1589-1597; Kaisho et al., 2003, Curr. Mol. Med. 3(4):373-385; Pulendran et al., 2001, Science 293(5528):253-256; Napolitani et al., 2005, Nat. Immunol. 6(8):769-776). DCs can activate and extend the various arms of the cell-mediated response, such as natural killer $\gamma$-$\delta$ T and $\alpha$-$\beta$ T cells and, once activated, DCs retain their immunizing capacity (Steinman, 1991, Annu. Rev. Immunol. 9:271-296: Banchereau et al., 1998, Nature 392:245-252; Reid et al., 2000, Curr. Opin. Immunol. 12:114-121: Bykovskaia et al., 1999, J. Leukoc. Biol. 66:659-666; Clark et al., 2000, Microbes Infect. 2:257-272).

The present invention also provides methods of inducing antigen presenting cells (APCs) using one or more peptides of the invention. The APCs can be induced by inducing dendritic cells from the peripheral blood monocytes and then contacting (stimulating) them with one or more peptides of this invention in vitro, ex vivo or in vivo. When peptides of the present invention are administered to the mammal in need thereof, APCs that have the peptides of this invention immobilized to them are induced in the body of the mammal. Alternatively, after immobilizing the peptides of this invention to the APCs, the cells can be administered to the subject as a vaccine. For example, the ex vivo administration may include the steps of collecting APCs from a mammal, and contacting the APCs with a peptide of the present invention.

The present invention also provides APCs presenting complexes formed between HLA antigens and one or more peptides of this invention. The APCs, obtained through contact with the peptides of this invention or the nucleotides encoding such peptides, are preferably derived from subjects who are the target of treatment and/or prevention, and can be administered as vaccines, alone or in combination with other drugs, including the peptides, exosomes, or T cells of the present invention.

The present invention provides compositions and methods for stimulating APC, preferably DCs, in the context of immunotherapy to stimulate the immune response in a mammal. DCs can be manipulated by stimulating them with a peptide or combination of peptides of the invention and causing the DCs to mature so that they stimulate anti-tumor immunity in a mammal in need thereof.

In one embodiment, the invention includes a method for inducing a T cell response in a mammal. The method comprising administering an APC, such as a DC, wherein the APC has been activated by contacting the APC with a peptide or combination of peptides of the invention thereby generating a peptide-loaded APC.

In one embodiment, the invention relates to novel APCs produced and methods for their use to, inter alia, expand a desired T cell, to activate T cells, to expand specific T cell, as well as numerous therapeutic uses relating to expansion and stimulation of T cells using the peptide-load APC and peptides of the invention. In some instances, the OCT4 stimulated DCs can be used to expand peptide-specific T cells.

The present invention relates to the discovery that a DC contacted with a peptide or combination of peptides of the invention can be used to induce expansion of peptide-specific T cells. A skilled artisan would recognize that the DCs contacted with the peptides of the invention are considered primed or otherwise peptide-loaded. The peptide-loaded DCs of the invention are useful for eliciting an immune response against a desired antigen, for example HER3. Accordingly, the peptide-load DCs of the invention can be used to treat a disease associated with unregulated expression of HER3.

Methods for Treating a Disease

The present invention also encompasses methods of treatment and/or prevention of a disease caused by pathogenic microorganisms, autoimmune disorder and/or a hyperproliferative disease.

Diseases that may be treated or prevented by use of the present invention include diseases caused by viruses, bacteria, yeast, parasites, protozoa, cancer cells and the like. The pharmaceutical composition of the present invention may be used as a generalized immune enhancer (DC activating composition or system) and as such has utility in treating diseases. Exemplary diseases that can be treated and/or prevented utilizing the pharmaceutical composition of the present invention include, but are not limited to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc., or infections of parasitic etiology such as malaria, trypanosomiasis, leishmaniasis, trichomoniasis, amoebiasis, etc.

Preneoplastic or hyperplastic states that may be treated or prevented using the pharmaceutical composition of the present invention (transduced DCs, expression vector, expression construct, etc.) of the present invention include but are not limited to preneoplastic or hyperplastic states such as colon polyps, Crohn's disease, ulcerative colitis, breast lesions and the like.

Cancers that may be treated using the composition of the present invention of the present invention include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, gastrointestinal cancer, brain cancer, bladder cancer, cervical cancer and the like.

Other hyperproliferative diseases that may be treated using DC activation system of the present invention include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

Autoimmune disorders that may be treated using the composition of the present invention include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, and extracorporeal circulation: viral, bacterial, fungal, parasitic, protozoal, and helminthic infections; and trauma.

In the method of treatment, the administration of the composition of the invention may be for either "prophylactic" or "therapeutic" purpose. When provided prophylactically, the composition of the present invention is provided in advance of any symptom, although in particular embodiments the vaccine is provided following the onset of one or more symptoms to prevent further symptoms from developing or to prevent present symptoms from becoming worse. The prophylactic administration of composition serves to prevent or ameliorate any subsequent infection or disease. When provided therapeutically, the pharmaceutical composition is provided at or after the onset of a symptom of infection or disease. Thus, the present invention may be provided either prior to the anticipated exposure to a disease-causing agent or disease state or after the initiation of the infection or disease.

An effective amount of the composition would be the amount that achieves this selected result of enhancing the immune response, and such an amount could be determined as a matter of routine by a person skilled in the art. For example, an effective amount of for treating an immune system deficiency against cancer or pathogen could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Vaccine Formulations

The present invention further includes vaccine formulations suitable for use in immunotherapy. In certain embodiments, vaccine formulations are used for the prevention and/or treatment of a disease, such as cancer and infectious diseases. In one embodiment, the administration to a patient of a vaccine in accordance with the present invention for the prevention and/or treatment of cancer can take place before or after a surgical procedure to remove the cancer, before or after a chemotherapeutic procedure for the treatment of cancer, and before or after radiation therapy for the treatment of cancer and any combination thereof. In other embodiments, the vaccine formulations may be administrated to a patient in conjunction or combination with another composition or pharmaceutical product. It should be appreciated that the present invention can also be used to prevent cancer in individuals without cancer, but who might be at risk of developing cancer.

The administration of a cancer vaccine prepared in accordance with the present invention, is broadly applicable to the prevention or treatment of cancer, determined in part by the selection of antigens forming part of the cancer vaccine. Cancers that can be suitably treated in accordance with the practices of the present invention include, without limitation, cancers of the lung, breast, ovary, cervix, colon, head and neck, pancreas, prostate, stomach, bladder, kidney, bone, liver, esophagus, brain, testicle, uterus and the various leukemias and lymphomas.

In one embodiment, vaccines in accordance with this invention can be derived from the tumor or cancer cells to be treated. For example, in the treatment of lung cancer, the lung cancer cells would be treated as described hereinabove to produce a lung cancer vaccine. Similarly, breast cancer vaccine, colon cancer vaccine, pancreas cancer vaccine, stomach cancer vaccine, bladder cancer vaccine, kidney cancer vaccine and the like, would be produced and employed as immunotherapeutic agents in accordance with the practices for the prevention and/or treatment of the tumor or cancer cell from which the vaccine was produced.

In another embodiment, vaccines in accordance with the present invention could, as stated, also be prepared to treat various infectious diseases which affect mammals, by collecting the relevant antigens shed into a culture medium by the pathogen. As there is heterogenecity in the type of immunogenic and protective antigens expressed by different varieties of organisms causing the same disease, polyvalent vaccines can be prepared by preparing the vaccine from a pool of organisms expressing the different antigens of importance.

In another embodiment of the present invention, the vaccine can be administered by intranodal injection into groin nodes. Alternatively, and depending on the vaccine target, the vaccine can be intradermally or subcutaneously administered to the extremities, arms and legs, of the patients being treated. Although this approach is generally satisfactory for melanoma and other cancers, including the prevention or treatment of infectious diseases, other routes of administration, such as intramuscularly or into the blood stream may also be used.

Additionally, the vaccine can be given together with adjuvants and/or immuno-modulators to boost the activity of the vaccine and the patient's response. Such adjuvants and/or immuno-modulators are understood by those skilled in the art, and are readily described in available published literature.

As contemplated herein, and depending on the type of vaccine being generated, the production of vaccine can, if desired, be scaled up by culturing cells in bioreactors or fermentors or other such vessels or devices suitable for the growing of cells in bulk. In such apparatus, the culture medium would be collected regularly, frequently or continuously to recover therefrom any materials or antigens before such materials or antigens are degraded in the culture medium.

If desired, devices or compositions containing the vaccine or antigens produced and recovered, in accordance with the present invention, and suitable for sustained or intermittent release could be, in effect, implanted in the body or topically applied thereto for a relatively slow or timed release of such materials into the body.

Other steps in vaccine preparation can be individualized to satisfy the requirements of particular vaccines. Such additional steps will be understood by those skilled in the art. For example, certain collected antigenic materials may be concentrated and in some cases treated with detergent and ultracentrifuged to remove transplantation alloantigens.

HER3 Expression as a Biomarker for Diagnosis and Treatment of Disease

In another embodiment HER3 expression can serve as a biomarker for occult invasive disease in patients with Barrett's esophagus and high-grade dysplasia (HGD). Additionally contemplated herein are therapeutics for targeting HER3 or CMET that may afford secondary prevention of gastroesophageal carcinoma in some patients.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Creating Peptide Vaccines Against Other Receptor Tyrosine Kinases ("RTKs") that Cause Breast Cancer and Other Solid Cancers Experiments were designed to develop alternative therapies against patients designated as BRCA mutation carriers. That is, there is an unmet need for younger patients genetically at risk for breast cancer who are seeking alternatives to bilateral mastectomy.

Women with the breast cancer gene mutations BRCA1/BRCA2 have a 70% lifetime risk of developing breast cancer, and BRCA1 mutation carriers often develop triple negative breast cancer. Experiments were designed to develop vaccines for this group and evaluate their safety in an immune-inducing trial, which is the first attempt ever at vaccination for primary prevention of breast cancer. BRCA2 mutation carriers will also be included to see if estrogen receptor$^{-positive}$ breast cancer can be prevented using the multivalent vaccine of the invention.

Experiments were designed to study RTK expression in breast cancers and DCIS from BRCA mutation carriers. It was observed that tumors from the BRCA mutation carriers frequently over-expressed the c-MET oncogene and HER3 early on while the tumors from non-mutation or sporadic patients expressed HER2 and HER3. This is important because targets for tumor immunotherapy that can be used to develop vaccines for sporadic and BRCA mutation carriers it is now known based on the disclosure presented herein. This is the first distinguishing feature that can be targeted using immune response for prevention. Accordingly, the invention includes compositions and methods for developing vaccines and uses thereof for prevention as an alternative to bilateral mastectomies.

Creating Peptide Vaccines

The HER family consists of four related signaling molecules-HER1, HER2, HER3, and HER4—that are involved in a variety of cancers. It is known that over-expression of HER2 is found in 20% to 30% of breast cancers. The results presented herein demonstrate that other HER family members are involved in both early and invasive breast cancer, as well as other cancers. For example, HER1 is expressed on a small number of breast cancers, generally those that are triple negative, c-MET is a growth factor receptor involved in recurrence of many cancers that activates HER3. HER3 is over-expressed in colon, prostate, breast and melanoma. HER3 is expressed in a large number of DCIS lesions and breast cancers. HER3 can be detected in the residual DCIS at the time of surgery in some patients who received a HER2 vaccine. As a result of these findings, the potential to target these molecules in addition to HER2 in breast cancer is believed to be beneficial.

Immunogenic peptides from HER3 have been identified (FIGS. 1 and 2) as follows:

```
p11-13 (Peptide 51-75):
                             (SEQ ID NO: 1)
KLYERCEVVMGNLEIVLTGHNADLSFLQW;

p81-83 (Peptide 401-425):
                             (SEQ ID NO: 2)
SWPPHMHNFSVFSNLTTIGGRSLYN;

p84-86 (Peptide 416-440):
                             (SEQ ID NO: 3)
TTIGGRSLYNRGFSLLIMKNLNVTS;

p12 (Peptide 56-70):
                             (SEQ ID NO: 4)
CEVVMGNLEIVLTGH;

p81 (Peptide 401-415):
                             (SEQ ID NO: 5)
SWPPHMHNFSVFSNL;

p84 (Peptide 416-430):
                             (SEQ ID NO: 6)
TTIGGRSLYNRGFSL;
and p91 (Peptide 451-465):
                             (SEQ ID NO: 7)
AGRIYISANRQLCYH.
```

The results presented herein demonstrate that these peptides can activate CD4 T cells across many patients. The peptides can be used to pulse dendritic cells and educate T cells to recognize HER3. HER3 is expressed in triple-negative breast cancer and can impart resistance to anti-estrogen in ER$^{-positive}$ breast cancers. HER3 is also expressed in other cancers, including melanoma, lung, colon, prostate cancer, and metastatic brain tumors. Without wishing to be bound by any particular theory, peptides from the intracellular part of the molecule may also be advantageous.

Based on the disclosure presented herein, immunogenic peptides for HER1 and the c-MET RTK molecules can be screened and identified based on the procedure that identified immunogenic peptides for HER3. The immunogenic peptides of the invention can be used to prepare a multivalent preventive vaccine for breast cancer as well as other cancers.

The results presented herein show the identification of the role of HER2's sister proteins in breast cancer. These sister proteins can be effectively targeted and vaccines for other solid tumors can be developed. Peptides that can be used to target HER1 and HER3 have been developed. In DCIS specifically, specific anti-HER1, HER2, and HER3 responses in patients before and after vaccination have been identified, which provides support for the development of a multivalent vaccine that can be used to prevent early cancer or treat women who have DCIS. The compositions of the invention is useful to treat other cancers including but not limited to colon cancer, melanoma., brain tumors, lung cancer, ovarian cancer, and other tumors.

Melanoma

Melanoma is an aggressive skin cancer that can be deadly if not caught early. Experiments were conducted in mice using a standard dendritic cell vaccine wherein the dendritic cell was engineered to exhibit a mutated protein (BRAF) that causes about 70% of melanomas. Vaccination with these dendritic cells protected the mice from challenge with melanoma cells, demonstrating that it is possible to develop vaccines for melanoma. Without wishing to be bound by any particular theory, combinations of BRAF and HER3 targeting may be useful for treating melanomas as well as other cancers including but not limited to solid cancers, such as colon, pancreatic, and lung cancers, and other gastrointestinal tumors.

In addition, it has been shown that melanoma tumors use B cells to escape immune surveillance, and therefore it is believed that eliminating certain B cells can improve therapy. Experiments can be designed to assess whether altering the tumor microenvironment to a Th1-type response can help to prevent escape.

In some instances, the vaccine of the invention can be used to treat melanoma that has spread. In some instances, the invention provides therapies to eliminate remaining cells that often become resistant to drug therapy.

Example 2: Novel Strategy to Identify MHC Class II-Promiscuous CD4$^+$ Peptides from Tumor Antigens for Utilization in Vaccination Although cytotoxic CD8+T lymphocytes (CTL) were historically considered primary effectors of antitumor immunity, solely boosting CTL responses with CD8+ vaccines in various tumor types has yielded unpredictable clinical results, possibly because CTLs function suboptimally without adequate CD4+T-lymphocyte help. CD4+T-helper type 1 (Th1) cells secrete INF-γ/TNF-α, inducing tumor senescence and apoptosis. As such, successful incorporation of CD4+ epitopes into cancer vaccine construction and generation of durable antigen-specific CD4+ immunity remains a challenge. Using the extracellular domain (ECD) of HER3 as a candidate "oncodriver" tumor antigen, experiments were performed to identify immunogenic HER3

CD4+ peptides that demonstrate Class II promiscuity and generate anti-HER3 CD4+ immunity for inclusion in a vaccine construct.

The materials and methods employed in these experiments are now described.

Materials and Methods

Experiments were designed to identify immunogenic Class II-promiscuous HER3 CD4+ peptides using the ECD of HER3 as a tumor antigen in order to generate anti-HER3 Th1 cellular immunity.

Protocol Overview

A library of 15-mer long peptides that overlap by 5 amino acids was created from the HER3 ECD. These peptides were pulsed onto monocyte-derived DCs from donors and were matured to type 1-polarized (DC1; IL-12-secreting) phenotype. The DC1s were harvested and co-cultured with purified CD4+ T cells from subjects who had known anti-HER3 Th1 responses from our DCIS vaccine study. Large pools of 10 peptides were used and the identification process was progressively narrowed down to single reactive epitopes as measured by interferon gamma (IFN-γ) secretion of the CD4+ T cells. Upon screening 5-6 subjects, 4 peptides were identified that seemed to react across most donors i.e., HER3$_{56-70}$ (SEQ ID NO: 4), HER3$_{401-415}$ (SEQ ID NO: 5), HER3$_{416-430}$ (SEQ ID NO: 6), and HER3$_{451-465}$ (SEQ ID NO: 7). Subjects with no evidence of reactivity to CD4+ T cell recognition of HER3 extracellular domain were identified and their DC1s were pulsed with the four HER3 peptides and the pulsed DC1s were cultured with CD4 T cells for a week and then tested for reactivity against HER2 peptide and reaction to extracellular HER3 protein. In all cases, at least 1 peptide led to recognition of both the peptide pulsed on monocytes and the whole HER3 protein suggesting that primary sensitization had taken place ex vivo. It was also shown that healthy donors can react to these peptides and in triple negative breast cancer patients where there is a loss of anti-HER3 Th1 responses. See, also, Gala, K., et al., Clin. Cancer Res 2014; 20: 1410-1416 and Datta, J., et al., "Progressive Loss of Anti-HER2 CD4+T-helper Type 1 Response in Breast Tumorigenesis and the Potential for Immune Restoration". OncoImmunology (in press).

Figure 19:
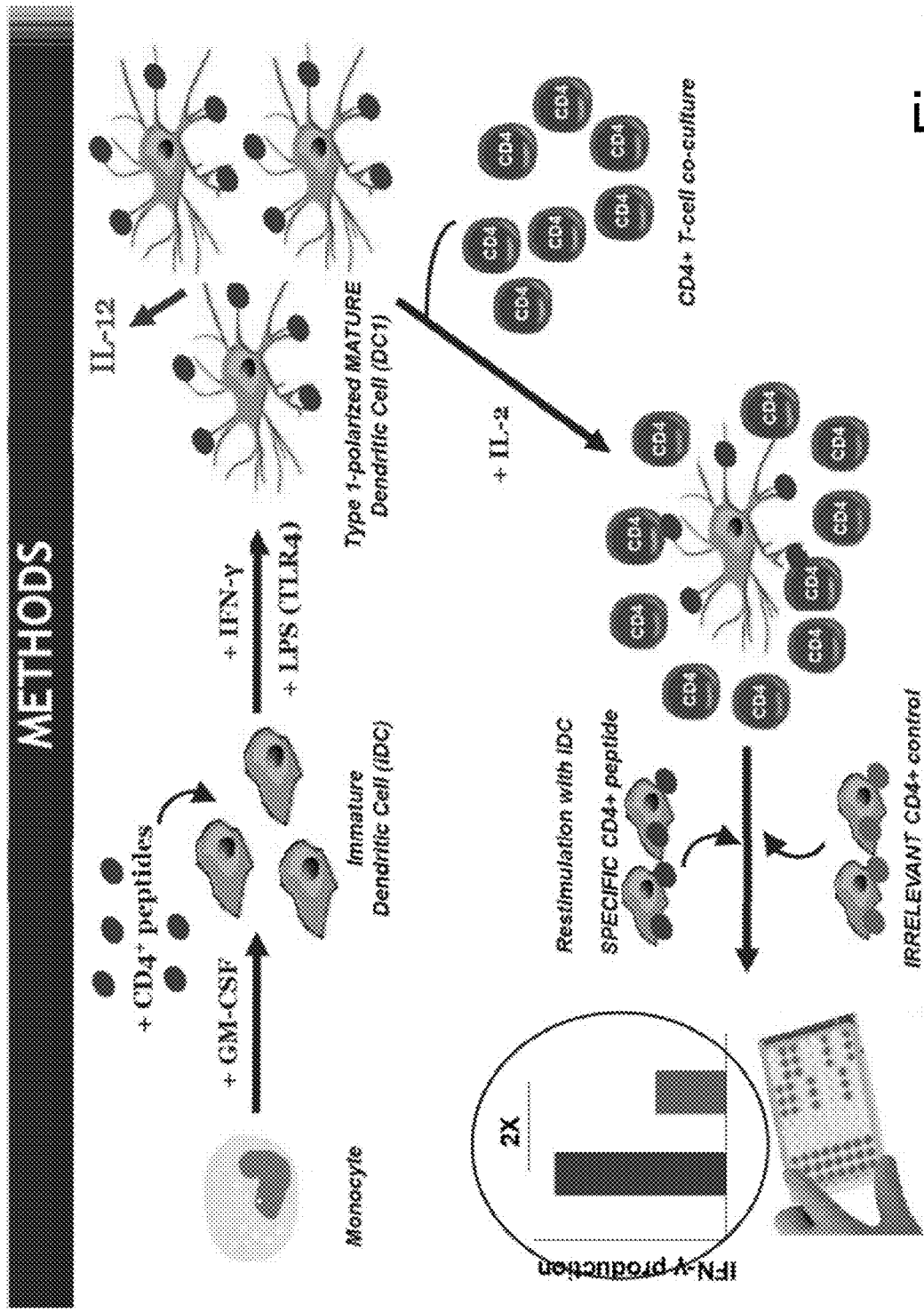
FIG. 19 shows methods for identification of immunogenic Class II-promiscuous HER3 CD4+ peptides using the ECD of HER3 as a tumor antigen in order to generate anti-HER3 Th1 cellular immunity.

Protocol Highlights as Further Illustrated in FIG. 19:
A library comprising 123 overlapping 15 amino acid-long peptide fragments that overlapped by 5 amino acids was generated from the HER3 extracellular domain (ECD).
Autologous monocyte-derived dendritic cells (DC) from donors were rapidly matured to a type 1-polarized (DC1→IL-12 secreting) phenotype via GM-CSF, IFN-γ and LPS, and pulsed with relevant peptides (e.g., HER3 ECD or HER3 CD4' peptides, where indicated). DC1 polarize Th1 responses via elaboration of IL-12.
Harvested DC1s were allosensitized with purified CD4+ T-cells in 8-10 day co-cultures.
Sensitized CD4+ T-cells (a large fraction of which are expected to become antigen-specific) were restimulated against immature DCs (iDC) that were pulsed with a specific CD4+ peptide of interest (e.g., HER3 library peptide clusters) or irrelevant class II peptide control.
The supernatant from these co-cultures were then harvested. Th responses, measured by IFN-γ ELISA, were considered antigen-specific if IFN-γ production was at least twice that of irrelevant control.
HLA-DR, DP, DQ typing was performed on donors by the Clinical Immunology laboratory at the Hospital of the University of Pennsylvania in order to assess MHC class II promiscuity of CD4' Th1 responses.

A library comprising 123 overlapping 15 amino acid-long peptide fragments was generated from the HER3-ECD. Autologous monocyte-derived DCs from donors were matured to DC s, and pulsed with HER3-ECD. Harvested DC1s were co-cultured with purified CD4 T cells. After 10 days, sensitized CD4 T cells were restimulated against immature DCs (iDC) that were pulsed with HER3 library peptide clusters or irrelevant CD4 control peptide1. Th1 responses, measured by IFN-γ ELISA, were considered antigen-specific if IFN-γ production was at least twice that of irrelevant control.

Experiments were performed in a 3-step process: 1) breast cancer patients with known anti-HER3 ECD reactivity following HER2-pulsed DC i vaccine were obtained in order to identify immunogenic CD4+ peptides; 2) the immunogenicity of these peptides were confirmed in the same patients by a process of "reverse" sensitization; 3) patients with known anti-HER3 ECD non-reactivity following vaccination were obtained and used to identify CD4+ peptides to see if the cells were sensitized to the native HER3 ECD, thus overcoming/abrogating self-antigen (i.e., HER3) tolerance.

The results of the experiments are now described.

Figure 2:
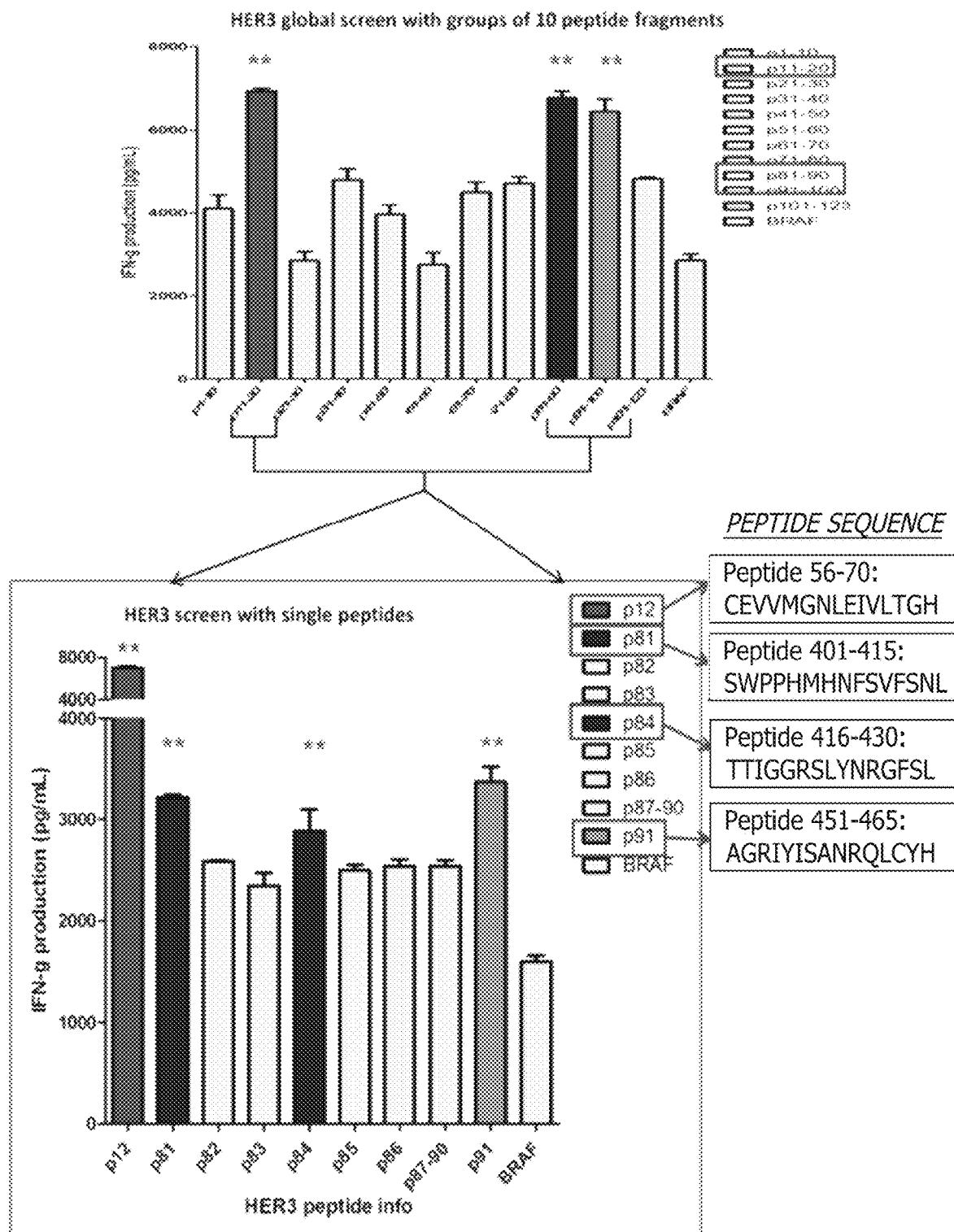
FIG. 2 shows a HER3 global screen with groups of 10 peptide fragments.
Figure 3:
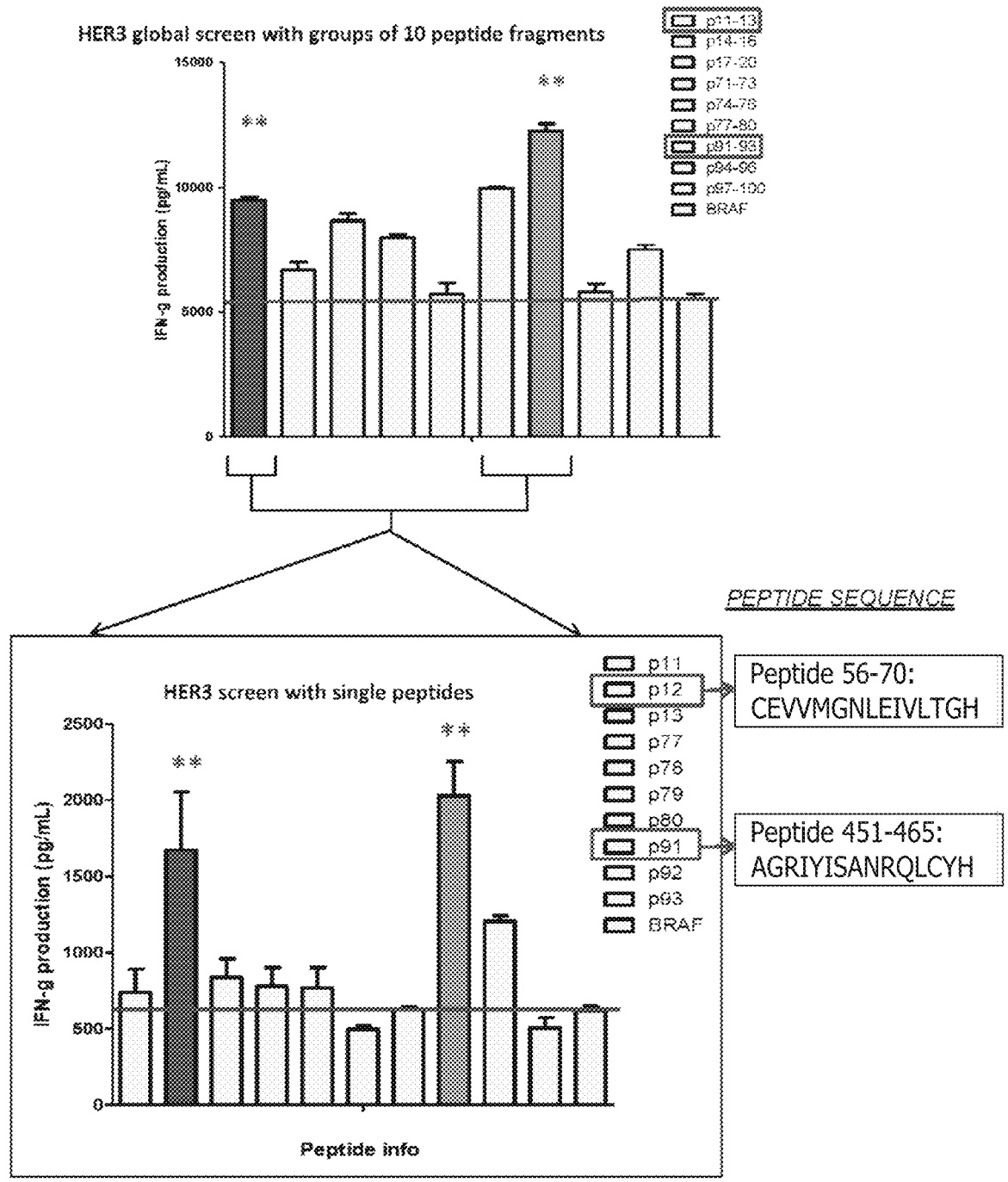
FIG. 3 shows a HER3 global screen with groups of 10 peptide fragments.
Figure 4:
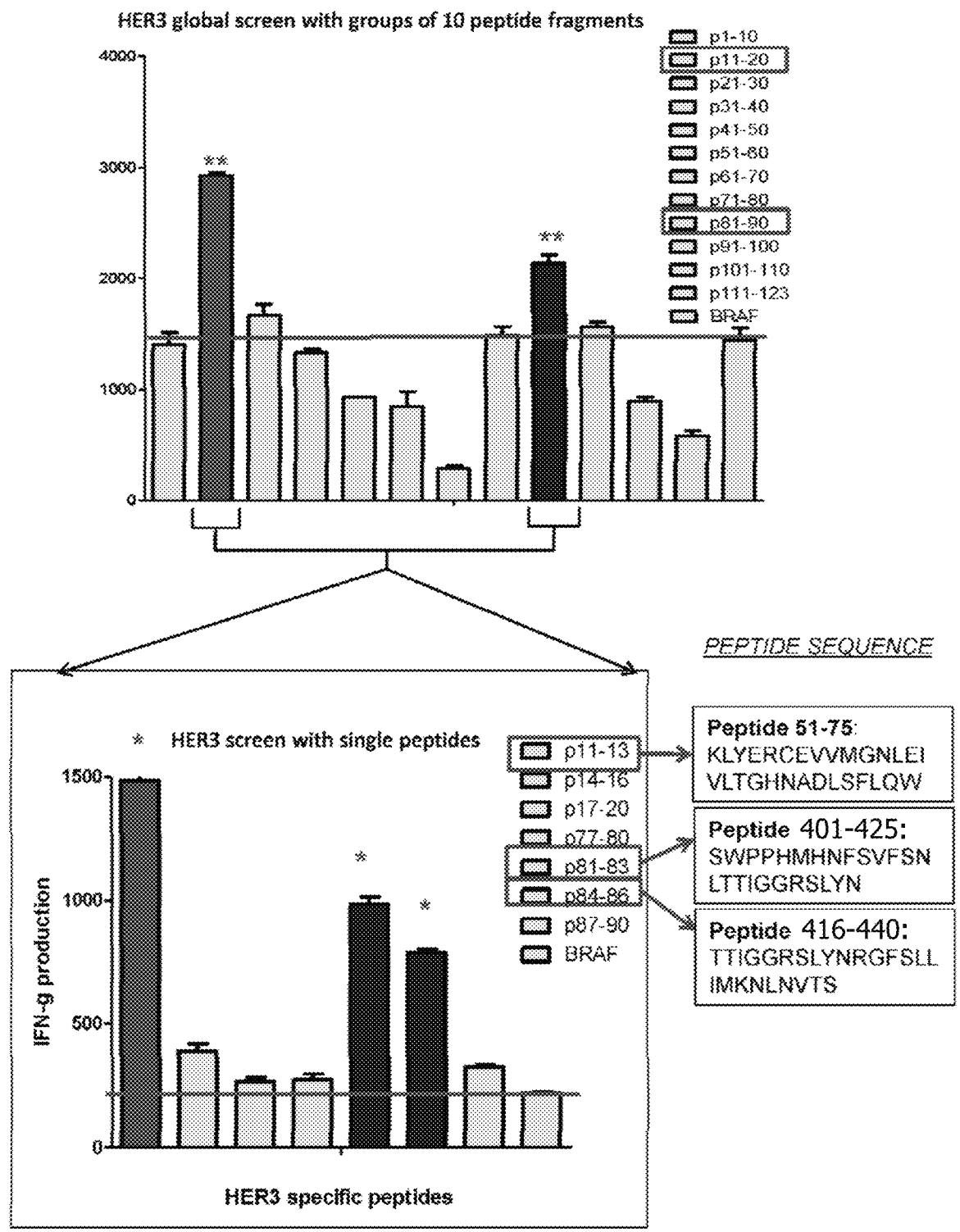
FIG. 4 shows a HER3 global screen with groups of 10 peptide fragments.
Figure 5:
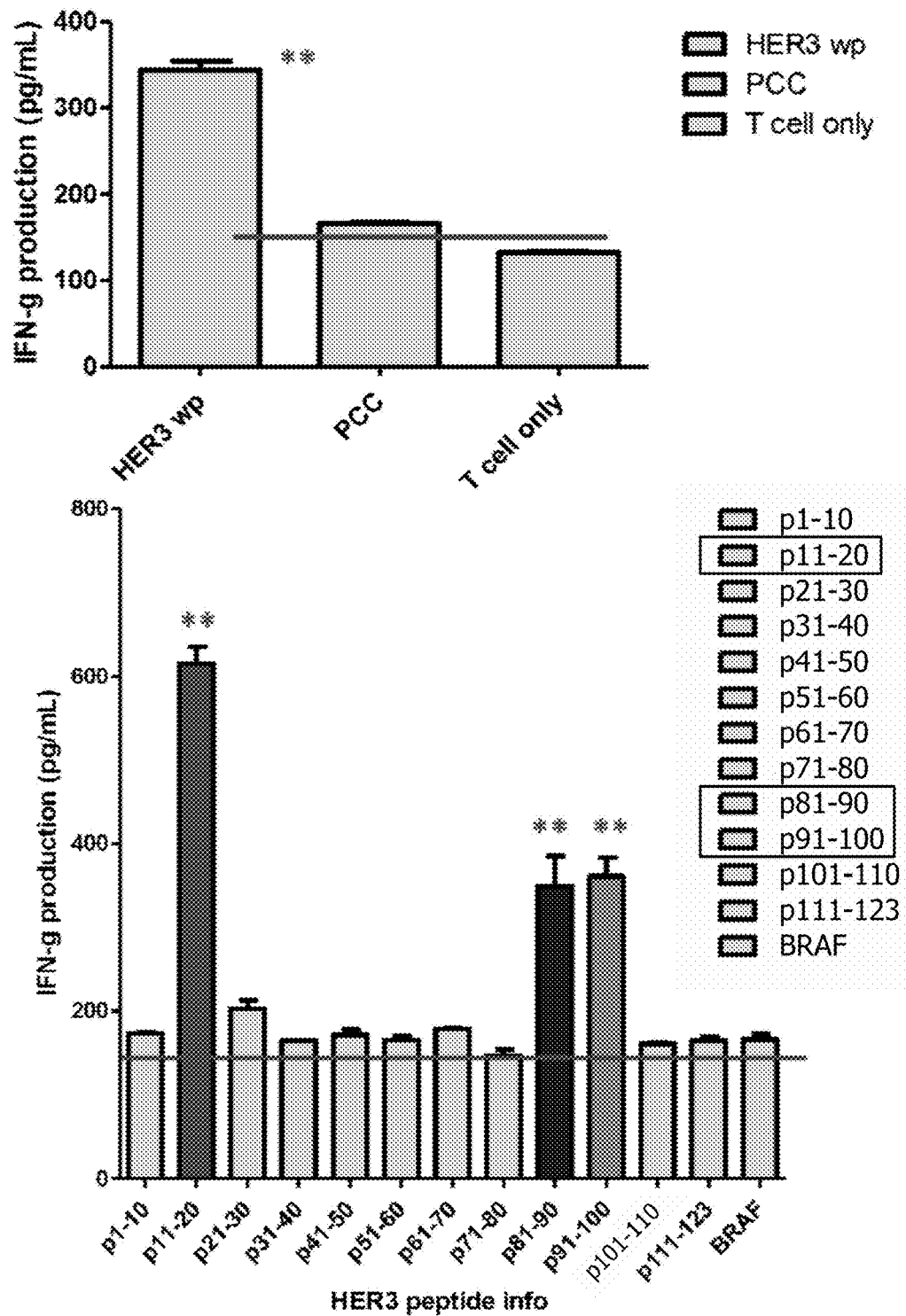
FIG. 5 shows IFN-γ production from different HER3 peptides.
Figure 6:
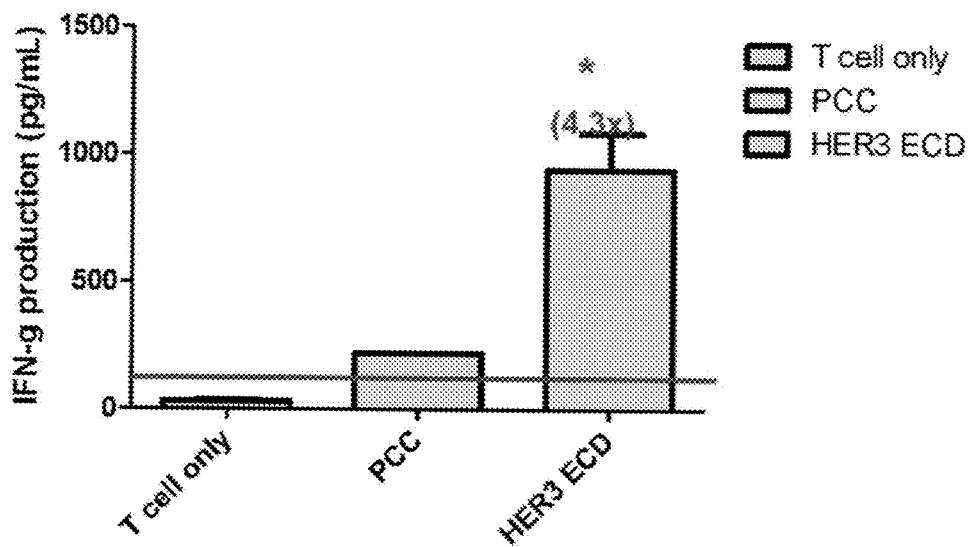
FIG. 6 shows IFN-γ production from different HER3 peptides.
Figure 6:
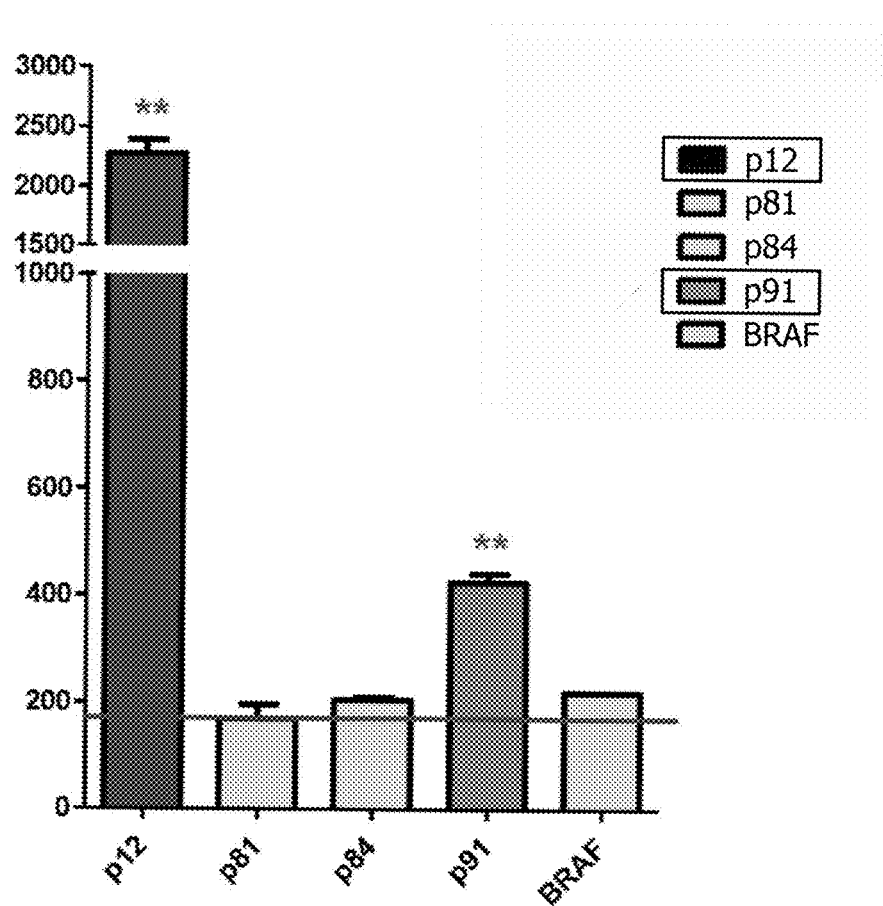
Figure 7:
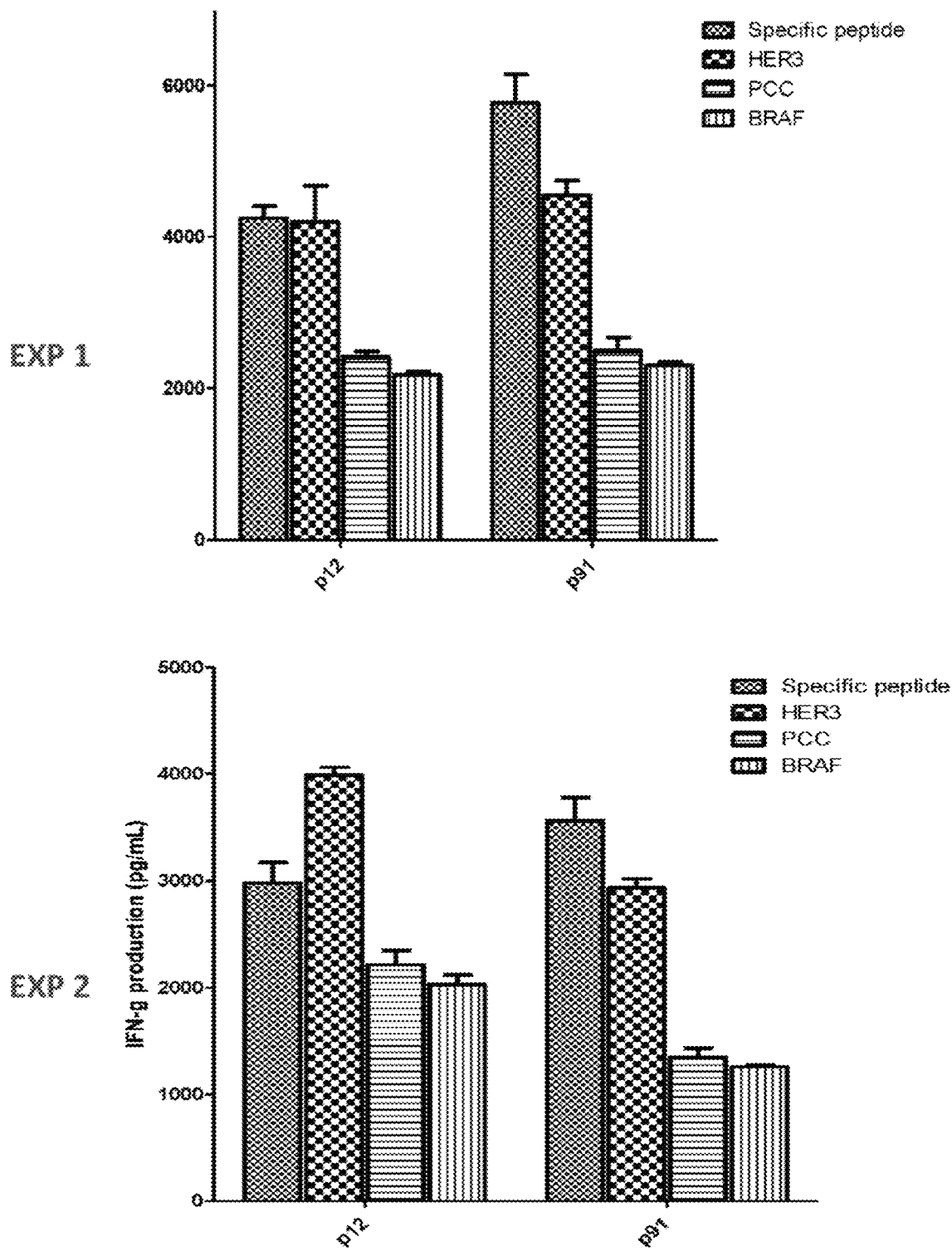
FIG. 7 shows IFN-γ production from a "REVERSE" screen, starting with previously identified peptides, sensitizing to peptides and HER3 extracellular domain.
Figure 8:
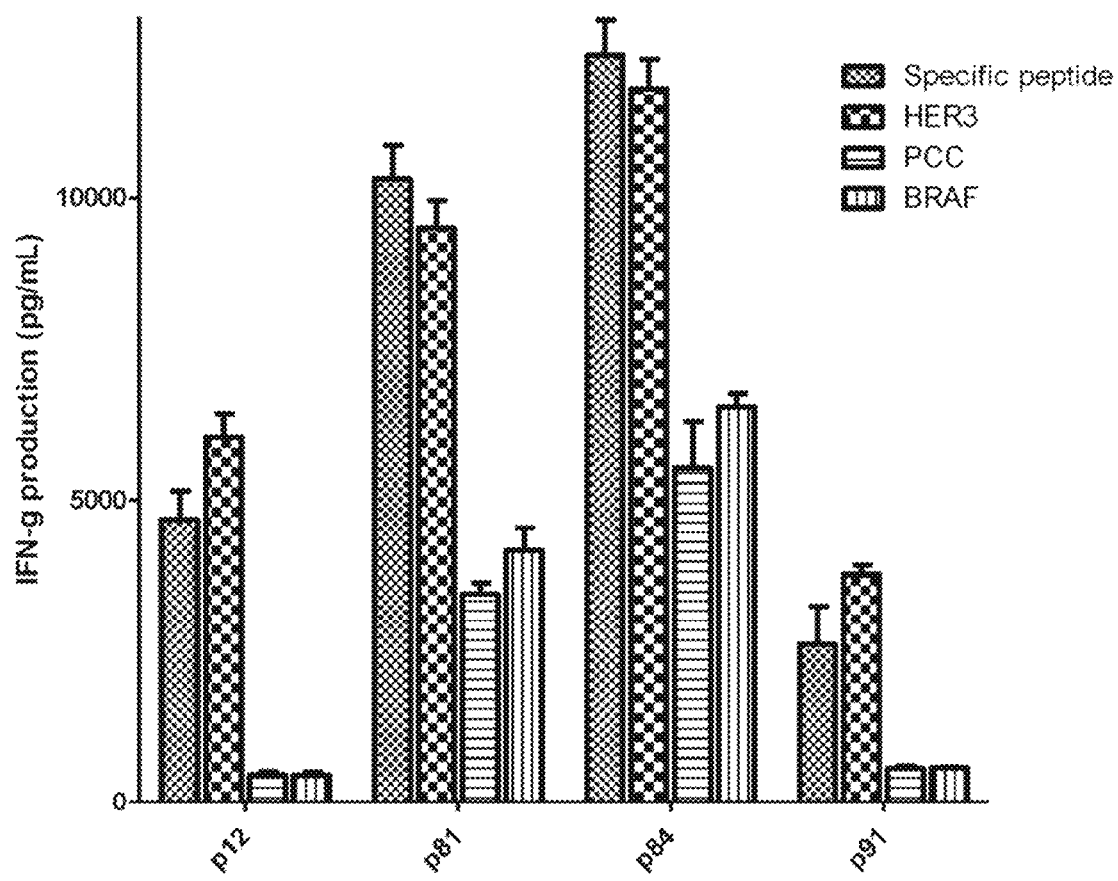
FIG. 8 shows IFN-γ production from a "REVERSE" screen, starting with previously identified peptides, sensitizing to peptides and HER3 extracellular domain.
Figure 9:
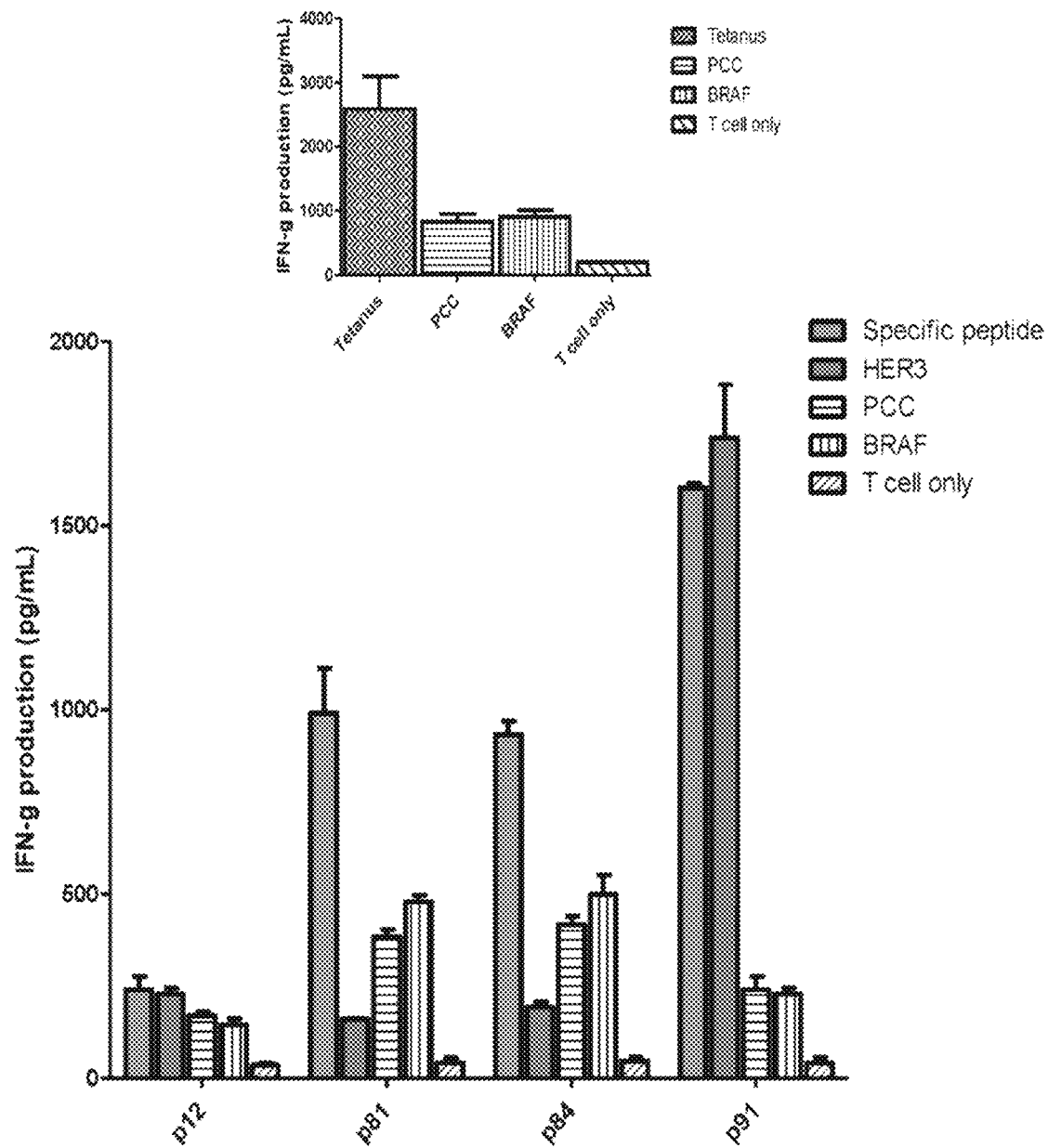
FIG. 9 shows IFN-γ production from a "REVERSE" screen in a patient not previously sensitized with HER extracellular domain, starting with peptides, sensitizing to peptides and HER3 extracellular domain.
Figure 10:
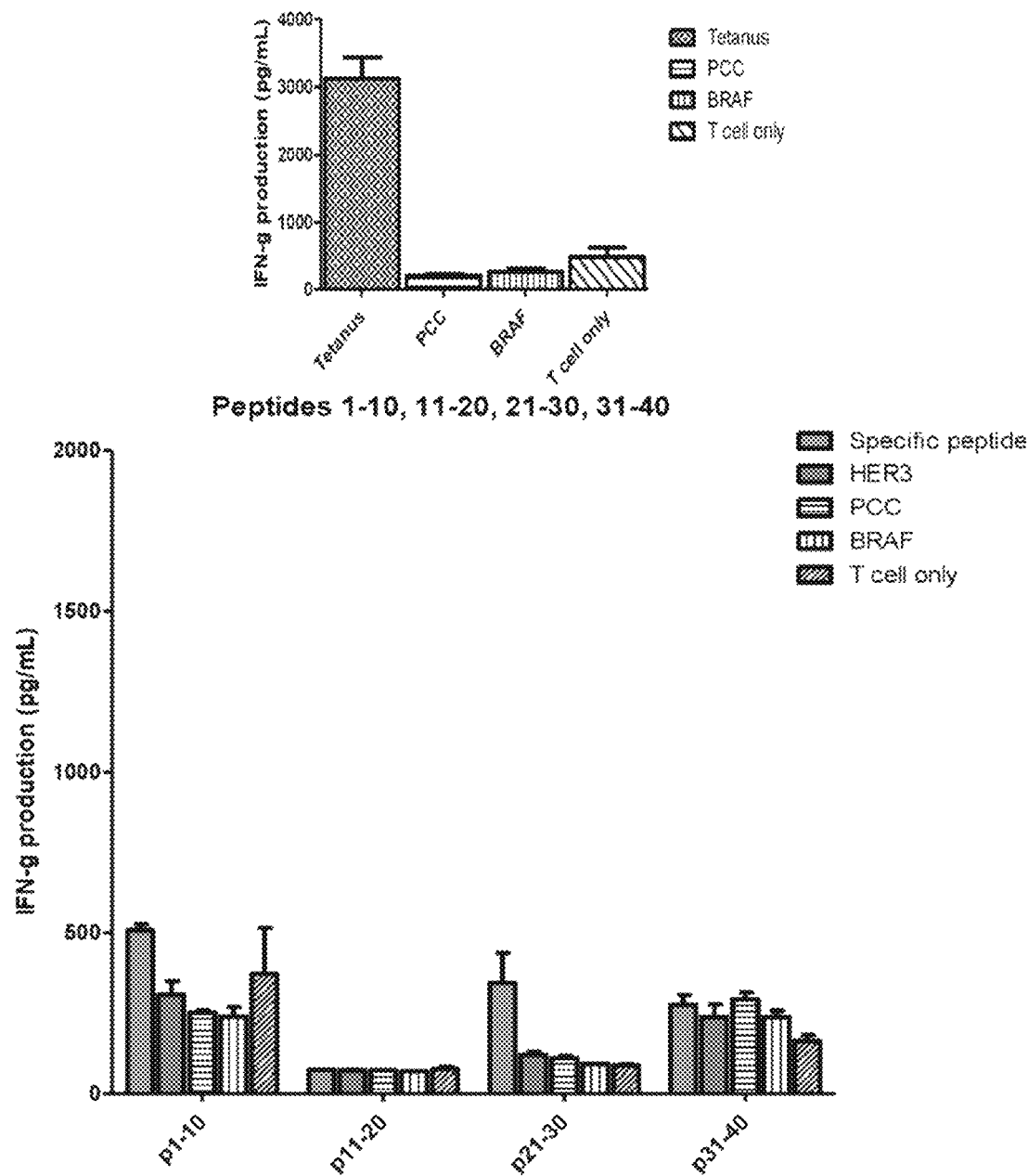
FIG. 10 shows IFN-γ production from a "REVERSE" screen in a patient not previously sensitized with HER extracellular domain, starting with whole peptide library, sensitizing to peptides and HER3 extracellular domain.
Figure 11:
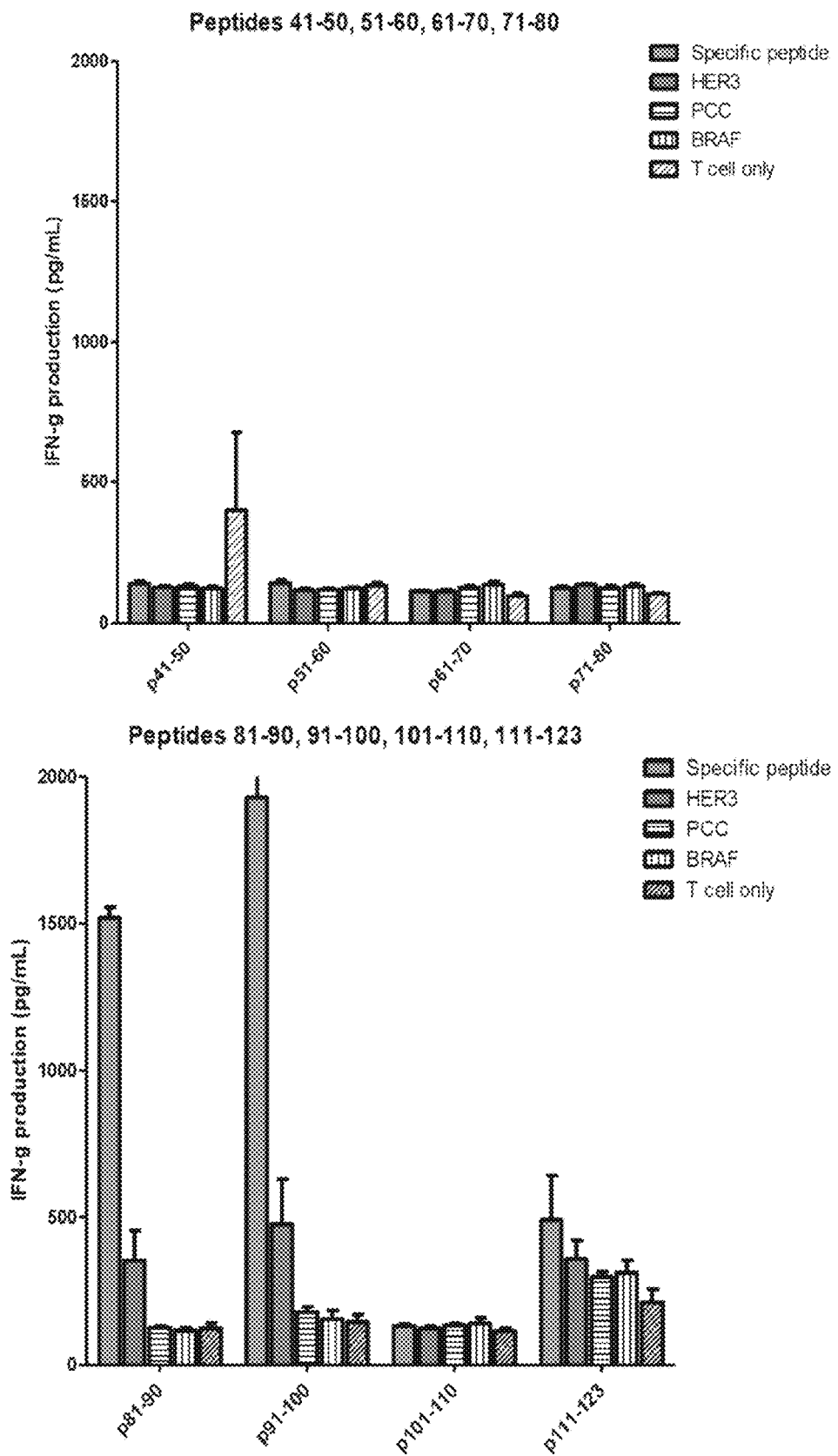
FIG. 11 shows IFN-γ production from a "REVERSE" screen in a patient not previously sensitized with HER extracellular domain, starting with whole peptide library, sensitizing to peptides and HER3 extracellular domain.
Figure 12:
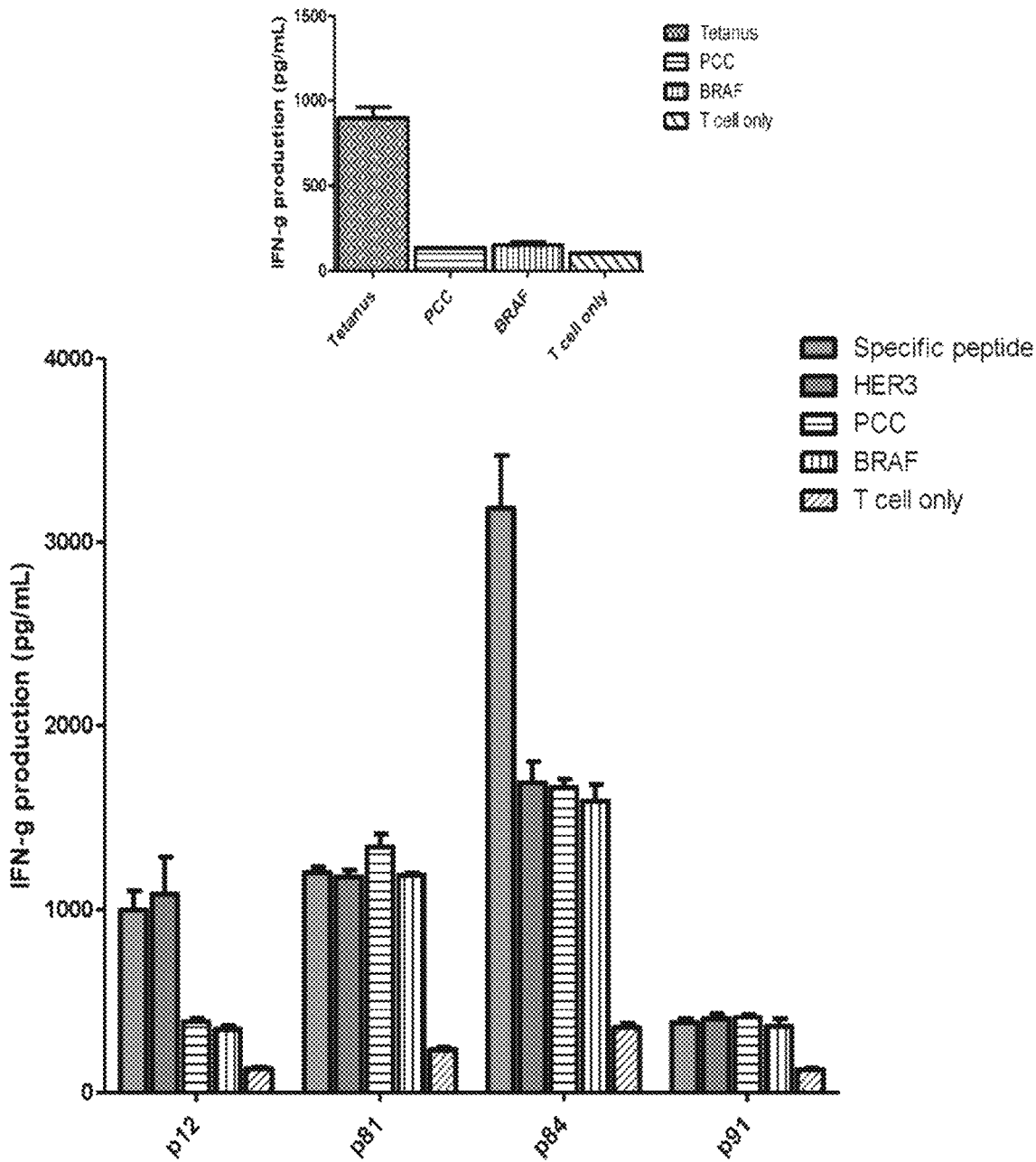
FIG. 12 shows IFN-γ production from a "REVERSE" screen in a patient not previously sensitized with HER extracellular domain, starting with peptides, sensitizing to peptides and HER3 extracellular domain.
Figure 13:
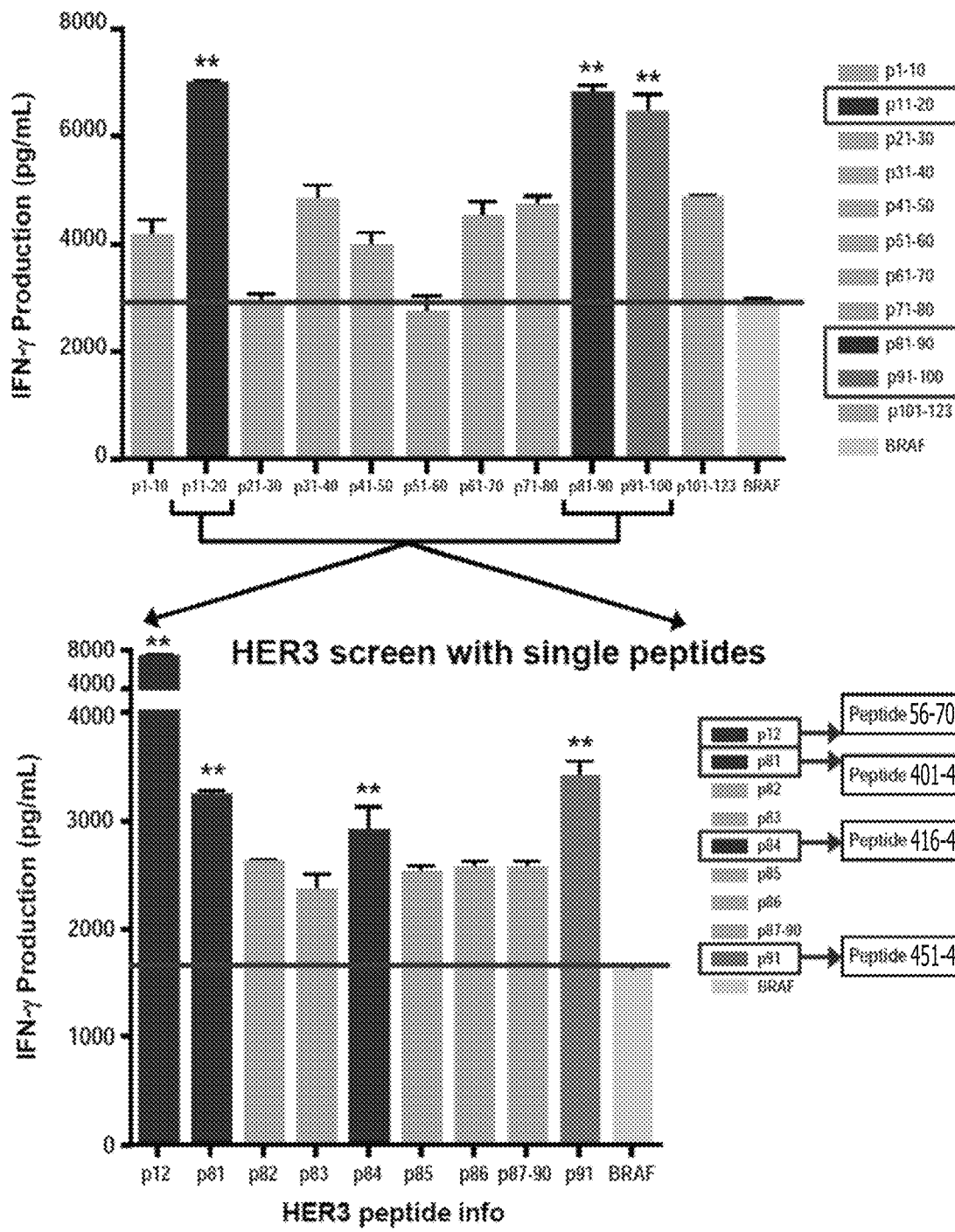
FIG. 13 shows a sequential peptide screen in donor # UPCC 15107-24.
Figure 14:
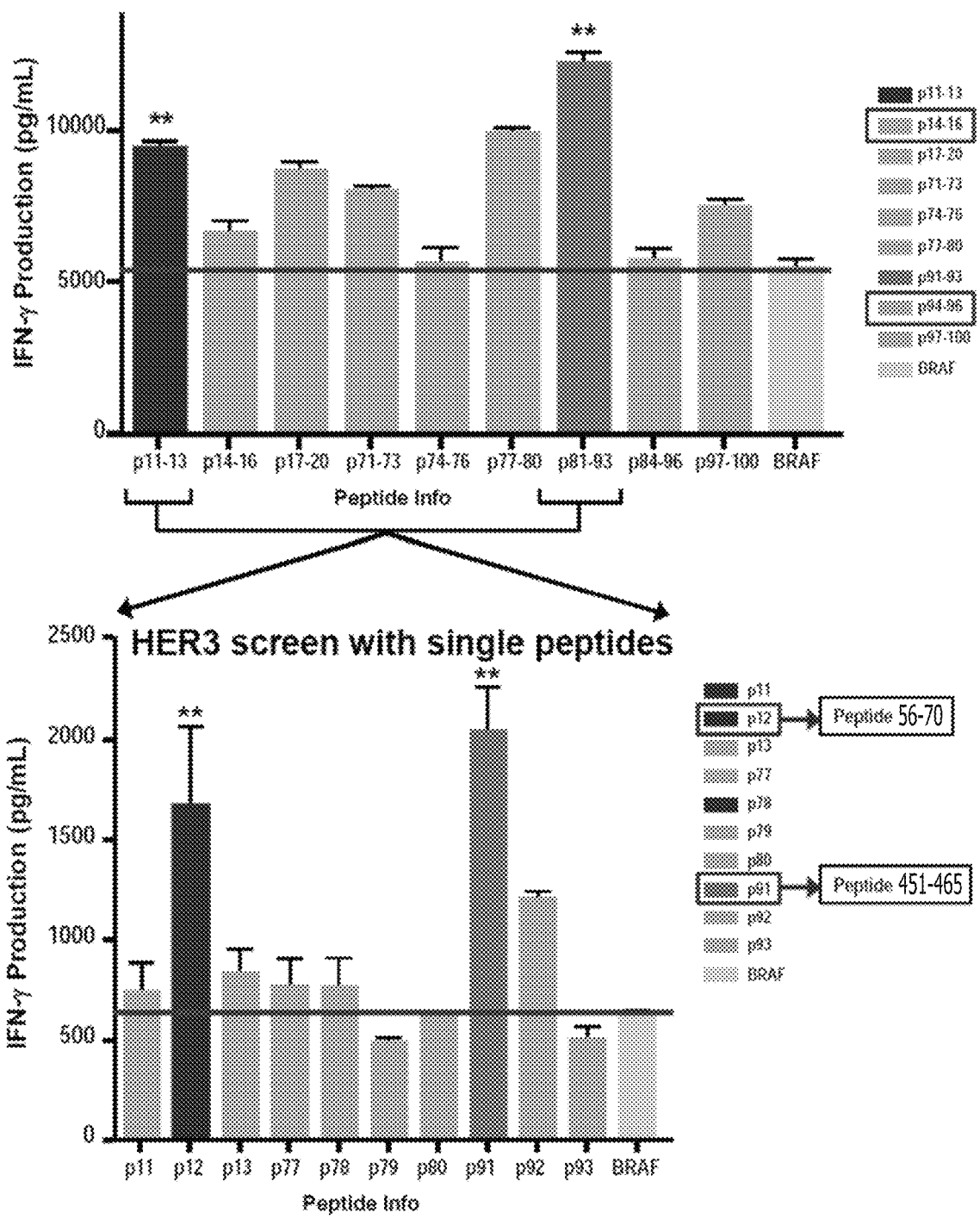
FIG. 14 shows a sequential peptide screen in donor # UPCC 15107-38.

Sequential Screening of HER3 ECD Peptide Library to Identify Immunogenic Epitopes Recognized by HER3 ECD-Sensitized CD4+ Th1 Cells Th1 sensitization was initially performed in 5 breast cancer patients with known anti-HER3 ECD reactivity in order to identify single immunogenic HER3 CD4+ epitopes. To achieve this. HER3 ECD-sensitized CD4+ Th1 were sequentially restimulated against 10-peptide clusters (1-10, 11-20, . . . etc.), narrowed to 3-peptide clusters (1-3, 3-6, 7-10, . . . etc.), and ultimately to single immunogenic HER3 peptides. Representative screens are shown in FIGS. 2, 13 and 14. Four immunogenic peptides—HER3(56-70) (SEQ ID NO: 4), HER3(401-415) (SEQ ID NO: 5), HER3(416-430) (SEQ ID NO: 6), and HER3(451-465) (SEQ ID NO: 7)—were reproducibly identified and promiscuous across HLA-DR, DP, and DQ subtypes. When Th1 cells from 4 non-HER3 reactive donors were sensitized using DC s pulsed with the four identified HER3 peptides, and subsequently challenged to recognize HER3 ECD-pulsed iDCs, all donors demonstrated successful sensitization not only to individual immunogenic HER3 peptides, but also recognized native HER3-ECD.

The results presented herein demonstrate that DC1 pulsed with an overlapping tumor antigen-derived peptide library can identify promiscuous class II peptides for CD4 T cell vaccine development. In this study, immunogenic HER3 CD4 peptides effectively overcome immune tolerance to self-tumor antigens. Utilization of these HER3 CD4 peptides in vaccine construction can be applied to patients harboring HER3-overexpressing cancers. Additionally, these results represent a novel strategy to rapidly and reproducibly identify class II-promiscuous immunogenic CD4 epitopes from any tumor antigen for cancer immunotherapy using a DC1-Th1 platform Table 1 below shows initial identification of immunogenic CD4+ HER3 ECD peptides in patients with known anti-HER3 reactivity. Table 2 shows the amino acid sequences of the four immunogenic HER3 CD4+ epitopes identified by the sequential screening.

TABLE 1

Four immunogenic peptides - HER356-70 (SEQ ID NO: 4), HER3401-415 (SEQ ID NO: 5), HER3416-430 (SEQ ID NO: 6), HER3451-465 (SEQ ID NO: 7) - were reproducibly identified across 5 donors previously sensitized to HER3 ECD

| Donor # | $HER3_{56-70}$ | $HER3_{401-415}$ | $HER3_{416-430}$ | $HER3_{451-465}$ |
|---|---|---|---|---|
| 15107-38 | ✓ |   |   | ✓ |
| 15107-24 | ✓ | ✓ | ✓ |   |
| 15107-26 | ✓ | ✓ | ✓ | ✓ |
| 26113-03 | ✓ | ✓ | ✓ | ✓ |
| 15107-31 |   |   | ✓ | ✓ |

TABLE 2

Amino add sequences of immimogenic HER3 CD4+ epitopes

| | | |
|---|---|---|
| $HER3_{56-76}$ | CEVVMGNLEIVLTGH | (SEQ ID NO: 4) |
| $HER3_{416-430}$ | SWPPHMHNFSVFSNL | (SEQ ID NO: 5) |
| $HER3_{416-430}$ | TTIGGRSLYNRGFSL | (SEQ ID NO: 6) |
| $HER3_{451-465}$ | AGRIYISANRQLCYH | (SEQ ID NO: 7) |

Figure 15:
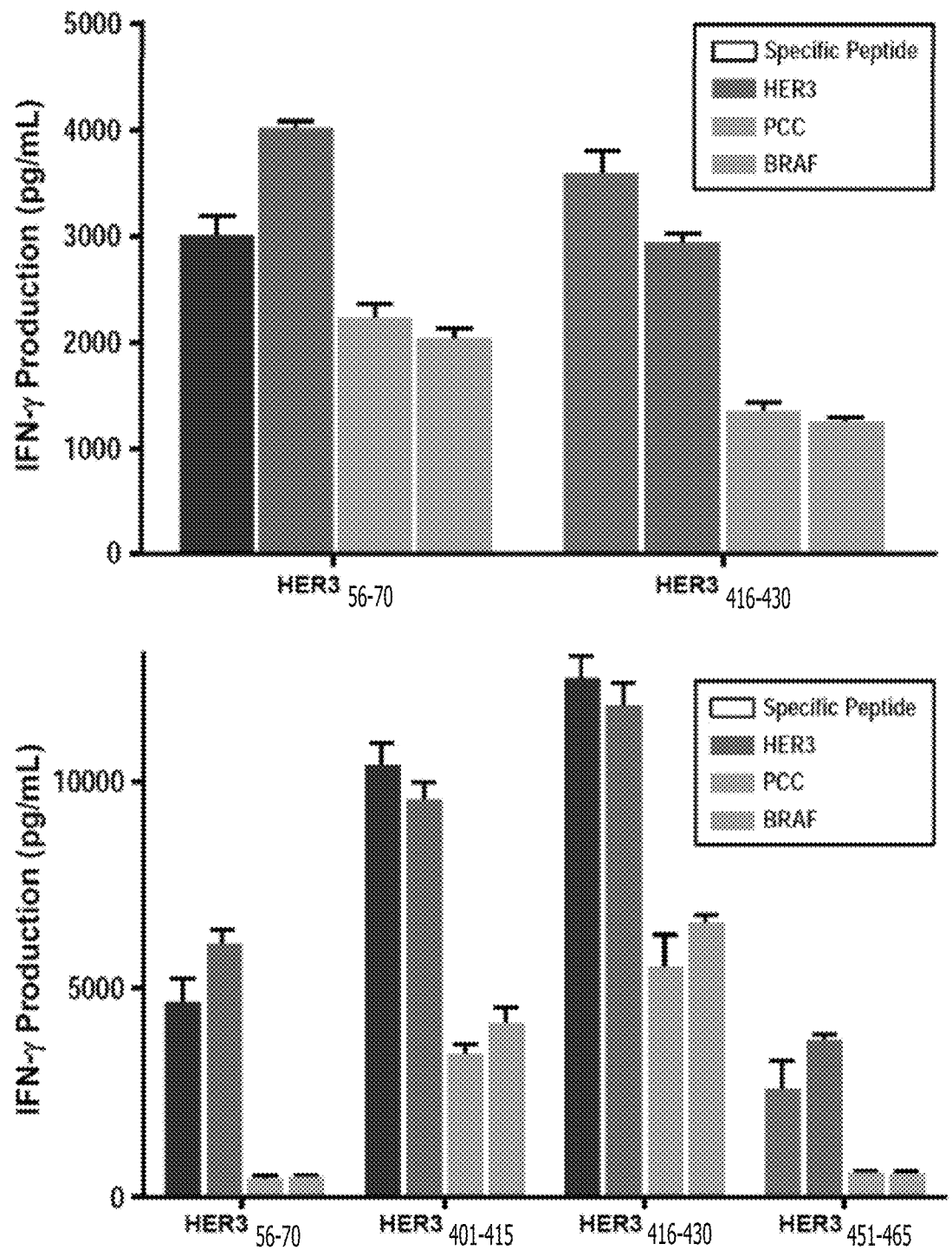
FIG. 15 shows "REVERSE" sensitization in donor # UPCC 15107-38 and UPCC 15107-24.

Confirmation of Immunogenicity of Identified CD4+ HER3 ECD Epitopes by "Reverse" Sensitization—i.e. Ability of Individual Epitope-Sensitized CD4+ Th1 to Recognize Native HER3 ECD FIG. 15 shows that in the donors with known HER3 ECD reactivity, CD4+ T-cells were sensitized with respective donor-specific immunogenic HER3 epitope-pulsed DC1s, and restimulated against iDCs pulsed with respective HER3 epitope and native HER3 ECD.

Figure 20:
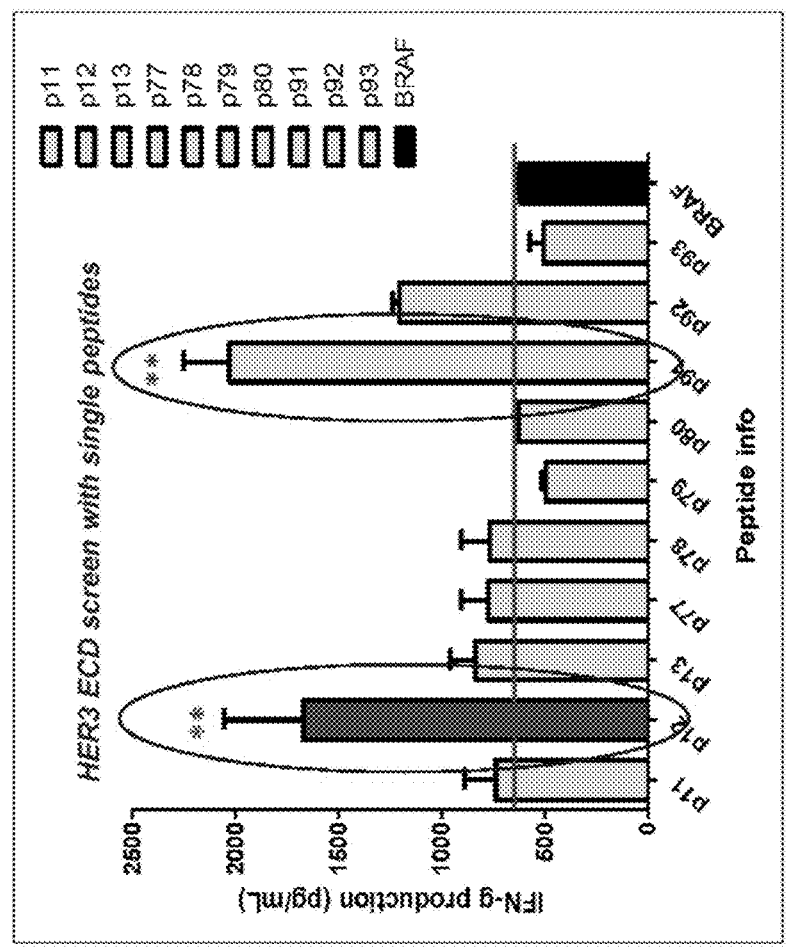
FIG. 20 shows confirmation of immunogenicity of identified CD4+ HER3 ECD epitopes by "reverse" sensitization. A HER3 ECD screen was performed with single peptides shown.
Figure 21:
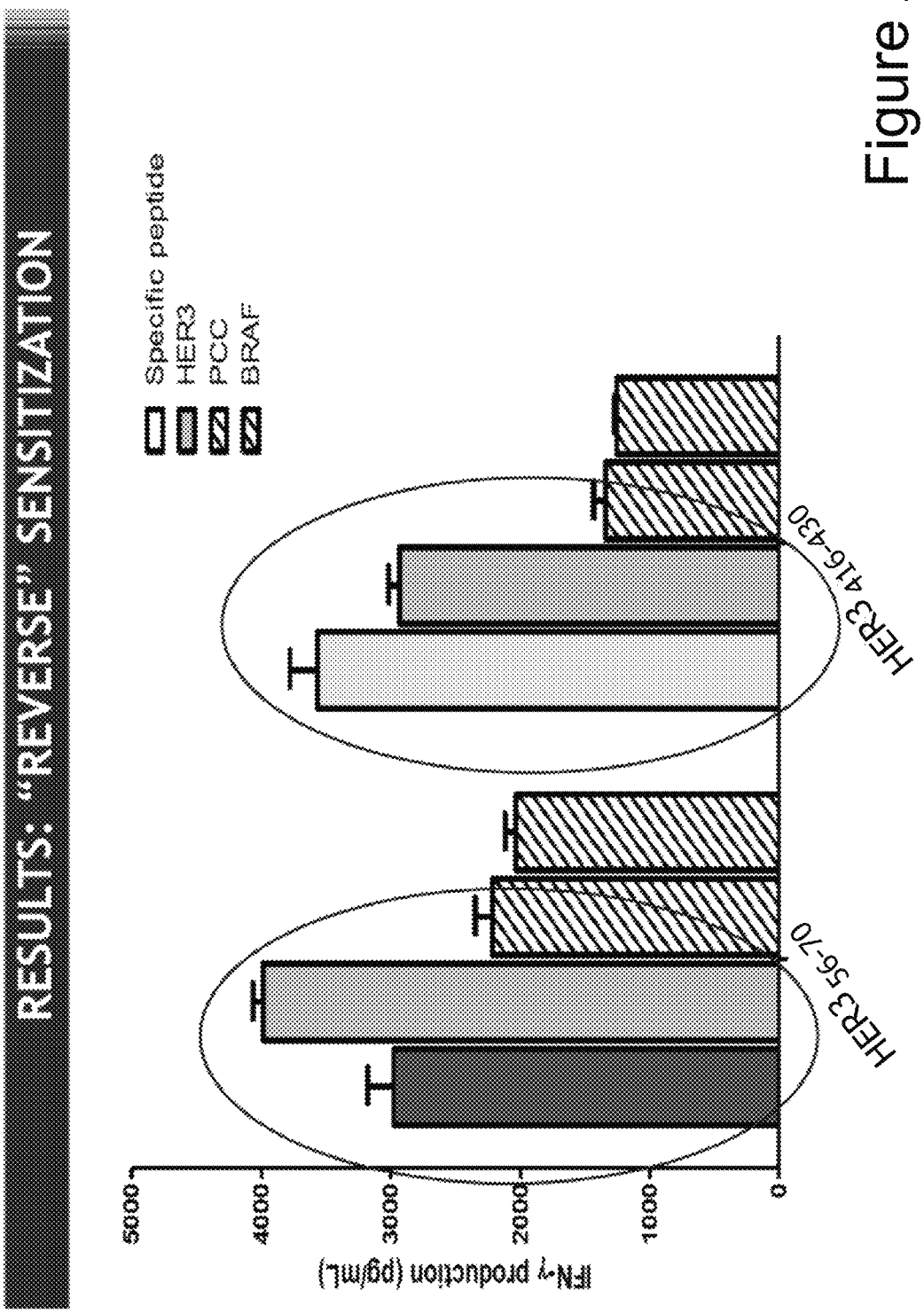
FIG. 21 shows additional results of confirmation of immunogenicity of identified CD4+ HER3 ECD epitopes by "reverse" sensitization.

FIGS. 20 and 21 show additional results of "reverse" sensitization

Figure 16:
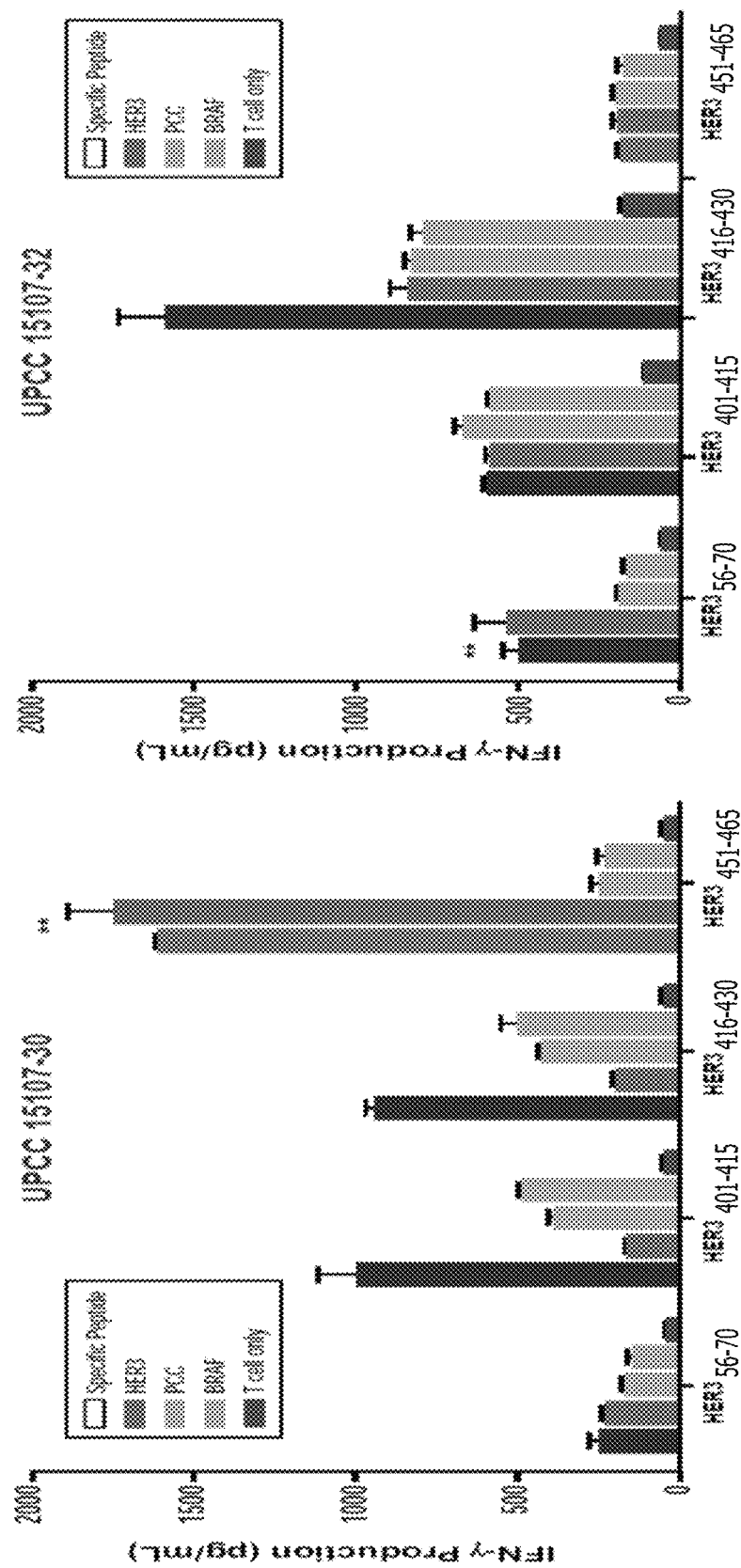
FIG. 16 shows that immunogenic HER3 epitope-pulsed DC1 sensitized CD4+ Th1 and overcame anti-HER3 immune tolerance in donor # UPCC 15107-30 and UPCC 15107-32 (both patients with known anti-HER3 non-reactivity to identified HER3 peptides and/or native HER3 ECD).

CD4+ Th1 Sensitized with Immunogenic HER3 Epitope-Pulsed DC1 Appears to Abrogate Anti-HER3 Immune Self-Tolerance As seen in FIG. 16, when CD4+ Th1 cells from four HER3 ECD nonreactive donors were sensitized using DC1s pulsed with the four identified HER3 peptides, and subsequently challenged to recognize HER3 ECD-pulsed iDCs, all donors demonstrated successful sensitization not only to individual HER3 epitopes, but also recognized native HER3 ECD.

CD4+ HER3 Epitopes Demonstrate MHC Class II Promiscuity

Figure 17:
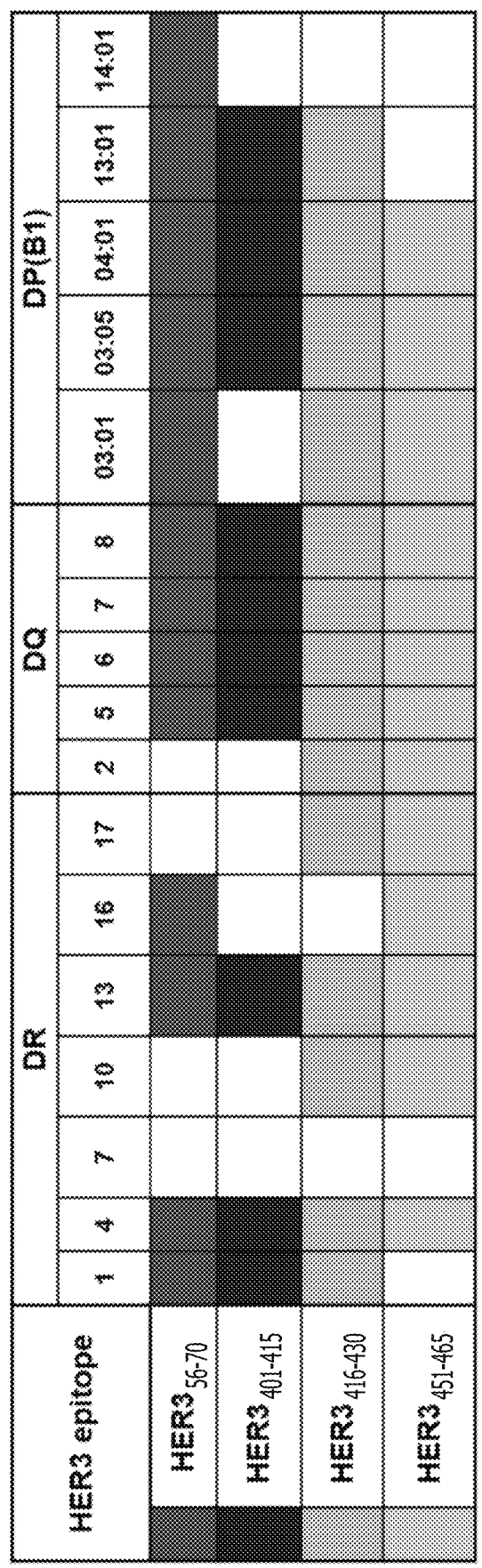
FIG. 17 shows immunogenic CD4+ HER3 epitopes demonstrate MHC class II promiscuity.
Figure 18:
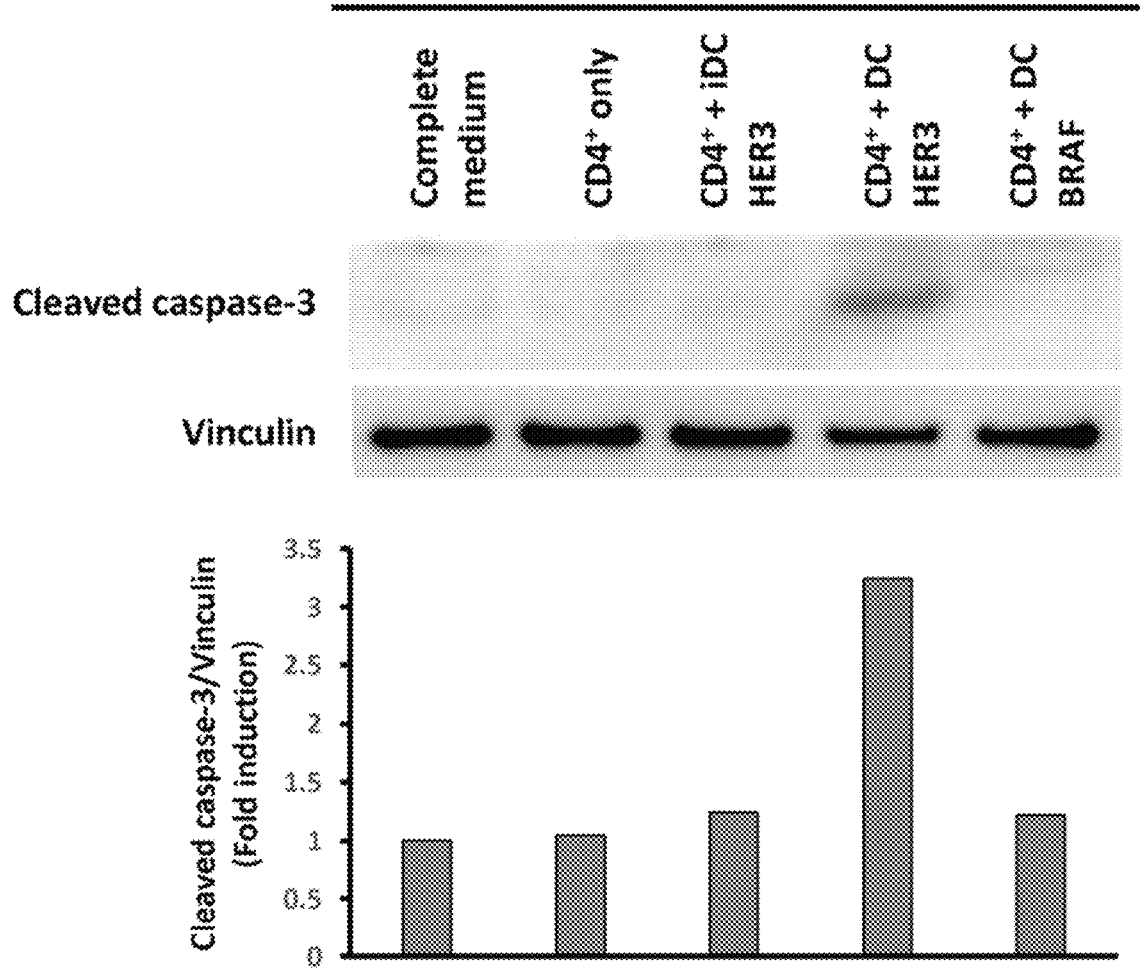
FIG. 18 shows that when activated HER3 CD4+ cells are placed next to HER3 expressing cells in a chamber, the HER3 CD4+ cells cause apoptosis or death of HER3 expressing cells breast cancer cells.

Using the extracellular domain (ECD) of HER3 as a candidate "oncodriver" tumor antigen, experiments were performed to identify immunogenic HER3 CD4+ peptides that demonstrate Class 11 promiscuity and generate anti-HER3 CD4+ immunity that can be used in a vaccine construct as seen in FIG. 17.

Peptides from Tumor Antigens

The results presented herein demonstrate that:
DC1 pulsed with an overlapping tumor antigen-derived peptide library can identify promiscuous MHC class II peptides for CD4+ T-cell vaccine development.
Immunogenic HER3 CD4+ peptides effectively overcome immune tolerance to self-tumor antigens.
These results represent a novel strategy to rapidly and reproducibly identify class II-promiscuous immunogenic CD4+ epitopes from any tumor antigen for cancer immunotherapy using a DC1-CD4+ Th1 platform.

Utilization of these HER3 CD4+ peptides in vaccine construction warrants investigation in patients harboring HER3-overexpressing cancers.

Example 3: HER3 Expression is a Marker of Tumor Progression in Premalignant Lesions of the Gastroesophageal Junction Over-expression of RTKs including members of the HER family, has prognostic and therapeutic significance in invasive esophagogastric carcinoma. RTK expression in premalignant gastroesophageal lesions has not been extensively explored previously.

Barrett's esophagus, or the presence of metaplastic columnar epithelium in the distal esophagus, predisposes to the development of esophageal adenocarcinoma. (Cameron, A. J., et al., *Gastroenterology* 109(5):1541-6 (1995).) While the histologic transition from dysplasia to invasive malignancy is well characterized, carcinogenesis in metaplastic cells involves genetic alterations that are incompletely understood. Several recent reports have identified human epidermal growth factor receptor 2 (HER2) expression in a subset of Barrett's esophagus lesions with dysplasia. (Almhanna, K., et al., *Appl. Immunohistochem. Mol. Morphol.* Jul. 16 2015) (Almhanna, et al.); Fassan. M., et al., *Histopathology* 61(5): 769-76 (2012) (Fassan, et al.); and Rossi. E., et al., *J. Cell. Mol. Med.* 13(9B):3826-33 (2009) (Rossi, et al.) Furthermore, the rate of HER2 expression correlates with degree of dysplasia, implicating related pathways in tumorigenesis.

Over-expression of RTK molecules, including members of the HER family (HER1, HER2, and HER3) and cMET, the mesenchymal-epithelial transition factor, have been demonstrated in many of the more common malignancies, including breast, lung, and gastrointestinal cancers (Yokata, J., et al., *Lancet* 1:765-767 (1986) as well as in esophagogastric carcinomas. The identification of HER2 overexpression in a subset of breast carcinomas, the association of HER2 overexpression with more aggressive biology and effective targeting of HER2 with a monoclonal antibody were pivotal events in the evolution of targeted therapies for the treatment of solid tumors. (Joensuu. H., et al., *N. Eng. J. Med.* 354(8):809-20 (2006).) This experience has provided a foundation for further efforts to target RTK molecules in the treatment of other malignancies.

HER2 overexpression has been demonstrated in a minority of gastric cancers and has been targeted with trastuzumab in the metastatic setting with a modest impact on outcome. (Bang, Y. J., et al., *Lancet* 376(9742) 687-97 (2010) (Bang, et al.) HER2 overexpression is more frequently expressed in proximal gastric and gastroesophageal junction compared to more distal gastric adenocarcinomas (Rajagopal, I., et al., *J. Clin. Diagn. Res.* 9(3):EC06-10 (2015)) and has been targeted with trastuzumab in the metastatic setting with a modest impact on outcome. (Bang, et al, and Fichter, C.D., et al., *Int. J. Cancer* 135(7):1517-30 (2014) (Fichter, et al.) HER1 and HER3 expression in gastric carcinomas have been associated with poor prognosis in most studies. (KandeL C., et al., *J. Clin. Pathol.* 67(4):307-12 (2014) and Havashi. M., et al., *Clin. Cancer Res.* 14(23):7843-9 (2008).) Overexpression of cMET is associated with poor prognosis in esophageal adenocarcinoma and inhibition of cMET-dependent signaling regulates the activity of HER1 and HER3. (Liu, X, et al., *Clin. Cancer Res.* 17(22):7127-38 (2011).) These data provide rationale for further efforts to characterize RTK expression in esophagogastric cancers and precursor lesions. The studies described below are aimed to characterize RTK expression in dysplastic lesions of the gastroesophageal junction in efforts to identify potential targets for treatment and primary prevention.

Methods

Figure 22:
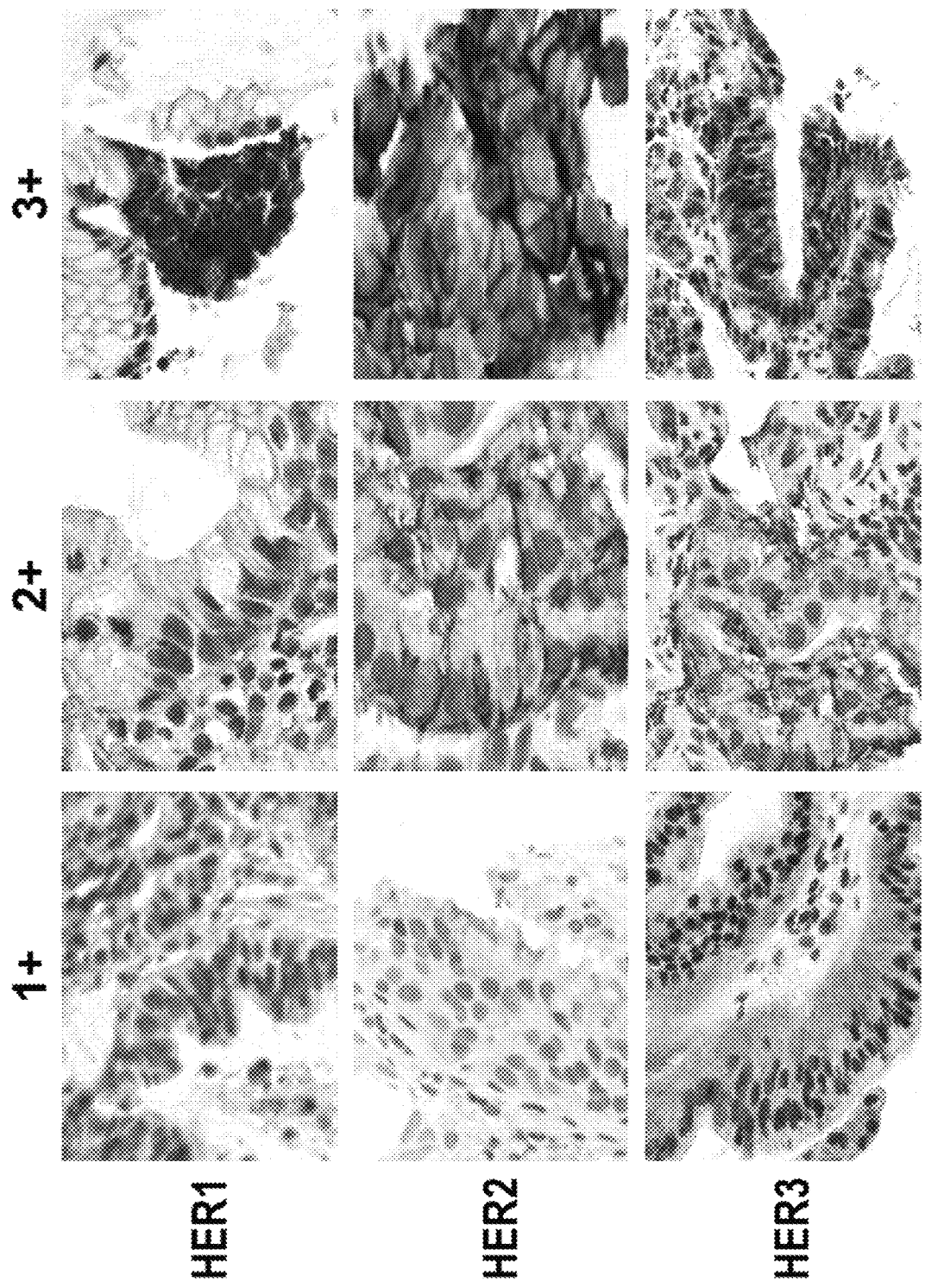
FIG. 22 shows photographs of immunohistochemistry scoring of HER staining.

Following approval by the Institutional Review Board of the University of Pennsylvania, the clinical records and histologic specimens from 73 patients with Barrett's esophagus with dysplasia (low-grade dysplasia (LGD), n=32, or high-grade dysplasia (HGD), n=59) were retrospectively reviewed. Formalin-fixed paraffin-embedded tissue blocks from stored endoscopic biopsy and mucosal resection specimens from 2003-2012 were sectioned at 5 μm on plus slides (Fisher Scientific, Waltham, Mass.) and subsequently deparaffinized and rehydrated. All biopsy materials were immunostained for HER1 (clone H11; 1:50; DAKO), HER2 (HercepTest, DAKO, Carpinteria, Calif.) and HER3 (clone RTJ.2: 1:30; Santa Cruz Biotechnology, Dallas, Tex.) (Leica Bond-III instrument) and evaluated under the microscope (Leica Bond-III) by a single pathologist. Membrane 3+ HER staining was considered positive, as was membrane 2+ HER2 staining in ≥10% of tumor cells as seen in FIG. 22, cMET immunohistochemistry was performed in 42 cases when sufficient tissue was available; moderate or strong membranous staining in ≥50% of tumor cells was considered positive. RTK overexpression was correlated with clinical data to evaluate for associations with invasive carcinoma, either paired dysplasia-adenocarcinoma biopsy specimens or the diagnosis of adenocarcinoma on subsequent biopsy specimens.

Statistical Analysis

Two tailed tests were used for all analyses. Descriptive statistics are presented as frequencies for categorical variables and median (interquartile range (IQR) for continuous variables. Pearson'$\chi 2$ or Fisher's exact tests and Wilcoxon rank-sum test were used to analyze categorical and continuous variables, respectively. P-values≤0.05 were considered statistically significant; all tests were two-sided. Analyses were carried out using SPSS v22.0 (IBM, Armonk, N.Y.).

Results

A total of 73 patients with Barrett's esophagus with low-grade dysplasia (n=32) or high-grade dysplasia (n=59) were identified and analyzed for HER1. HER2, HER3 and cMET expression by immunohistochemistry. Median age of the cohort was 65 years (IQR 60-73 years); 81.9% were male and 87.5% were Caucasian. The rate of alcohol use in the cohort was 14.3% and the rate of active cigarette use was 6.3%, yet 55.6% were former smokers. 26.4%/0 had a family history of malignancy. There were no significant differences between the LGD and HGD cohorts in the measured clinical and demographic variables as seen below in Table 3.

TABLE 3

Demographic and Clinical Characteristics of Cohort with Dysplastic Barrett's Esophagus, and Univariate Comparison of Low-grade and High-grade

|  | LGD Median (IQR) or no. of patients (%) | HGD Median (IQR) or no. of patients (%) | p-value |
|---|---|---|---|
| Age, years | 64.0 (60.0-77.5) | 66.0 (63.0-72.0) | 0.621 |
| Sex, male | 19 (73.1) | 41 (87.2) | 0.130 |
| Caucasian race | 23 (95.8) | 41 (93.2) | 0.755 |
| Cigarette use Current | 2 (9.1) | 2 (4.8) | 0.681 |
| Former | 13 (59.1) | 23 (54.8) |  |
| Alcohol use | 2 (9.1) | 7 (16.7) | 0.683 |
| Positive family history | 6 (28.6) | 13 (32.5) | 0.753 |

High-grade dysplasia (HGD) was associated with overexpression of HER1 (22.4% vs. 3.1%, p=0.016), HER2 (5.3% vs. 0.0%, p=0.187) and HER3 (45.6% vs. 9.4%, p<0.001) compared to low-grade dysplasia (LGD).

Figure 23:
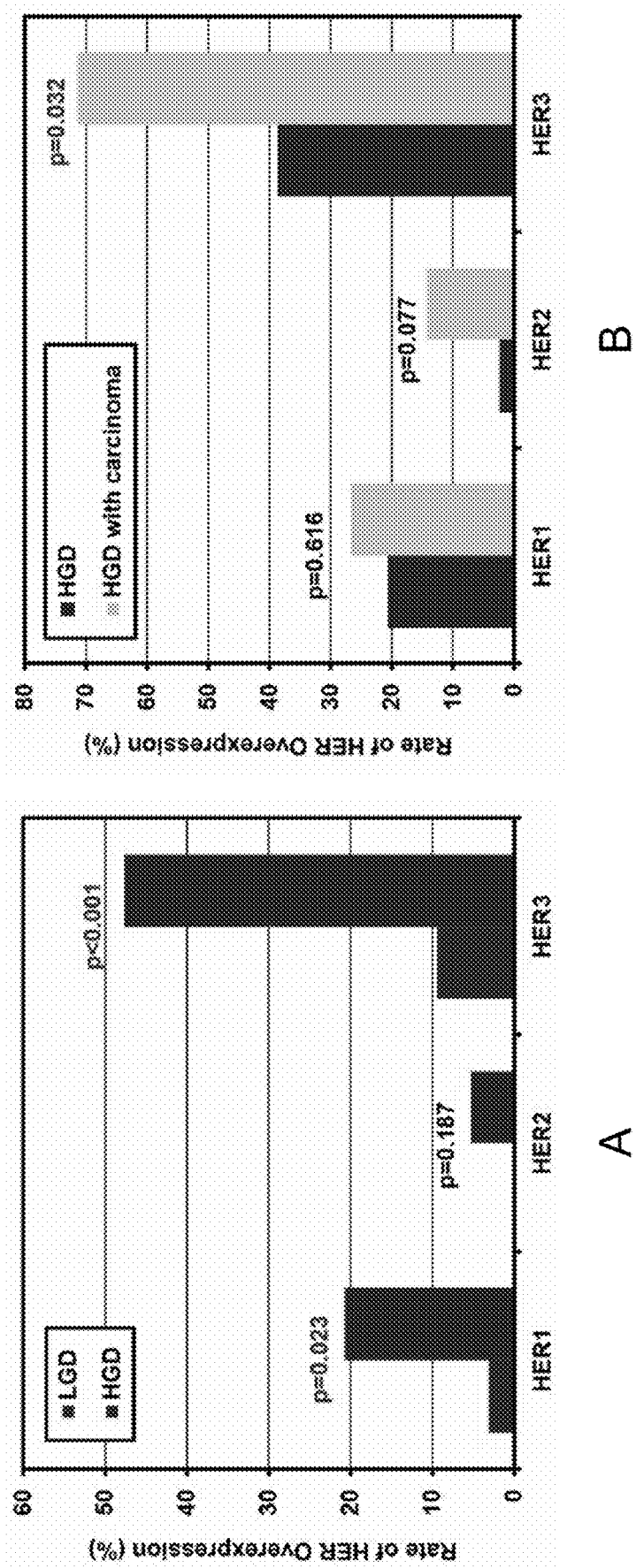
FIGS. 23A and 23B are histograms showing rate of HER family overexpression in Barrett's esophagus with low-grade dysplasia (LGD) or high-grade dysplasia (HGD) (FIG. 23A), and high-grade dysplastic Barrett's lesions with (HGD with carcinoma)) or without associated invasive cancer (HGD) (FIG. 23B).

Foci of invasive esophageal adenocarcinoma were associated with dysplastic lesions in 6 cases, all of which arose in association with HGD (HGD: 10.2% vs. LGD: 0.0%, p<0.001). An additional 9 patients were diagnosed with invasive esophageal adenocarcinoma on subsequent biopsy specimens (HGD: 17.0% vs. LGD: 0.0%, p=0.017). There was a significant association of HER3, but not HER1 or HER2 (increase in HER1 (26.7% vs. 20.5%, p=0.616) and HER2 (14.3% vs. 2.3%, p=0.077), overexpression in HGD lesions compares with those without foci of invasive carcinoma (71.4% vs. 38.6%, p=0.032) as seen in FIGS. 23A and 23B.

Overexpression of cMET was observed in 18 of 42 (42.9%) evaluated specimens and was increasingly observed in HGD compared to LGD specimens (58.3% vs. 36.7%, p=0.200) and was most often co-expressed with HER3 (62.5% of HER3-positive specimens vs. 38.2% of HER3-negative specimens (p=0.212)). Similar trends were not observed in HER1-positive (p=0.729) or HER2-positive (p=NA) specimens. One of the 42 (5.6%/0) patients had invasive carcinoma identified; cMET was overexpressed in this patient (p=0.243).

Discussion:

This analysis of RTK expression in dysplastic lesions of the gastroesophageal junction confirms that (1) HER family proteins are upregulated in Barrett's esophagus with dysplasia: (2) the frequency of HER family and cMET overexpression is positively correlated with the degree of dysplasia: and (3) HER protein upregulation, particularly in dysplastic lesions, is associated with an increased incidence of associated invasive cancer.

HER3 may therefore serve as a biomarker for occult invasive disease in patients with Barrett's esophagus and HGD. Additionally, therapeutics targeting HER3 or CMET may afford secondary prevention of gastroesophageal carcinoma in subsets of patients.

Previous evaluations of HER expression in Barrett's esophagus have been limited to an assessment of HER2, which is overexpressed in a minority of cases. See. Almhanna, et al., Fassan, et al., and Rossi, et al. HER2 overexpression in this study was present in 3.3% of biopsy specimens, lower than the rate of HER1 or HER3 overexpression. This pattern is consistent with HER family protein expression in invasive gastroesophageal junction cancers, where HER3 is overexpressed more commonly than HER2 Fichter, et al. Increasing HER3 protein overexpression with progression from LGD to HGD and frequent overexpression of HER3 in particular, represent novel, though not unanticipated findings. Homo- and hetero-dimerization of HER receptors drive signal activation; clustered overexpression of multiple members of the HER family have been observed in other tumor types. In conjunction, activated c-MET positively regulates the activity of HER1 and HER3[11]. Indeed, the interplay between these receptors have provided rationale for multivalent therapeutic approaches targeting multiple RTKs. (Baselga, J., et al., *N. Eng. J. Med.* 366(2): 109-19 (2012); Waddell, T., et al., *Lancet Oncol.* 14(6):481-489 (2013))

The present data also suggest an opportunity for targeted secondary prevention of gastroesophageal carcinoma that has not yet been explored. Previously targeted HER2 expression in ductal carcinoma in situ (DCIS) of the breast has been targeted with promising results. See, U.S. Published Application US 2015/0323547 A1; U.S. Ser. No. 14/985,303 filed Dec. 30, 201; Datta, J., et al., *Oncolmmunology* 4:8 e1022301 (2015) DOI:10. 1080/2162402X.2015. 1022301; Datta, J., et al., *Breast Cancer Res.* 17(1):71 (2015). Such an approach remains a more distant goal for gastrointestinal malignancies. Notwithstanding, current treatment options for Barrett's esophagus, including endoscopic resection and ablative modalities and radical surgery all have significant limitations. Alternative strategies that spare morbidity and mitigate the risk of invasive carcinoma are needed. This analysis of RTK expression in dysplastic lesions of the gastroesophageal junction confirms that (1) HER family proteins are upregulated in Barrett's esophagus with dysplasia; (2) the frequency of HER family and cMET overexpression is positively correlated with the degree of dysplasia; and (3) HER protein upregulation, particularly in dysplastic lesions, is associated with an increased incidence of associated invasive cancer.

HER3 may therefore serve as a biomarker for occult invasive disease in patients with Barrett's esophagus and HGD. Additionally, therapeutics targeting HER3 or CMET may afford secondary prevention of gastroesophageal carcinoma in subsets of patients.

In summary, the present data indicate a relationship between frequent overexpression of HER3 in high-grade dysplastic lesions of the gastroesophageal junction, especially those with occult invasive carcinoma and malignant transformation. These findings may justify a more aggressive management approach for HER3-expressing dysplastic lesions and provide rationale for the future application of HER3-targeted therapeutics in an early disease setting as will be readily appreciated by those skilled in the art.

We have previously shown a progressive loss in the native anti-HER-2 CD4 Th1 during HER-$2^{pos}$ breast tumorigenesis. This loss of response was associated with lack of pathologic complete response ("pCR") to neoadjuvant treatment, and correlated with elevated risk of breast cancer recurrence and could be restored with vaccination. Example 4 below explores whether there is a similar loss in anti-HER3 Th1 response during breast tumorigenesis.

Example 4: Loss of Anti-HER3 CD4 Th1 Occurs in Breast Tumorigenesis and is Negatively Associated with Outcomes Overall Example 4 Summary We have previously shown a progressive loss in the native anti-HER2 CD4 Th1 during HER$2^{pos}$ breast tumorigenesis. This loss of response was associated with lack of pathologic complete response ("pCR") to neoadjuvant treatment, and correlated with elevated risk of breast cancer recurrence and could be restored with vaccination. This Example explores whether there is a similar loss in anti-HER3 Th1 response during breast tumorigenesis.

Peripheral blood from 131 subjects, including healthy donors ("HDs"), benign breast disease ("BD"), ductal carcinoma in situ ("DCIS") and invasive breast cancer ("IBC") patients was collected. Immune responses to four different HER3 immunogenic peptides identified in Examples 1 and 2 above were tested via enzyme linked immunosorbent (ELISpot) assay and all metrics of immune response were analyzed.

There was a significant decline in the anti-HER3 response going from HDs to IBC. Triple negative ("TN") IBC had the lowest response across all three immune parameters. HDs had significantly higher immune responses than both ER$^{pos}$ IBC and TN IBC patients across all three immune parameters. Interestingly. HER$2^{pos}$ IBC displayed immune responses similar to that of HDs and BDs. Patients with recurrent breast cancer and lack of pCR to neoadjuvant therapy had significantly lower anti-HER3 CD4 Th1 responses than patients with no subsequent recurrences or those having a pCR to neoadjuvant therapy.

Thus, it was found that CD4 Th1 anti-HER3 are lost during breast tumorigenesis, most notably in TN IBC, a group with limited treatment options and markedly worse prognosis with HER3 overexpression. These findings have implication for attempting to restore this response to prevent recurrence.

Background

Nearly one in eight women will develop breast cancer in their lifetime. Of those, cancers over-expressing HER2 are associated with a higher rate of distant metastases and overall worse prognosis. The introduction of trastuzumab, a monoclonal antibody against HER2, has dramatically enhanced progression free survival and overall survival in patients with HER2 positive cancers, pointing to HER2's key role in modulating breast cancer progression. Giordano S. H., et al., *J. Clin. Oncol.* (2014): JCO-2013 [Published online before print May 5, 2014, doi: 10.1200/ JCO.2013.54.0948].

The immune system plays a key role in modulating HER2 expressing tumors. It has been previously shown there is a step-wise decline in native anti-HER2 CD4 T cell response going from healthy subjects to HER$2^{pos}$ DCIS to HER$2^{pos}$ IBC, but not HER$2^{pos}$ IBC. Further, lower anti-HER2 immune responses correlated with subsequent breast cancer recurrence while higher anti-HER2 immune responses correlated with pathologic complete response to neoadjuvant chemotherapy, implicating the immune system's role in HER$2^{pos}$ tumorigenesis. See, Datta, J., et al., *Oncolmmunology* 4(10):e1027474. DOI: 10.1080/2162402X.2015. U.S. Pat. No. 1,022,301 (2015) and U.S. Published Application US 2015/0323547 A1 (collectively hereinafter. "Datta, et al."). Our group has developed a HER2 pulsed dendritic cell vaccine that restores anti-HER2 CD4 and CD8 T cell responses in both DCIS and IBC patients. Sharma, A., et al., *Cancer* 118(17):4354-4362 (2012); Koski, G. K., et al., *J. Immunother.* 35(1):54-65 (2102); and U.S. Published Application US 2015/0323547 A1.

HER2 is a member of the EGFR family, a group of RTKs that also include HER1 and HER3. While it is well known that HER2 self-dimerizes, the role of HER3 in signaling is less clear and it may act to dimerize both with itself and HER2. HER3 dimerization with HER2 has been proposed as an escape mechanism in breast cancer patients treated with trastuzumab. Czopek, J., et al., *Contemp. Oncol.* 17(5):446-9 (2013) ("Czopek, et al.") and Bae. S. Y., et al., *Breast Cancer Res. Treat.* 139(3):741-50 (2013) ("Bae, et al."). Pertuzumab, a recent addition to the market and the first oncology drug to receive accelerated FDA approval as neoadjuvant treatment, inhibits HER2/HER3 dimerization and has been shown to have an overall survival benefit when used in combination with trastuzumab for breast cancer patients. Jhaveri, K., et al., *J. Natl. Compr. Canc. Netw.* 12(4):591-8 (2014) and Harbeck, N., et al., *Breast Care* 8(1):49-55 (2013).

HER3 expression is less clearly delineated among the sub-types of breast cancer although there is overexpression seen in some ER-positive, HER2-positive and triple negative ("TN") subtypes. Moeder, C., et al., *Cancer* 115(11): 2400-9 (2009). It is of interest that while HER3 overexpression may be more common in HER$2^{pos}$ IBC, its prognostic value is more significant in TN IBC. While HER3 expression in $ER^{pos}/HER2^{pos}$ IBC did not impact disease-free survival ("DFS") or overall survival ("OS"), HER3 expression in TN IBC was correlated with both a worse 5-year DFS and 10-year OS. Bae, et al, and Czopek, et al. Notably, the sizeable subset of TN IBC patients with HER3 overexpression, a group that by definition does not have any of the classical treatment options, may benefit from a recognizable new target. It is unknown whether the anti-HER3 CD4 Th1 response exists in healthy donors and whether this response changes during breast tumorigenesis. The present study seeks answers to these questions.

Methods

Subject Enrollment

A total of 131 subjects met study criteria and were consecutively enrolled at the University of Pennsylvania with informed consent. This study was approved by the Institutional Review Board of the University of Pennsylvania and the Abramson Cancer Center prior to subject enrollment. Of 131 subjects, nine had insufficient peripheral blood monocytes to perform assays, leaving 122 subjects with immune response data for review. CD4 T cell responses to four different HER3 immunogenic peptides were compared between healthy donors (HD, n=30), patients with benign breast disease (BD, n=13), DCIS (n=13), $HER2^{pos}$ IBC (n=21), $ER^{pos}$ invasive breast cancer ($ER^{pos}$ IBC, n=20) and triple negative IBC (TN IBC, n=27).

Peripheral Blood Monocyte Collection

Peripheral blood was collected by venipuncture. Blood was diluted in Hank's buffer or PBS at a 1:1 ratio and lymphocyte separation media was layered below diluted blood in conical tubes. Blood was then separated by density centrifugation at 1200 rpm for 30 minutes. Monocyte layers were collected and washed twice in Hank's buffer or PBS. Cells were counted and resuspended at 10 million cells per milliliter and frozen at minus 80° C. for 24-48 hours before being transferred to minus 200° C., where cells remained stored until experimental assay.

Measuring Anti-HER3 CD4 Th1 Response

Anti-HER3 CD4 Th1 cell response were measured by ELISpot assay, according to the manufacturer's protocol. Briefly, 96 well PVDF membrane plates were activated with 70% ethanol washed with PBS then coated with anti-IFN-gamma (anti-IFN-$\gamma$) antibody and incubated overnight at 4° C. 24 hours later, plates were again washed with PBS then blocked with Iscove's media with 10% human serum for 1 hour. Peripheral blood monocytes were thawed at 37° C., washed in PBS or Hank's buffer, counted and resuspended at 1 million cells per milliliter then plated at 200,000 cells per well with one of four immunogenic HER3 peptides (p12 (Peptide 56-70): CEVVMGNLEIVLTGH (SEQ ID NO: 4); p81 (Peptide 401-415): SWPPHMHNFSVFSNL (SEQ ID NO: 5); p84 (Peptide 416-430): TTIGGRSLYNRGFSL (SEQ ID NO: 6); and p91 (Peptide 451-465): AGRIYISANRQLCYH (SEQ ID NO: 7), anti-CD3/CD28 (polycloncal stimulus, positive control) tetanus toxoid (Santa Cruz Biotechnology, Dallas, Tex.) or nothing (unstimulated control). Assays were performed in triplicate. Plates were incubated at 38° C. for 48 hours. After 48 hours, plates were washed with PBS, biotinylated anti-IFN-$\gamma$ antibody was then added and plates were incubated at 38° C. for two hours. Plates were again washed with PBS, streptavidin-HRP was added and plates were incubated at 38° C. for one hour. Finally, plates were washed with PBS then TMB substrate solution was added. Color development was stopped after five minutes by washing extensively with tap water. Plates were dried overnight at 4° C.

Immune Response Analysis

Spots were counted via immunospot software. Three parameters or metrics were quantified to determine immune response: (I) cumulative response, or the summed response to all four HER3 immunogenic peptides in spots per million cells. (2) repertoire, or the number of peptides per subject with 20 or more spots, and (3) responsivity, or the percent of subjects responding to at least one peptide (defined as a threshold of 20 or more spots). Tetanus response in spots per 200,000 cells and anti-CD3/CD28 response in spots per 200,000 cells were also quantified as controls. All immune response metrics were analyzed in graphpad prism software.

Results

Study Subject Characteristics

A total of 131 subjects met study criteria and were consecutively enrolled with informed consent at the Hospital of the University of Pennsylvania. Nine subjects had insufficient cells for analysis, leaving 122 subjects. Of these, the mean age was 50, ranging from 25 to 83. 72.1% were Caucasian, 18.0% African American and 9.8% another race. Subjects fell into one of five groups: HDs (n=30), BDs (n=11), DCIS (n=13), $HER2^{pos}$ IBC (n=21), $ER^{pos}$ IBC (n=20) or TN IBC (n=27). Of the 68 IBC subjects, 35 (51.5%) were Stage I, 22 (32.4%) were Stage II, 9 (13.2%) were Stage III and 2 (2.9%) were Stage IV. 52 (76.5%) had undergone chemotherapy and/or herceptin and/or tamoxifen treatment, while 16 (23.5%) were treatment-naïve. Three DCIS patients and three $HER2^{pos}$ IBC patients received HER2 pulsed dendritic cell vaccination. Other characteristics are reported in Table 4 below.

TABLE 4

Characteristics of study subjects

| Characteristics | Healthy Donors | Begnin Breast Disease | Ductal Carcinoma in Situ | HER-$2^{pos}$ Invasive Breast Cancer | $ER^{pos}$ Invasive Breast | Triple Negative Invasive Breast Cancer |
|---|---|---|---|---|---|---|
| n = | 30 | 11 | 13 | 21 | 20 | 27 |
| Mean Age | 44 (25-60) | 50 (37-75) | 54 (40-68) | 50 (31-61) | 57 (36-83) | 53 (35-74) |
| Race | | | | | | |
| Caucasian (%) | 21 (70%) | 8 (72.7%) | 9 (69.2%) | 15 (71.4%) | 19 (95%) | 16 (59.3%) |
| African American (%) | 5 (16.7%) | 2 (18.2%) | 4 (30.8%) | 3 (14.3%) | 0 (0%) | 8 (29.6%) |
| Other | 4 (13.3%) | 1 (9.1%) | 0 (0%) | 3 (14.3%) | 1 (5%) | 3 (11.1%) |
| Pregnancy Status | | | | | | |
| 0 Pregnancies | 15 (50%) | 2 (18.2%) | | | | |
| ≥1 Pregnancies | 15 (50%) | 9 (81.8%) | | | | |

TABLE 4-continued

Characteristics of study subjects

| Characteristics | Healthy Donors | Begnin Breast Disease | Ductal Carcinoma in Situ | HER-2$^{pos}$ Invasive Breast Cancer | ER$^{pos}$ Invasive Breast | Triple Negative Invasive Breast Cancer |
|---|---|---|---|---|---|---|
| Meopausal Status | | | | | | |
| Pre-Menopausal | 22 (73.3%) | 8 (72.7%) | | | | |
| Post-Menopausal | 8 (26.7%) | 3 (27.3%) | | | | |
| Receptors | | | | | | |
| ER | | | 11 (84.6%) | 15 (71.4%) | 20 (100%) | 0 (0%) |
| HER-2 | | | 6 (46.2%) | 21 (100%) | 0 (0%) | 0 (0%) |
| HER-3 | | | | | | |
| Stage | | | | | | |
| Stage I | | | | 14 (66.7%) | 12 (60%) | 9 (33.3%) |
| Stage II | | | | 5 (23.8%) | 4 (20%) | 13 (61.9%) |
| Stage III | | | | 2 (9.5%) | 3 (15%) | 4 (14.8%) |
| Stage IV | | | | 0 (0%) | 1 (5%) | 1 (3.7%) |
| Treatment Status at Study Entry | | | | | | |
| No Chemotherapy | | | 13 (100%) | 4 (19%) | 5 (25%) | 7 (25.9%) |
| Neo-adjuvant Chemotherapy | | | 0 (0%) | 7 (33.3%) | 1 (5%) | 8 (29.6%) |
| Adjuvant Chemotherapy/ Trastuzumab/ Anti-Estrogen | | | 0 (0%) | 10 (47.6%) | 14 (70%) | 12 (44.4%) |
| DC1 Vaccine | | | 3 (23.1%) | 3 (14.3%) | 0 (0%) | 0 (0%) |
| Lymph Node Status at Initial Surgery | | | | | | |
| 0 Positive Nodes | | | 13 (100%) | 13 (61.9%) | 12 (60%) | 13 (48.1%) |
| ≥1 Positive Nodes | | | 0 (0%) | 8 (38.1%) | 8 (40%) | 14 (51.9%) |
| Time Since Diagnosis | | | | | | |
| <1 year | | | 4 (30.8%) | 9 (42.9%) | 5 (25%) | 11 (40.7%) |
| ≥1 year | | | 9 (69.2%) | 12 (57.1%) | 15 (75%) | 16 (59.3%) |
| Subsequent Breast Events of Those ≥1 Year Since Diagnosis | | | | | | |
| NED Since Initial Treatment | | | 9 (100%) | 10 (83.3%) | 13 (86.7%) | 13 (81.3%) |
| Recurrent Breast Cancer | | | 0 (0%) | 2 (16.7%) | 2 (13.3%) | 3 (18.7%) |

Figure 24A:
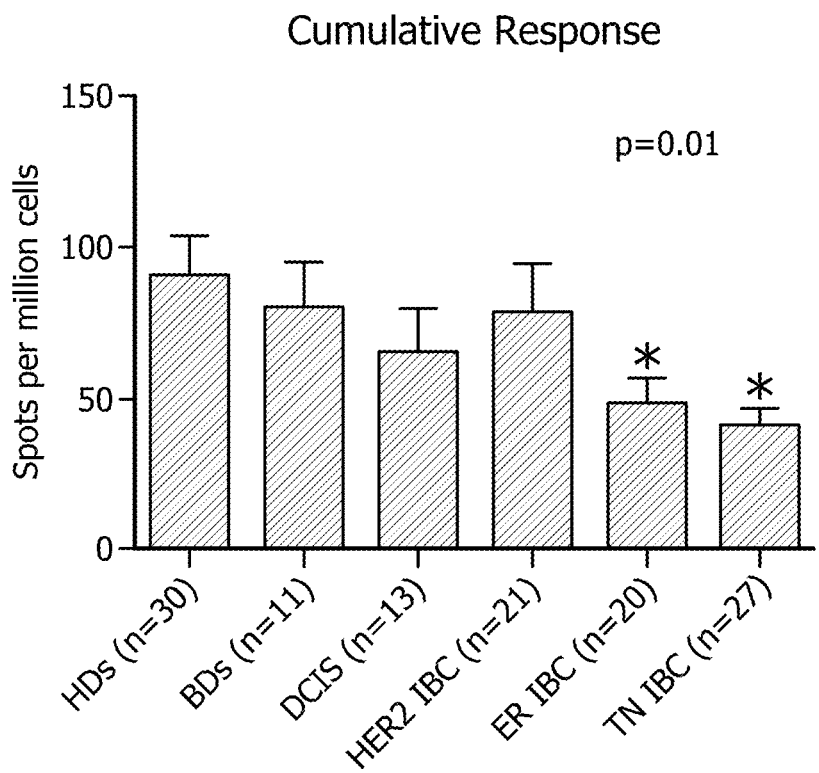
FIGS. 24A-24C show anti-HER3 CD4 Th1 cell responses decline from HDs (healthy donors) to ER IBC/ER$^{pos}$IBC (estrogen receptor positive invasive breast cancer ("IBC")) and TN IBC (triple negative IBC). The figures show histograms (left panels) of IFN-γ ELISpot analysis of systemic CD4$^+$ Th1 cell response. Patient groups studied were: HD: BD (benign breast biopsy); DCIS (HER2 positive ("HER2$^{pos}$") ductal carcinoma in situ); HER2 IBC/HER2$^{pos}$ IBC; ER IBC/ER$^{pos}$ IBC (estrogen receptor positive IBC); and TN IBC (triple negative IBC). Corresponding tables to the right of the respective histograms are individual comparisons by student's t-test between two groups at a time. One-way ANOVA tests were performed on all groups.
Figure 24B:
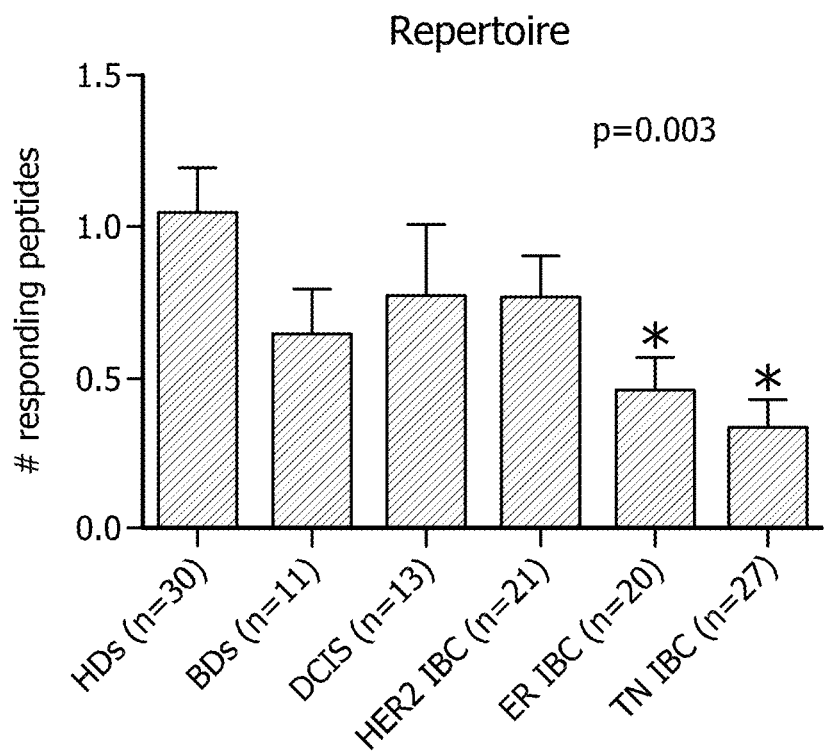
Figure 24C:
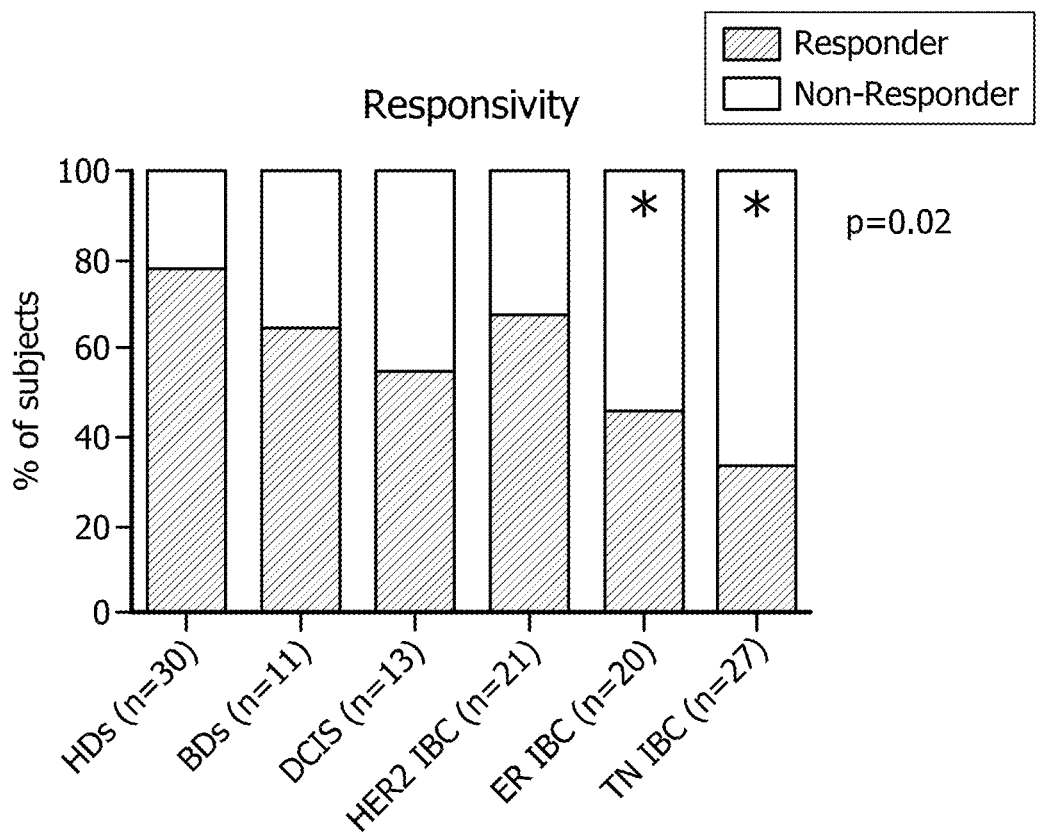

There is a Decline in CD4 Th1 Cell Anti-HER3 Immune Responses from Healthy Donors to Subsets of Invasive Breast Cancer Comparing HDs, BDs, DCIS, HER2$^{pos}$IBC, ER$^{pos}$ IBC, and TN IBC, there was a decline in all three immune parameters, reaching the lowest point in TN IBC: cumulative response (90 versus 80 versus 66 versus 79 versus 48 versus 40, p=0.01, respectively, as shown in FIG. 24A), repertoire (1.0 versus 0.6 versus 0.8 versus 0.8 versus 0.5 versus 0.3, p=0.003, respectively, as shown in FIG. 24B) and responsivity (76.7% versus 63.6% versus 53.8% versus 66.7% versus 45.0% versus 33.3%, p=0.02, respectively, as shown in FIG. 24C). Notably, these differences were not only statistically significantly higher, but also more than double, in HDs compared to TN IBC patients across all three immune parameters: cumulative response (90 versus 40, p=0.00$^2$), repertoire (1.0 versus 0.3, p=0.0004) and responsivity (76.7% versus 33.3/%, p=0.001). Compared to TN IBC patients, BDs had significantly higher cumulative response (40 versus 80, p=0.007, respectively), DCIS patients had significantly higher repertoire (0.8 versus 0.3, p=0.04, respectively) and HER2$^{pos}$ IBC had significantly higher repertoire (0.3 versus 0.8, p=0.01) and responsivity (33.3% versus 66.7%, p=0.04, respectively). ER$^{pos}$ IBC patients had the second lowest anti-HER3 CD4 T cell responses and displayed statistically significantly lower responses compared to HDs across all three immune parameters: cumulative response (48 versus 90, p=0.03, respectively), repertoire (0.5 versus 1.0, p=0.008, respectively) and responsivity (45.0% versus 76.7%, p=0.03, respectively). Of note is the fact that, HER2' IBC anti-HER3 responses did not vary significantly from HDs, BDs or DCIS subjects.

Figure 25A:
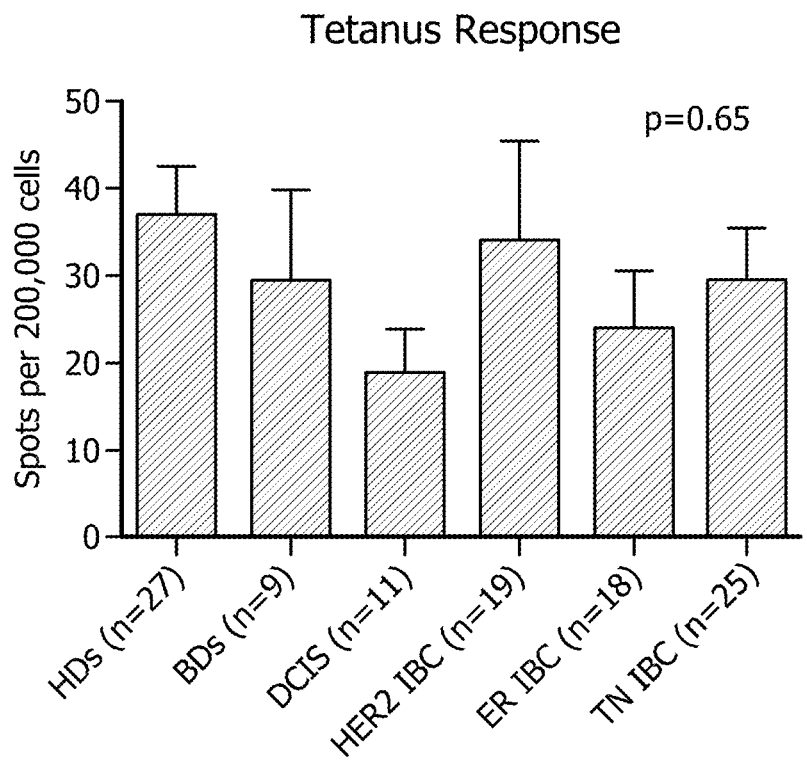
FIGS. 25A and 25B show loss of CD4 T cell response is specific to HER3 as there are no differences in tetatnus or anti-CD3/CD28 stimulation between tested patient groups. The figures show histograms (left panels) of IFN-γ ELISpot analysis of systemic CD4$^+$ Th1 cell response. Patient groups studied were: HD; BD; DCIS: HER2 IBC/HER2$^{pos}$ IBC; ER IBC/ER$^{pos}$ IBC; and TN IBC. Corresponding tables to the right of the respective histograms are individual comparisons by student's t-test between two groups at a time. One-way ANOVA tests were performed on all groups.
Figure 25B:
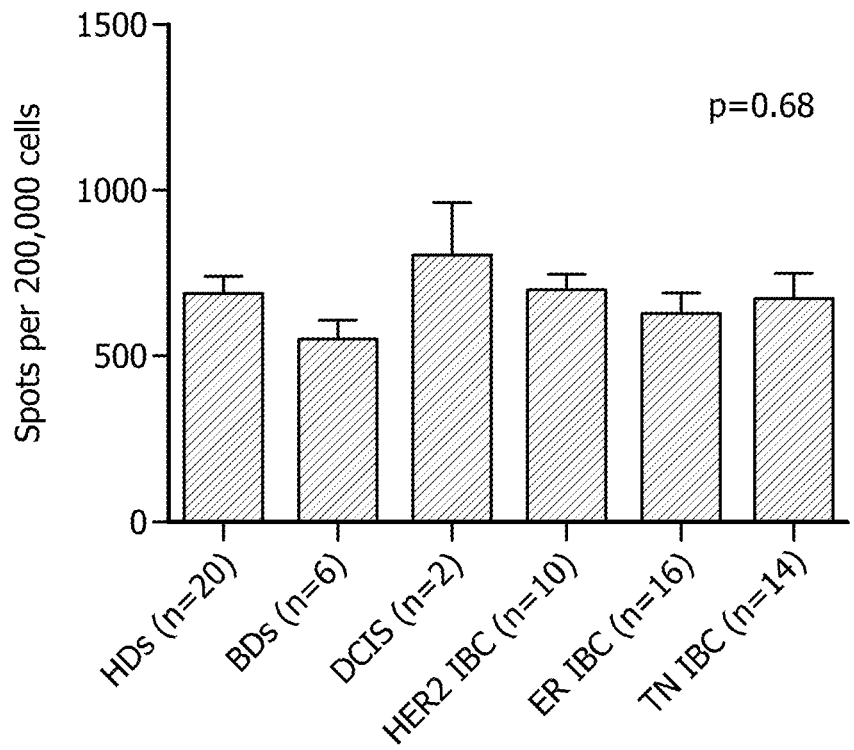

Lower CD4 Th1 Cell Anti-HER3 Immune Responses in Invasive Breast Cancer Patients are Specific to HER3 and are not Attributable to a Broad Deficiency in the Immune Response Tetanus responses and polyclonal stimulation with anti-CD3/CD28 responses were analyzed to compare and control for overall immune responsiveness. There was no difference in CD4 Th1 cell anti-tetanus response, as measured via ELISpot assay in spots per 200,000 cells, between HDs, BDs, DCIS, HER2$^{pos}$ IBC, ER$^{pos}$ IBC or TN IBC patients (37 versus 30 versus 19 versus 34 versus 24 versus 29, p=0.65, respectively, as shown in FIG. 25A). Importantly, anti-tetanus responses between HDs and TN IBC patients, the groups with the most divergent anti-HER3 CD4 Th1 cell responses, were similar (37 versus 29, p=0.37). Likewise, there was no difference in polyclonal stimulation with anti-CD3/CD28, with the majority of subjects in each group having robust spot development that was too numerous to count. Of those that were countable, there was no statistically significant difference between HDs, BDs, DCIS, HER2$^{pos}$ IBC. ER$^{pos}$ IBC or TN IBC patients (688 versus 549 versus 804 versus 699 versus 629 versus 675, p=0.68, respectively, as shown in FIG. 25B).

Figure 26A:
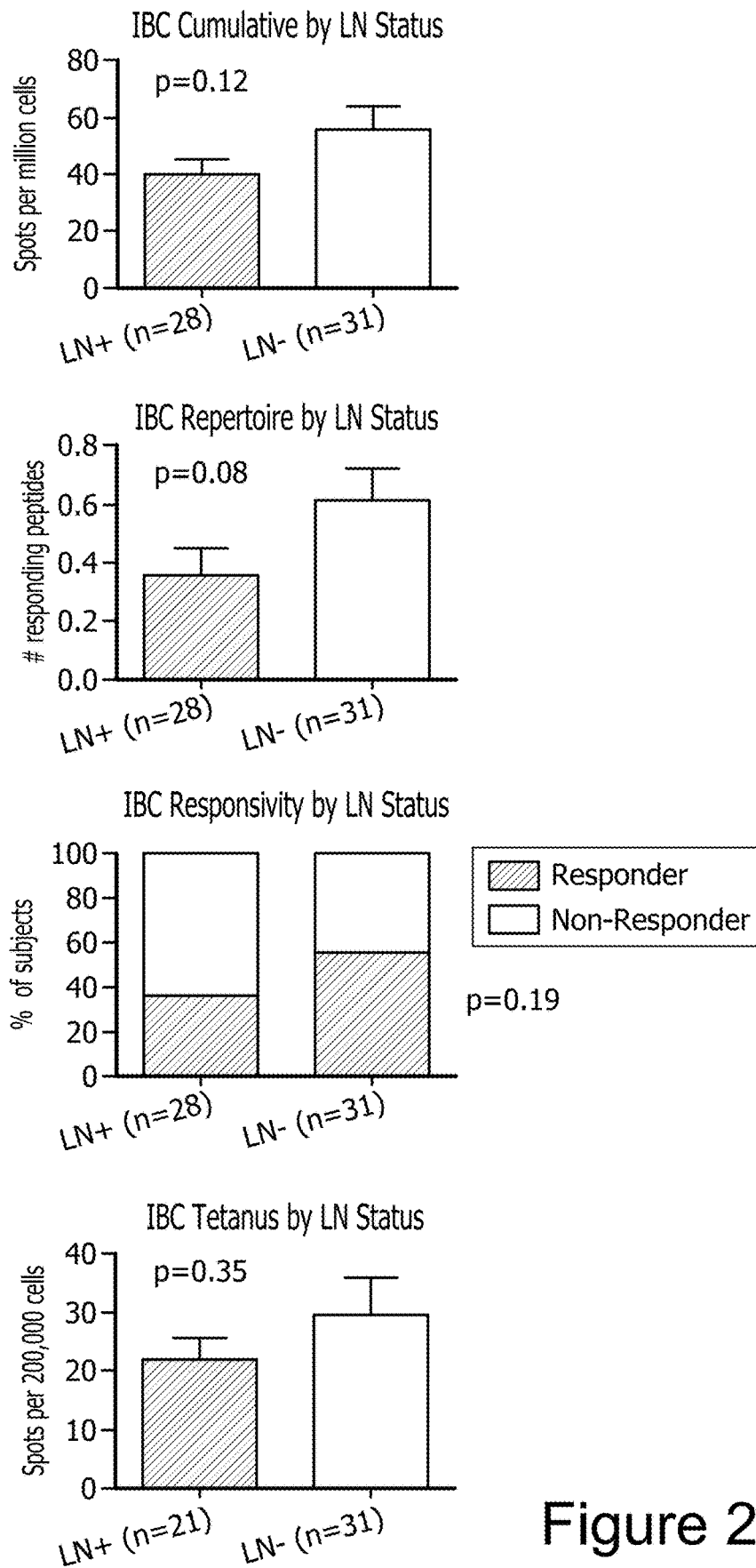
FIGS. 26A-26C show anti-HER3 CD4 Tcell responses correlate with recurrence and response to neo-adjuvant chemotherapy, but not with lymph node metastasis.
Figure 26B:
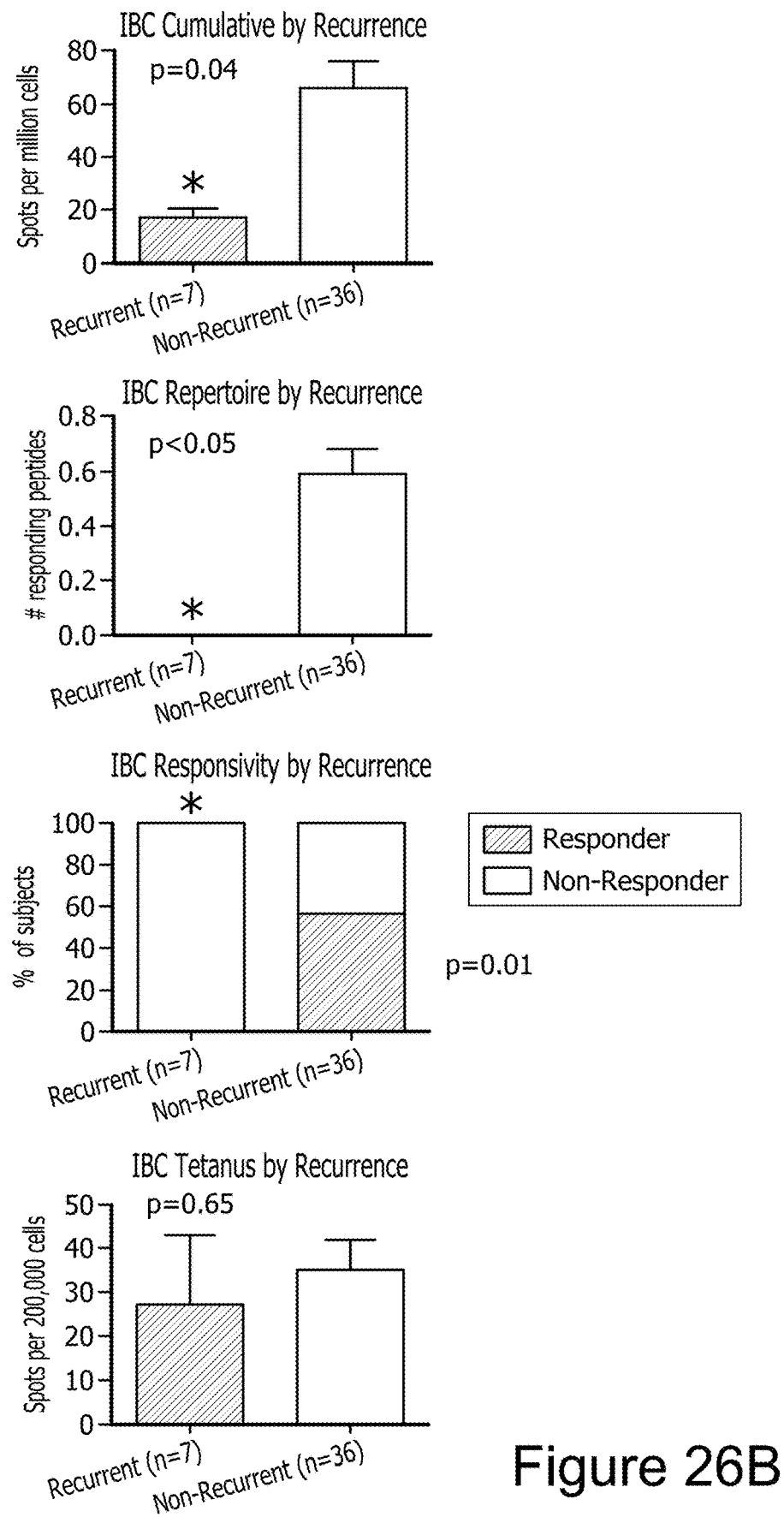
Figure 26C:
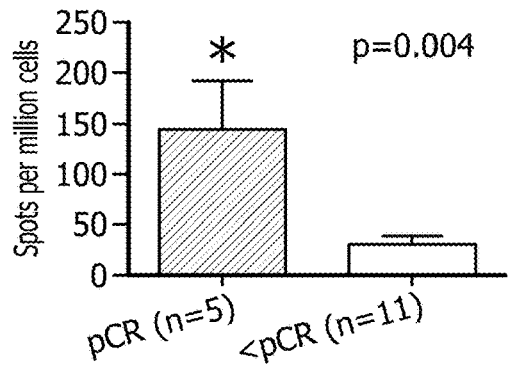
Figure 26C:
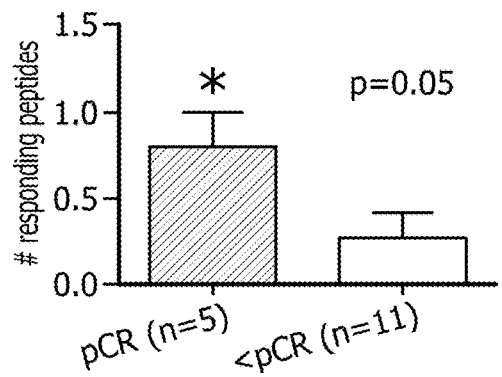
Figure 26C:
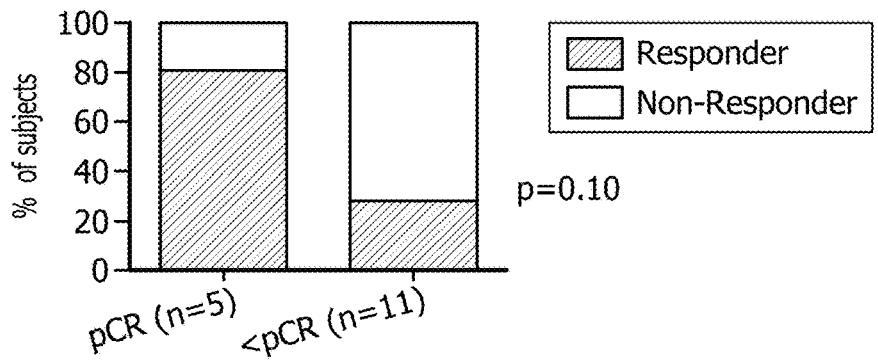
Figure 26C:
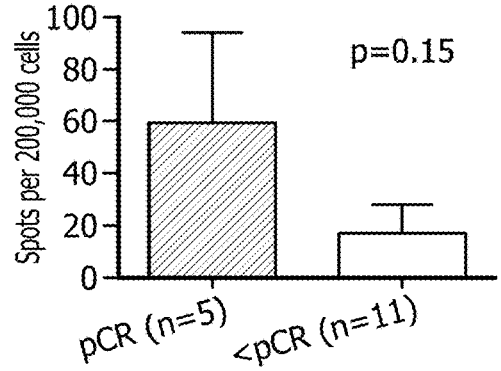

Invasive Breast Cancer Patients' Anti-HER3 CD4 Th1 Cell Responses Correlate with Prognosis and Characteristics of Tumor Aggression To determine whether anti-HER3 CD4 T cell responses correlated with characteristics of tumor aggression, IBC patients' immune responses were compared by lymph node status at initial surgery (lymph node positive ("LN$^{pos}$") versus lymph node negative ("LN$^{neg}$")), recurrence versus non-recurrence in patients who were at least 1 year out from diagnosis and response to neoadjuvant chemotherapy (pathologic complete response ("pCR") versus residual disease ("<pCR")). While LN$^{pos}$ IBC patients (n=28) had overall lower immune responses compared to LN$^{neg}$ patients (n=31) across all three parameters, none were statistically significant: cumulative response (40 versus 56, p=0.12, respectively), repertoire (0.4 versus 0.6, p=0.08, respectively) and responsivity (35.7% versus 54.8%, p=0.19, respectively) as shown in FIG. 26A. Of note, LN$^{pos}$ subjects included those with lymph node metastasis after neoadjuvant chemotherapy. Subjects who were LN$^{neg}$ post-neoadjuvant chemotherapy were excluded from analysis, given it was unknown whether they may have had positive nodes prior to treatment. Of patients who were at least a year out from diagnosis, those with recurrent breast cancer (either local or distant metastasis, n=7) had significantly lower anti-HER3 responses across all three immune parameters compared to those who remained disease-free (n=36): cumulative response (17 versus 66, p=0.04, respectively), repertoire (0.0 versus 0.6, p<0.05, respectively) and responsivity (0% versus 55.6%, p=0.01, respectively) as shown in FIG. 26B. Lastly, of patients receiving neoadjuvant chemotherapy (n=16), pCR (n=5) compared to <pCR (n=1) had significantly higher cumulative response (144 versus 32, p=0.004, respectively) and repertoire (0.8 versus 0.4, p=0.05, respectively) as shown in FIG. 26C. There was no statistically significant difference in responsivity between pCR and <pCR (80.0% versus 27.3%, p=0.10, respectively). It is note, there were no differences in tetanus response between LN$^{pos}$ and LN$^{neg}$ patients (22 versus 29, p=0.35, respectively), recurrent versus non-recurrent patients (27 versus 35, p=0.65, respectively) and pCR versus <pCR (17 versus 59, p=0.15, respectively). Thus, lower CD4 Th1 cell responses in IBC patients with characteristics of more aggressive tumors is specific to HER3.

Anti-HER3 CD4 Th1 Cell Responses by Healthy Donor Characteristics

Figure 27A:
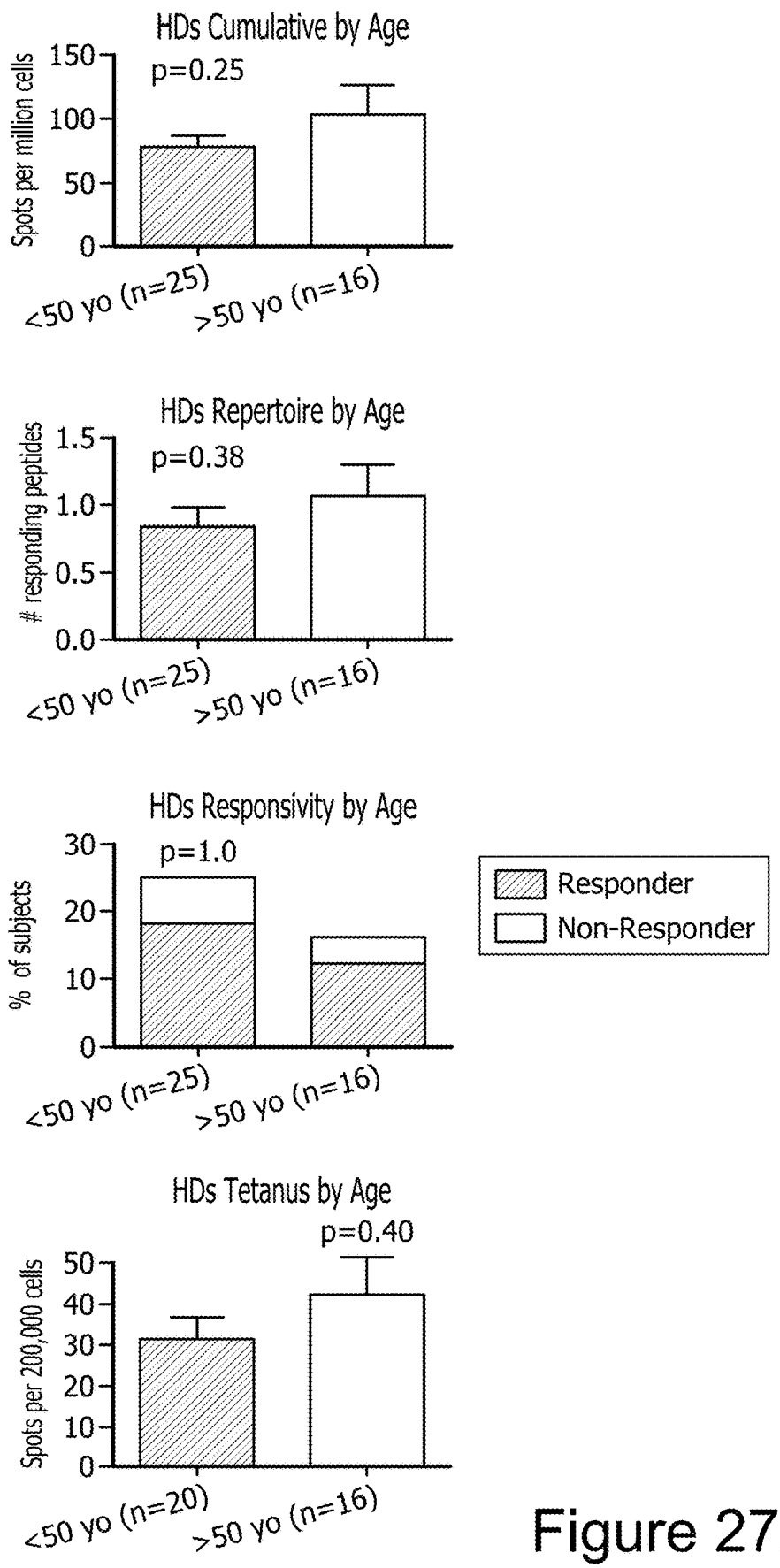
FIGS. 27A-27D show anti-HER3 CD4 T cell responses are significantly higher in post-menopausal HDs/BDs but do not differ by age, race or pregnancy history.
Figure 27B:
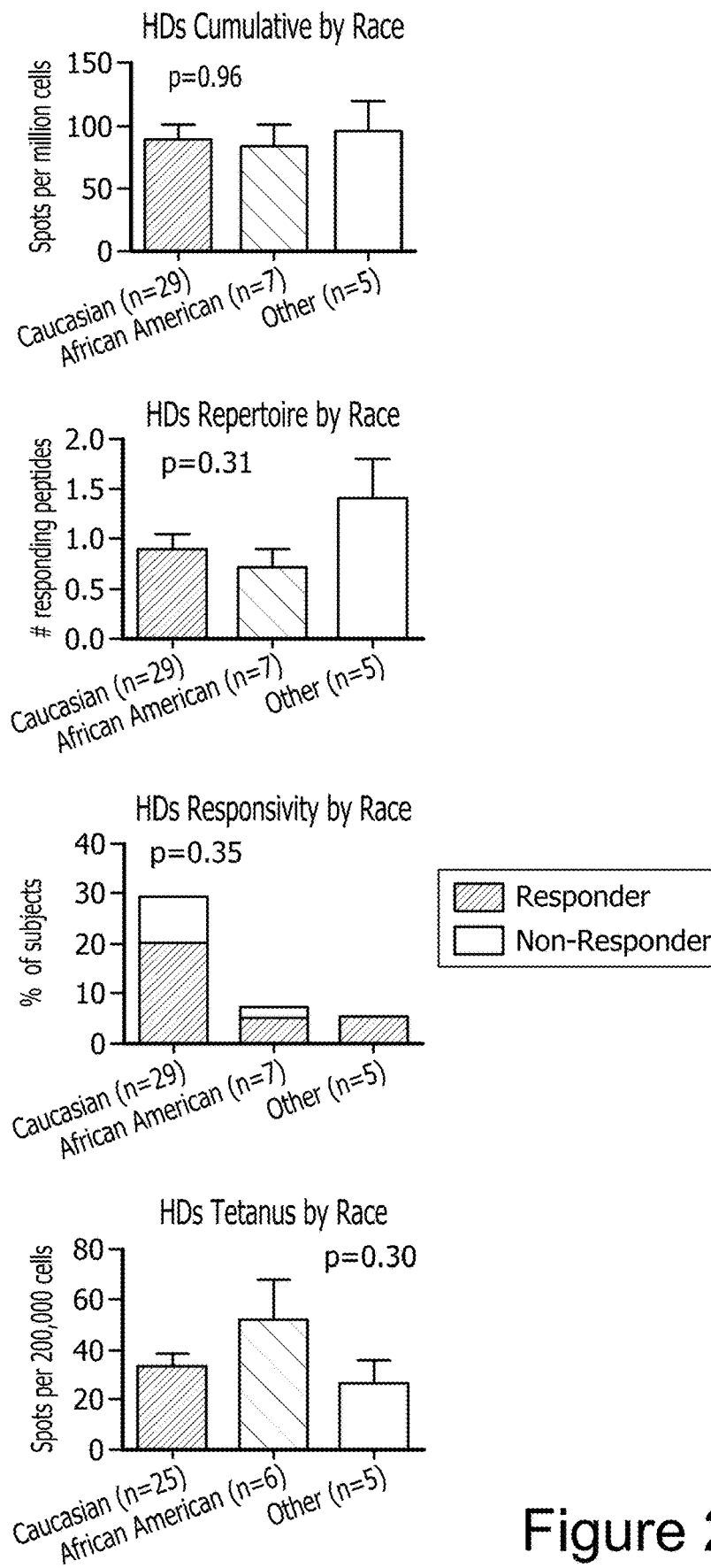
Figure 27C:
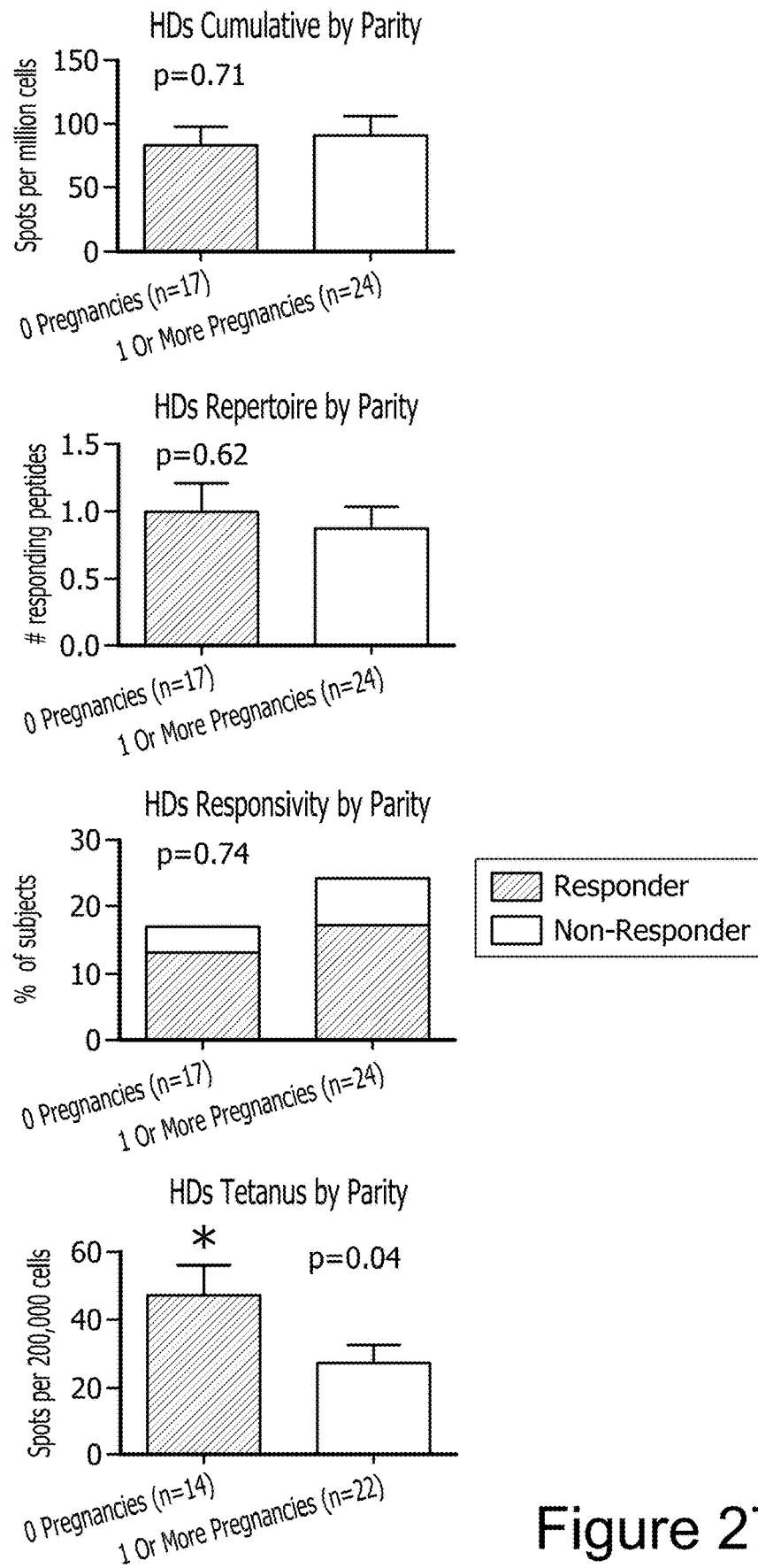
Figure 27D:
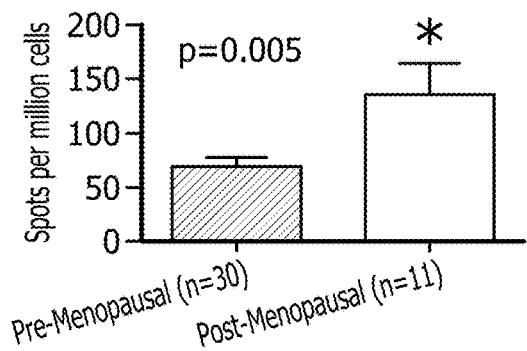
Figure 27D:
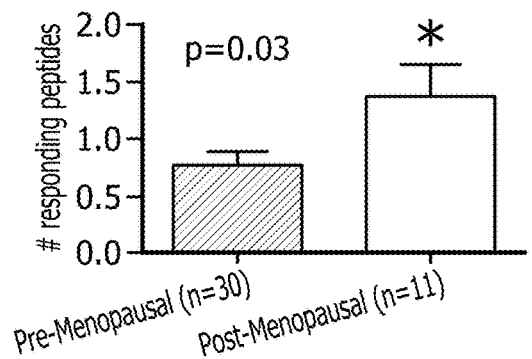
Figure 27D:
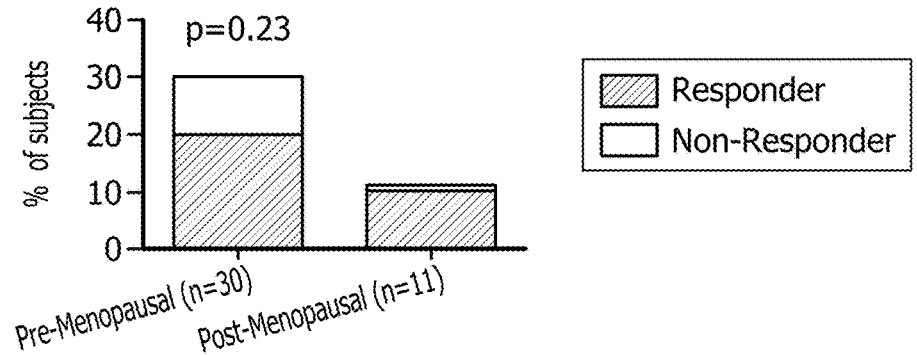
Figure 27D:
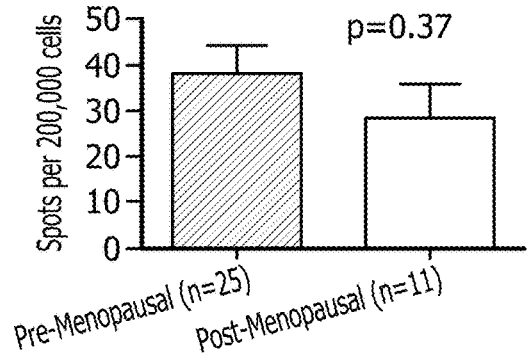

Anti-HER3 CD4 Th1 responses were compared in HDs and BDs by age (<50 years (n=25) or >50 years (n=16)), race (Caucasian (n=29), African American (n=12) or other (n=5)), pregnancy status (0 (n=17) or 1 or more pregnancies (n=24)) and menopausal status (pre-menopausal (n=30) or post-menopausal (n=11)). There were no differences in cumulative peptide response, repertoire or responsivity by age (FIG. 27A), race (FIG. 27B) or history of prior pregnancy (FIG. 27C). However, as seen in FIG. 27D, post-menopausal women, compared to pre-menopausal women, had significantly higher cumulative response (136 versus 70 spots per million cells, p=0.005, respectively) (top panel) and repertoire (1.4 versus 0.8 peptides, p=0.03, respectively) (second panel). There was no statistically significant difference in responsivity (90.9% versus 66.7%, p=0.23, respectively) (third panel). There was also no statistically significant difference in tetanus response between pre- and post-menopausal women (bottom panel), indicating the difference in immune response by menopausal status was specific to HER3.

ELISpot Assays are Precise as Demonstrated by a Linearity Precision Assay

Figure 28:
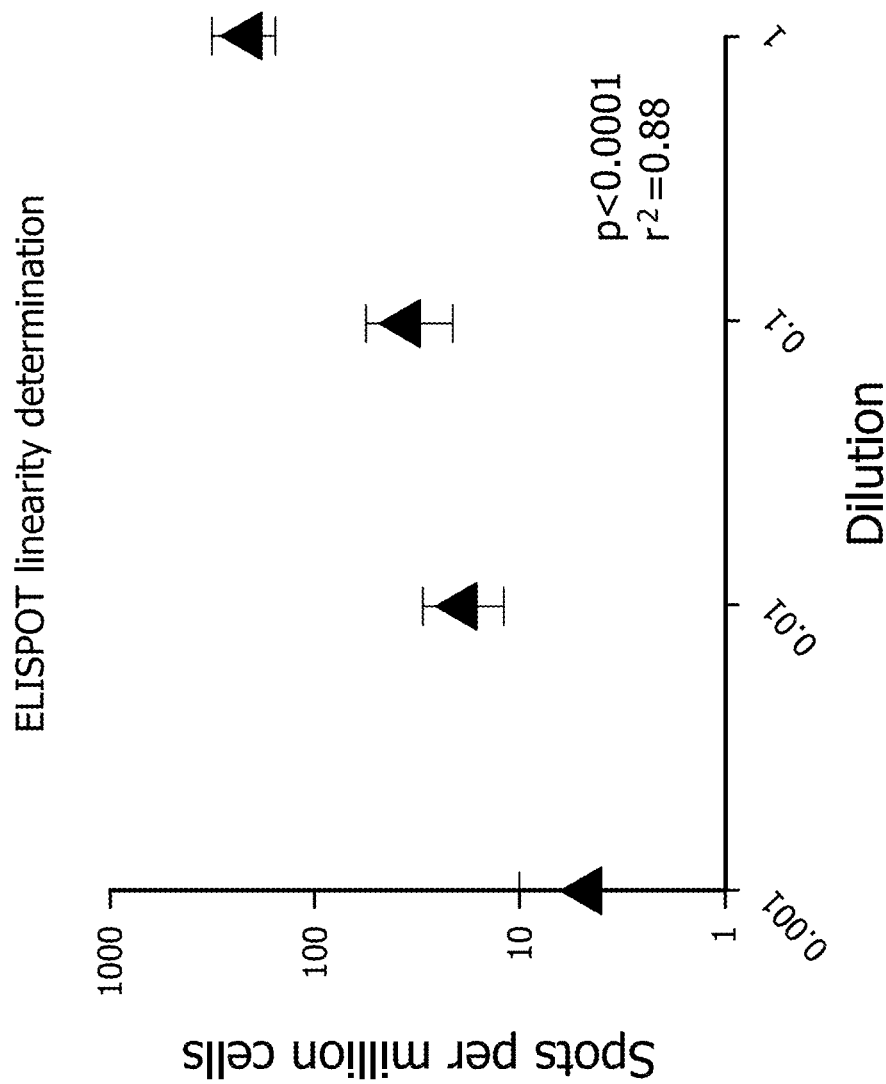
FIG. 28 is a graph of ELISpot linearity determination. ELISpot assays were determined to be linear and precise under the operator who performed all assays for this study by serial dilution of a known anti-HER3 CD4 T cell responder into media. Cumulative response followed a linear regression curve going from a dilution of 1.0 to 0.1 to 0.01 to 0.001 (230 to 35 to 12 to 5 spots per million cells, p<0.0001, $r^2$=0.88, respectively).

ELISpot assays have been previously validated in our laboratory. To confirm the precision of this assay under the operator who conducted all experiments for this study, a linearity precision assay was performed with serial dilutions from a known high anti-HER3 CD4 T cell responder. Peripheral blood monocytes were serially diluted into media from a concentration of 1.0 to 0.1 to 0.01 to 0.001 and cumulative anti-HER3 immune response was measured in spots per million cells. FIG. 28 shows there was a linear decline in spots going from a cumulative value of 230 to 35 to 12 to 5, respectively (p<0.0001, r=0.88).

Discussion

Knowledge of the immune system's role in cancer development, progression and prognosis is rapidly expanding. It is well established that immunodeficient states increase risk of cancer development, not only from tumors of viral origin but also from tumors of non-viral origin. Boshoff, C., et al., *Nature Rev. Cancer* 2:373-82 (2002): Shell, A. G., *World J. Surg.* 10:389-96 (1986); Penn, I., *Transplantation* 61:274-78 (1996); and Penn. I., Transplantation 60:1485-91 (1995). It is also known that certain immune phenotypes are associated with breast cancer: circulating inflammatory cytokines TNF-α and IL-6 are higher in breast cancer patients and low CD4$^{pos}$CD8$^{pos}$ T cell ratios are linked to more aggressive breast cancer phenotypes while tumor infiltrating lymphocytes are associated with a better prognosis in some breast cancers. Alokail, M. S., et al., *Med. Oncol.* 31(8):38 (2014) doi: 10.1007/s12032-014-0038-0; Jai, Y., et al., *Med. Oncol.* 31:981 (2014): and Matsumoto, H., et al., *J. Clin. Pathol.* doi:10.1136/jclinpath-2015-202944. However, evidence linking loss of immune recognition to specific molecular oncodrivers in otherwise immunocompetent hosts is relatively newer. Only recently has there been shown to be a decline in native anti-HER2 CD4 Th1 cell responses going from healthy donors to HER2$^{pos}$ DCIS to HER2$^{pos}$ IBC, one of the first studies showing a lost immune response to this specific oncodriver in breast tumorigenesis. Those having ordinary skill in the art will readily appreciate that the identification and understanding of such specific losses will have much potential for specific immuno-targeting therapy.

This study showed (1) there is a decline in the anti-HER3 CD4 Th1cell response going from HDs to ER$^{pos}$ and TN IBC. (2) the anti-HER3 response correlates with prognosis, specifically lower responses are associated with recurrence while higher responses are associated with pCR to neoadjuvant chemotherapy, and (3) post-menopausal HDs have significantly higher anti-HER3 immune responses. All of these findings will have diagnostic and clinical uses for anti-HET3 CD4 Th1 cell response.

Anti-HER3 CD4 Th1 cell responses were highest in HDs and lowest in TN IBC, a group whose prognosis is more severely impacted by HER3 overexpression than other types of IBC. Bae, et al, and Czopek, J., et al. While HER3 expression is unknown in the presently studied cohort of IBC patients, it may be that the TN IBC and ER$^{pos}$ IBC groups have higher levels of HER3 expression compared to the HER2$^{pos}$ IBC cohort, which displayed responses similar to that of HDs. Indeed, our prior study showed the anti-HER2 CD4 Th1 cell response correlated directly with HER2 expression; there was a significant decline in HER2$^{pos}$ IBC but not in HER2$^{neg}$ IBC. Not only does HER3 have a greater impact on prognosis of TN IBC compared to receptor-expressing breast cancers, but even in TN IBC it may have a greater impact on prognosis of HER2 (0) compared to HER2 (1+) tumors. Schmidt, G., et al., *Arch. Gynecol. Obstet.* 290:1221-29 (2014) This may in part explain the similarity in immune response between HER2$^{pos}$ IBC and HDs. If the tumor is already propogating due to HER2 overexpression, there is no drive for tumor evolution to evade immunosurveillance. If, however, the immune system is already recognizing and targeting HER2, the tumor may adapt via HER3 overexpression, where immune evasion becomes evolutionary advantageous to tumor cell survival.

Interestingly, ER$^{pos}$ IBC displayed anti-HER3 CD4 Tcell responses similar to that of TN IBC and significantly lower than HDs or HER2$^{pos}$ IBC. While HER3 expression is less prognostically significant in ER$^{pos}$ IBC compared to TN IBC, evidence indicates HER3 mRNA expression is positively correlated with ER expression. Fujiwara, S., et al., *Breast Cancer* 21:472-81 (2014) This may explain the lower immune response seen in this subgroup of IBC.

Breast cancer patients with recurrent disease had lower anti-HER3 CD4 Th1 responses compared to patients who remained disease-free, indicating immunosurveillance may be an important mechanism for long-term therapeutic success. It is also possible recurrent patients were more likely to have high HER3 expressing tumors, which itself correlates with higher risk of recurrence, metastasis and worse overall survival. Li, Q., et al., *Oncology Reports* 30:2563-70 (2013); Smirnova. T., et al., *Oncogene* 31:706-15 (2012); and Ocana, A., et al., *J.N.C.I* 105(4):266-73 (2013). Moreover, immuno-editing has been proposed as an escape mechanism whereby neoplastic cells are selectively eliminated by the immune system until they evolve to express molecular oncodrivers, such as HER3, that evade immune recognition. Dunn. G. P., et al., *Nature Immunology* 3(11): 991-8 (2008). Thus, HER3 expression may be possible due to lack of immunosurveillance, which then enhances risk of recurrence. Interestingly, recent evidence suggests recurrent tumors may not be pathologically identical to primary tumors. Discordant rates between primary and secondary tumors are particularly high for progesterone receptor and discordance of any type points to worse prognosis of recurrent tumors. Idirisinghe, P. K. A., et al., *Am. J. Clin. Pathol.* 133:416-29 (2010); Broom, R J., et al., *Anticancer Research* 29:1557-62 (2009); and Liedtke, C., et al., *Annals of Oncology* 20:1953-58 (2009). It is believed no studies to date have compared HER3 expression between primary and secondary tumors: it is unknown whether HER3 expression is discordant between primary and recurrent tumors and whether HER3 expression may represent an escape mechanism for recurrence to occur. If so, targeting patients with low anti-HER3 CD4 T cell responses may boost immunosurveillance and help prevent long-term recurrence.

Also implicating the immune system's role in prognosis, patients with pCR to neoadjuvant chemotherapy had significantly higher anti-HER3 CD4 T cell responses than patients with <pCR HER3 signalling has been shown to mediate acquired resistance to targeted therapies. Sergina, N. V., et al., *Nature* 445:437-41 (2007); and Frogne, T., et al., *Breast Cancer Res. Treat.* 114:263-75 (2009). Here, it is implicated not in acquired resistance but in initial resistance, making the anti-HER3 immune response a potential prognostic marker of patients that would most benefit from neo-adjuvant treatment. Further studies should elucidate whether the anti-HER3 immune response is not only prognostic but can also be intervened upon to boost response to treatment.

In the present study a subset of HDs, specifically post-menopausal women, demonstrated higher anti-HER3 responses. Unlike prior findings with anti-HER2 responses, however, there was no difference based on pregnancy history. While biologically this higher anti-HER2 response could be attributed to breast involution and the subsequent exposure of cellular proteins to immune surveillance with pregnancy, such changes in the breast parenchyma are less likely in menopause. Press, M. F., et al., *Oncogene* 5:953-62 (1990). Changes in breast density with hormonal changes (as in menopause) have been observed on imaging, which may mimic breast involution in pregnancy and likewise expose cellular proteins that are normally expressed in breast tissue to the immune system Clendenen, T. V., et al., *Magnetic Resonance Imaging* 31:1-9 (2013). An alternate explanation may attribute the higher anti-HER3 immune response in post-menopausal women to a difference in risk. Expression of various breast cancer oncodrivers is clearly age dependent: HER2$^{pos}$ IBC becomes less likely with age while ER$^{pos}$ IBC becomes more likely. Clark, G. M., et al., *J. Clin. Oncol.* 2:1102-09 (1984); Eppenberger-Castori, S., et al., *Int. J. Biochem. and Cell Biol.* 34:1318-30 (2002). Further, these two receptors are not independent of each other as ER/PR expression with age is HER2 dependent and vice versa. Neven, P., et al., *Breast Cancer Res. Treat.* 110:153-59 (2008). TN IBC patients, a group with the lowest anti-HER3 immune response and most sensitive prognostically to HER3 overexpression, occurs more frequently in pre-menopausal women. Bae, et al, and Howlander. N., et al., *J.N.C.I.* 106(5):1-8(2014). Thus, the subset of pre-menopausal HDs represent a group at higher risk of developing TN IBC while the post-menopausal HDs represent a group that has already surpassed this higher risk period and actually represent a group at lower risk of having both HER2 and HER3 overexpressing breast cancer. It is also notable that while TN IBC is more common in younger women, its occurrence in an older population portends a better prognosis for unknown reasons. Aapro, M., et al., annals of Oncology 23(6):vi52-55 (2012). If the higher anti-HER3 immune response is indeed due to a biological mechanism that occurs with menopause rather than a risk averse group, this may partially explain the better prognosis of TN IBC in post-menopausal women.

CONCLUSION

This example demonstrated a decline in the anti-HER3 CD4 Tcell response going from HDs, BDs and DCIS to ER$^{pos}$ and TN IBC. Furthermore, lower anti-HER3 responses correlated with recurrence and <pCR to neoadjuvant treatment, indicating this immune response may also play a prognostic role in invasive breast cancer. Most importantly, these results mirror those of the prior study showing a decline in the native anti-HER2 immune response going from HDs to HER2$^{pos}$ DCIS to HER2$^{pos}$ IBC. Such similar results are promising in not only confirming prior findings but also pointing to a larger role of the immune system in patrolling molecular oncodrivers. Interestingly, post-menopausal HDs had significantly higher immune responses than pre-menopausal HDs, a group that is generally at higher risk of developing HER3 overexpressing breast cancer and potentially pointing to a mechanism that mediates this risk. It will be important to determine whether HER3 pulsed DC1 vaccination can have a therapeutic and/or risk-modifying effect on the development of HER3 overexpressing breast cancer. It will likewise be important to continue to examine the immune system's role in other oncodriver-specific cancers.

Front of paper Conclusions: CD4 Th1 cell anti-HER-3 immune responses are lost from healthy donors to invasive breast cancer, most notably in TN IBC, a group with limited treatment options and markedly worse prognosis with HER-3 overexpression. Anti-HER3 immune responses also mitigate response to treatment and prognosis, pointing to a potential immunotherapy target. Addition of HER3 immunogenic peptides to DC1 vaccine may increase the population of IBC patients that could benefit from vaccination. Most importantly, these results mirror prior findings and point to a larger role of the immune system in patrolling molecular oncodrivers.

The findings in this Example, namely, that there is a significant loss of anti-HER3 CD4+ Th1 in breast tumorigenesis going from HDs to IBC can be appreciated by those of ordinary skill in the art to be useful in the diagnosis and treatment of HER3-expressing cancers, in particular breast cancers and in particular triple negative IBC. It is contemplated that blood tests can be developed to detect the circulating anti-cancer CD4+ Th1 response in subjects to take advantage of these findings. Preferably such blood tests will employ HER3 immunogenic peptides such as the 4 enumerated HER3 immunogenic peptides employed herein or any other MHC class II immunogenic peptides based on the type of cancer the patient is afflicted with and which are capable of inducing an immune response in the patient. As a non-limiting example, patients with recurrent breast cancer and lack of pCR to neoadjuvant therapy can be monitored with such blood tests to determine their anti-HER3 CD4 Th1 response and treated accordingly.

Low anti-HER3 response detected by a patient blood test or other means can be countered by restoration methods such as, for example, vaccines, and preferably vaccines based on a patient's monocyte-derived dendritic cells that are pulsed/incubated with HER3 immunogenic peptides, such as, for example, the 4 HER3 immunogenic peptides used in the herein Example. Those of ordinary skill in the art will readily appreciate there are other ways to restore patient immune response. In particular, for TN IBC patients, a group that inherently has limited treatment options, methods of measuring HER3 response, and if needed, methods to restore such response via a DC1 vaccine, may prove invaluable. Anti-HER3 immune response can also be used as a potential prognostic biomarker of patients needing neoadjuvant treatment. A HER3-pulsed DC1 vaccine or other suitable vaccine might have a therapeutic and/or risk-modifying effect on the development of HER3-overexpressing breast cancers as well as other HER3-expressing cancers. The finding herein can be appreciated to be useful for the development of an array blood tests and assays as contemplated herein for diagnosis and/or therapy.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of at least one of (i) eliciting an immune response to a HER3-expressing cancer and (ii) treating a HER3-expressing cancer in a mammal, the method comprising:
   pulsing a dendritic cell obtained from said mammal with a composition comprising a peptide consisting of p91 (AGRIYISANRQLCYH, SEQ ID NO: 7) to generate a peptide-loaded dendritic cell;
   activating said peptide-loaded dendritic cell with at least one toll-like receptor agonist to generate an activated dendritic cell; and
   administering said activated dendritic cell to said mammal.

2. A method of treating a cancer patient who has lost an anti-HER3 CD4+ Th1 immune response, the method comprising:
   administering to said cancer patient at least one dose of an antigen-pulsed autologous dendritic cell,
   wherein said antigen-pulsed autologous dendritic cell was prepared by pulsing an autologous monocyte derived dendritic cell with a HER3 MHC Class II immunogenic peptide consisting of p91 (AGRIYISANRQLCYH, SEQ ID NO: 7).

3. The method of claim 1, wherein said cancer patient has triple negative invasive breast cancer.

* * * * *

SEQUENCE LISTING

```
<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Tyr Glu Arg Cys Glu Val Val Met Gly Asn Leu Glu Ile Val
1               5                   10                  15

Leu Thr Gly His Asn Ala Asp Leu Ser Phe Leu Gln Trp
            20                  25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Trp Pro Pro His Met His Asn Phe Ser Val Phe Ser Asn Leu Thr
1               5                   10                  15

Thr Ile Gly Gly Arg Ser Leu Tyr Asn
            20                  25
```

```
<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Thr Ile Gly Gly Arg Ser Leu Tyr Asn Arg Gly Phe Ser Leu Leu
1               5                   10                  15

Ile Met Lys Asn Leu Asn Val Thr Ser
            20                  25

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Glu Val Val Met Gly Asn Leu Glu Ile Val Leu Thr Gly His
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Trp Pro Pro His Met His Asn Phe Ser Val Phe Ser Asn Leu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Thr Ile Gly Gly Arg Ser Leu Tyr Asn Arg Gly Phe Ser Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gly Arg Ile Tyr Ile Ser Ala Asn Arg Gln Leu Cys Tyr His
1               5                   10                  15
```